US011566226B2

(12) United States Patent
Brady et al.

(10) Patent No.: US 11,566,226 B2
(45) Date of Patent: *Jan. 31, 2023

(54) NATURAL KILLER CELLS

(71) Applicant: Imperial College of Science, Technology and Medicine, London (GB)

(72) Inventors: Hugh J. M. Brady, London (GB); Matthew Fuchter, London (GB); Tomasz Kostrzewski, Welwyn (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 373 days.

This patent is subject to a terminal disclaimer.

(21) Appl. No.: 16/497,669

(22) PCT Filed: Mar. 28, 2018

(86) PCT No.: PCT/GB2018/050818
§ 371 (c)(1),
(2) Date: Sep. 25, 2019

(87) PCT Pub. No.: WO2018/178666
PCT Pub. Date: Oct. 4, 2018

(65) Prior Publication Data
US 2020/0032210 A1 Jan. 30, 2020

(30) Foreign Application Priority Data
Mar. 28, 2017 (GB) .................................. 1704953

(51) Int. Cl.
*C12N 5/0783* (2010.01)
*A61K 35/17* (2015.01)

(52) U.S. Cl.
CPC ............ *C12N 5/0646* (2013.01); *A61K 35/17* (2013.01); *C12N 2501/125* (2013.01); *C12N 2501/2307* (2013.01); *C12N 2501/998* (2013.01); *C12N 2501/999* (2013.01); *C12N 2533/50* (2013.01)

(58) Field of Classification Search
None
See application file for complete search history.

(56) References Cited

U.S. PATENT DOCUMENTS

2007/0048290 A1* 3/2007 Tsai .................. G01N 33/5011
435/372
2011/0044961 A1 2/2011 Beck

FOREIGN PATENT DOCUMENTS

| CN | 105596336 | 5/2016 |
|---|---|---|
| WO | 2006/023209 | 3/2006 |
| WO | 2012/128622 | 9/2012 |

OTHER PUBLICATIONS

Haraguchi et al., J Immunol. May 15, 2009;182(10):6168-78 (Year: 2009).*
International Search Report and Written Opinion of the International Searching Authority, dated Jul. 31, 2018 in corresponding International Patent Application No. PCT/GB2018/050818.
Beck et al., "The Notch Ligands Jagged2, Delta1, and Delta4 Induce Differentiation and Expansion of Functional Human NK Cells from CD34+ Cord Blood Hematopoietic Progenitor Cells", Biol Blood Marrow Transplant, 15: 1026-1037 (2009).
Ni et al., "IGF-1 promotes the development and cytotoxic activity of human NK cells", Nature Communications, 4: 1479, pp. 1-11 (2013).
Male et al., "The transcription factor E4bp4/Nfil3 controls commitment to the NK lineage and directly regulates Eomes and Id2 expression", The Journal of Experimental Medicine, 211(4): 635-642 (2014).
Gibbs et al., "The nuclear receptor REV-ERBα mediates circadian regulation of innate immunity through selective regulation of inflammatory cytokines", PNAS, 109(2): 582-587 (2012).
Kojetin et al., "Identification of SR8278, a Synthetic Antagonist of the Nuclear Heme Receptor REV-ERB", ACS Chemical Biology, 6(2): 131-134 (2011).
Kostrzewski et al., "Multiple Levels of Control Determine How E4bp4/Nfil3 Regulates NK Cell Development", Journal of Immunology, 200(4): 1370-1381 (2018).
Great Britain Search Report, dated Dec. 29, 2017 in corresponding Great Britain application No. GB1704953.7.
Dong et al., "A validated ultra-performance liquid chromatography-tandem mass spectrometry method to identify the pharmacokinetics of SR8278 in normal and streptozotocin-induced diabetic rats", Journal of Chromatography B, 1020: 142-147 (2016).

* cited by examiner

Primary Examiner — Daniel C Gamett
(74) Attorney, Agent, or Firm — Wenderoth, Lind & Ponack, L.L.P.

(57) ABSTRACT

This invention relates to Natural Killer (NK) cell populations, to methods of producing the same and therapeutic applications thereof. More specifically, the invention relates to the expansion of NK cells by increasing the expression of specific transcription factors associated with NK cell production.

17 Claims, 31 Drawing Sheets
Specification includes a Sequence Listing.

| | | |
|---|---|---|
| Mouse | MQLRKMQTIKKEPAPLDPTS | 20 |
| Rat | MQLRKMQAIKKEPASLDPTG | 20 |
| Human | MQLRKMQTVKKEQASLDASS | 20 |
| Chicken | MQLRKMQTLKKEHGSVDTSS | 20 |
| Xenopus | -----MPTIKKEQECADSRM | 15 |

*.:*:***     *

K118

| | | |
|---|---|---|
| Mouse | LENKLIALGEENATLKAELL | 120 |
| Rat | LENKLIALGEENATLKAELL | 120 |
| Human | LENKLIALGEENATLKAELL | 120 |
| Chicken | LENKLIALGEENATLKAELL | 120 |
| Xenopus | LENKLIALGEENASLKTELL | 113 |

************::***

K219

| | | |
|---|---|---|
| Mouse | PENKFPVIKQEPVELESFAR | 230 |
| Rat | PENKFPVIKQEPVELESFAR | 230 |
| Human | PENKFQIIKQEPMELESYTR | 230 |
| Chicken | PENKFQIIKQEPIELE---R | 227 |
| Xenopus | TDIKSQRIKQEQMEAGNFSR | 224 |

.:.*.. ****.:*     *

K337

| | | |
|---|---|---|
| Mouse | RIKAKAMQVKVEALDSEFEG | 347 |
| Rat | RIKAKAMQVKVEALDSEFEG | 347 |
| Human | RIKAKAMQIKVEAFDNEFEA | 347 |
| Chicken | RIKAKAMQVKVEAMDNDYDA | 343 |
| Xenopus | RIKAKAMQIKVESLESELNS | 342 |

*******:*:::::  :.

K394

| | | |
|---|---|---|
| Mouse | VTNIQDWSLKSEHWHHKELS | 400 |
| Rat | VTNIQDWSLRSEHWHHKELG | 400 |
| Human | VTNIQDWSLKSEHWHQKELS | 400 |
| Chicken | VTNIQDWSLKPELWHQKELN | 396 |
| Xenopus | VTNIQDWPLKPGQWHHRELE | 394 |

*******.*:.:.**...*

E

*Eomes*

*Tbet*

NATURAL KILLER CELLS

FIELD OF THE INVENTION

This invention relates to expanded Natural Killer (NK) cell populations, to methods of producing the same and therapeutic applications thereof. More specifically, the invention relates to the expansion of NK cells by increasing the expression of specific transcription factors associated with NK cell production.

BACKGROUND OF THE INVENTION

There has been an increase in interest in Natural Killer (NK) cells as they are cytotoxic against cancerous, pathogen-infected and otherwise damaged cells. NK cells are innate lymphoid cells (ILCs), specifically large granular cytotoxic lymphocytes that bridge the innate and the adaptive arms of the immune response. They make up 10-15% of circulating lymphocytes in the peripheral blood. NK cells also exhibit the highest level of cytotoxic activity within the immune system. Therefore, altered NK cell functionality or numbers impact the functioning of the immune system against infection and cancer. For example, a large scale study in Japan has shown that reduced levels of NK cells in a cohort of people aged over 40 is associated with a significantly higher incidence of cancer.

Similarly to B cells and T cells, these NK cells are derived from Common Lymphoid Progenitor (CLP) cells that in turn come from Haematopoietic Stem Cells (HSCs). However, NK cells are different from B and T cells as they lack specific cell surface antigen receptors. Due to this, NK cells may kill cancerous and pathogen-infected cells without prior sensitisation, making them part of the innate immune response. They also have a critical role in tumour immunosurveillance by directly influencing the adaptive immune response.

Activation of NK cells triggers them to release perforin and cytoplasmic granules containing granzymes. Perforin polymerises to form pores on target cells in the presence of $Ca^{2+}$. Granzymes may enter these pores into target cells, causing DNA fragmentation and apoptosis. NK cells may also secrete cytokines, which trigger the action of other immune cells in the adaptive arm of the immunity.

Due to the importance of NK cells in immune response against pathogen infection and cancer cells, multiple clinical trials have tested the efficacy of NK cells in adoptive transfer protocols. In adoptive transfer, NK cells isolated from the blood of donors are expanded ex vivo and matured into healthy and functional NK cells prior to transfusion into recipients. However, to be effective it is crucial that NK cell donors are be screened for their KIR genotype, where the donor must have the appropriate KIR allelic polymorphism to the recipient to allow recognition of target cells for destruction. In any event, studies have found that the expanded products have lower clinical success rate than expected, with less ability to kill cancerous or infected cells. Thus, there are significant barriers to the current adoptive transfer protocols.

An alternative therapeutic approach is to increase the number of endogenous NK cells. One method is the administration of cytokines that are essential for NK cell development. Administration of IL-2 and IL-15 was predicted to enhance NK cell development. IL-2 promotes the proliferation and cytotoxicity of NK cells, whereas IL-15 promotes the development and expansion of NK cells. However, in in vivo studies, the cytokines were found only stimulate a minimal expansion of NK cells with reduced half-life, even at a very high dose. Further, administered cytokines often leads to systemic toxicity due to inappropriate activation of immune responses and the induction of NK cell apoptosis.

Thus, using conventional methods and techniques, producing large numbers of NK cells is difficult, and producing fully functional NK cells with high cytotoxicity is even harder. There is currently no drug available that selectively increases NK cell numbers. Therefore, there is a need to develop new methods of NK cell production; both ex vivo to produce large numbers of functional NK cells for therapeutic and research use; and in vivo.

SUMMARY OF THE INVENTION

Natural Killer (NK) cells have a critical role in the immune system where they destroy cancerous, pathogen-infected or damaged cells. Boosting NK cell number or functionality is predicted to increase the killing of these cells. Existing therapies such as NK cell adoptive transfer and cytokine enhancement of endogenous NK cells are not very successful in terms of their efficacy.

NK cells are differentiated from the HSCs in the bone marrow and distributed throughout lymphoid and non-lymphoid tissues including lymph nodes, spleen, peripheral blood, lungs and liver. Specific cytokines and transcription factors are needed to encourage HSCs to develop into NK cells. Each cytokine and transcription factor must be present at a precise time and concentration in order to push differentiation from HSCs into NK cells. However, the precise hierarchy of cytokines and transcription factors governing NK cell maturation is still incompletely understood.

The present inventors have shown that abrogation of Notch signalling impedes NK cell production, and that the total lack of NK cell development from E4bp4$^{-/-}$ progenitors can be completely rescued by short exposure to Notch peptide ligands, particularly Delta-like ligand 4 (DLL4). Based on this work, the inventors have developed a method for the ex vivo expansion of NK cells from haematopoietic progenitor cells (HPCs), which minimises exhaustion and produces large numbers of functional NK cells.

The present inventors have previously shown that inhibiting the action of REV-ERB increases NK cell production. In particular, the inventors demonstrated that inhibiting the action of REV-ERB (e.g. using the REV-ERB antagonist SR8278) increases E4bp4 expression, which in turn increases NK cell production. The inventors have now shown that combining these two independent mechanisms (use of Notch ligands and REV-ERB inhibition) results in a surprisingly potent means for enhancing NK cell production, allowing for the production of large numbers of functional NK cells that are suitable for in vivo therapeutic use more rapidly than the current methods.

In addition, the present inventors have also now shown that post-translational modification for E4bp4 can regulate E4bp4 activity. In particular, the inventors have shown that phosphorylation and SUMOylation decrease E4bp4 activity, and that, conversely decreasing phosphorylation and/or SUMOylation of E4bp4 can increase E4bp4 activity. Thus, post-transcriptional modification of E4bp4 may be used to increase E4bp4 activity, and hence increase NK cell production.

Accordingly, the present invention provides an ex vivo method for expanding an NK cell population, comprising the steps of: a) culturing an haematopoietic progenitor cell (HPC) comprising sample obtained from an individual with a compound that inhibits the action of REV-ERB; b) culturing said cells in the presence of a Notch ligand; and c) expanding said cells in vitro to produce an NK cell population. In some embodiments, the vessel in which the HPCs are cultured is coated with the Notch ligand. The Notch ligand may be delta-like ligand 4 (DLL4), or a fragment thereof which retains the function of DLL4, or a molecule which mimics the function/activity of DLL4. Said compound may increase E4bp4 expression by decreasing REV-ERB activity. In some embodiments, said compound decreases the activity of REV-ERB-α and/or REV-ERB-β, preferably REV-ERB-β. In some embodiments, said compound preferably decreases the activity of REV-ERB-α and REV-ERB-β. Said compound may be a REV-ERB antagonist, preferably an antagonist of REV-ERB-α and REV-ERB-β. Said compound may be selected from a small molecule, a PROTAC reagent, a double stranded RNA (dsRNA), a small interfering RNA (siRNA), a small hairpin RNA (shRNA), a micro RNA, an antisense RNA, an aptamer, an antibody, a ribozyme, a peptide or a peptidomimetic. In some embodiments, preferably the compound is a small molecule. The compound may be SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino) methyl)-2-((4-methylpiperazin-1-yl)methyl)phenol, 1-(2-fluorophenyl)-N-(3-((1-methylpiperidin-4-yl)methyl) benzyl)cyclopentan-1-amine or 1-(4-fluorophenyl)-N-(3-((1-methylpiperidin-4-yl)methyl)benzyl)cyclopentan-1-amine, preferably SR8278. The compound may be added no later than 2 days after isolating the HPCs in the sample, and optionally the Notch ligand is present on or from 4 days after isolating said HPCs.

The invention further provides an ex vivo method for expanding an Natural Killer (NK) cell population, comprising: a) culturing an haematopoietic progenitor cell (HPC) comprising sample obtained from an individual in the presence of a delta-like ligand 4 (DLL4), or a fragment thereof which retains the function of DLL4, or a molecule which mimics the activity/function of DLL4; and b) culturing the cells produced by step (a) in the presence of IL-15; thereby producing an expanded NK cell population. The vessel in which the HPCs are cultured in step (a) may be coated with the DLL4 ligand or fragment thereof. In some embodiments, in step (a) the HPCs are also cultured in the presence of IL-7, Flt3L and/or stem cell factor (SCF), preferably IL-7, Flt3L and SCF. Step (a) and/or step (b) may be carried out in the absence of a stromal support cell, in some preferred embodiments both step (a) and step (b) are carried out in the absence of a stromal support cell.

The sample of HPCs is obtained from bone marrow, cord blood and/or peripheral blood.

The invention also provides an expanded NK cell population obtained by the method of any the invention, wherein at least 85% of the NK cells are CD56+ and CD45+.

The invention further provides a composition comprising an expanded NK cell population of the invention and a pharmaceutically acceptable carrier, diluent and/or excipient.

The invention further provides products containing a compound which inhibits the action of REV-ERB and a Notch ligand as a combined preparation for simultaneous, separate or sequential use in a method of therapy by increasing production of natural killer (NK) cells in a patient. In some embodiments: a) said compound is a compound as defined herein; and/or b) said Notch ligand is delta-like ligand 4 (DLL4), a fragment thereof which retains the function of DLL4, or a molecule which mimics the function/ activity of DLL4. Said method of therapy may be a method of treating a disease or disorder selected from cancer, an infectious disease (acute or chronic), an autoimmune disease or a disease or disorder related to female infertility or pregnancy. Said method of therapy may be a method of treatment of a viral infection, a bacterial infection, a protest infection, a fungal infection and/or a helminth infection. The productions for use of the invention may be used in combination with antibody-mediated immunotherapy. In some embodiments of the products for use of the invention, said compound and/or Notch ligand is for administration before, simultaneously with, or after administration of the antibody-mediated immunotherapy. Said compound may be SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino) methyl)-2-((4-methylpiperazin-1-yl)methyl)phenol, 1-(2-fluorophenyl)-N-(3-((1-methylpiperidin-4-yl)methyl) benzyl)cyclopentan-1-amine or 1-(4-fluorophenyl)-N-(3-((1-methylpiperidin-4-yl)methyl)benzyl)cyclopentan-1-amine, preferably SR8278.

The invention also provides a method of treatment by increasing the number of NK cells in a patient in need thereof, comprising administering to said patient a therapeutically effective amount of a compound which inhibits the action of REV-ERB (as defined herein) and a Notch ligand. The Notch ligand may be delta-like ligand 4 (DLL4), or a fragment thereof which retains the function of DLL4. In such methods, the compound and Notch ligand may be used in combination with antibody-mediated immunotherapy.

The invention further provides an ex vivo method for expanding an NK cell population, comprising the steps of: a) culturing an HPC comprising sample obtained from an individual; b) contacting said sample with a compound which results in the post-translational modification of E4bp4, thereby causing an increase in E4bp4 activity; and c) expanding said cells in vitro to produce an NK cell population. Said post-translation modification of E4bp4 is typically a reduction in SUMOylation and/or phosphorylation of E4bp4. In some embodiments, the compound: a) reduces SUMOylation at one or more of residues K10, K116, K219, K337 and/or K394 of E4bp4, or a residue corresponding thereto, or any combination thereof; and/or b) reduces phosphorylation at one or more of residues S286, S301 and/or S454, or a residue corresponding thereto, or any combination thereof.

DETAILED DESCRIPTION OF THE INVENTION

Natural Killer Cells

Natural Killer (NK) cells exhibit the highest level of cytotoxic activity within the immune system. NK cells are similar to B cells and T cells, but lack specific cell surface antigen receptors. Instead, NK cells have activatory and inhibitory receptors that recognise motifs.

NK cells circulate in the blood and the peripheral lymphoid organs such as lymph nodes and spleen. They can become activated by cytokines or upon encountering target cells. The recognition and elimination of target cells is based on balancing between inhibitory and activatory signals. Activatory signals are generated by activatory receptors (NKG$_2$D, NKp$_{46}$, NKp$_{30}$) binding to ligands, which can be present not only on cancerous, pathogen-infected and damaged cells, but also on healthy cells. On the other hand, inhibitory signals are generated when inhibitory receptors (KIR, CD$_{94}$/NKG$_2$A) on NK cells bind to Major Histocompatability Complex (MHC) Class I molecules that are normally present on all healthy cells. MHC Class I molecules on target cells are absent or greatly downregulated, making them ideal NK cell targets. This allowed NK cells to distinguish between target and healthy cells. In order for NK cells to recognise and kill target cells, overall activatory signals must be greater than inhibitory signals.

NK cells recognise and kill cancerous, pathogen-infected and damaged cells without prior sensitisation, making them part of the innate immune response. For example, NK cells provide an early response to virus infection, occurring prior to T cell killing of infected cells. NK cells can kill target cells within minutes. NK cells also secrete cytokines and "weaponise" other parts of the immune system. For example, NK cells promote T cell effector function and enhance antibody-directed cellular cytotoxicity (ADCC).

Figure 1:
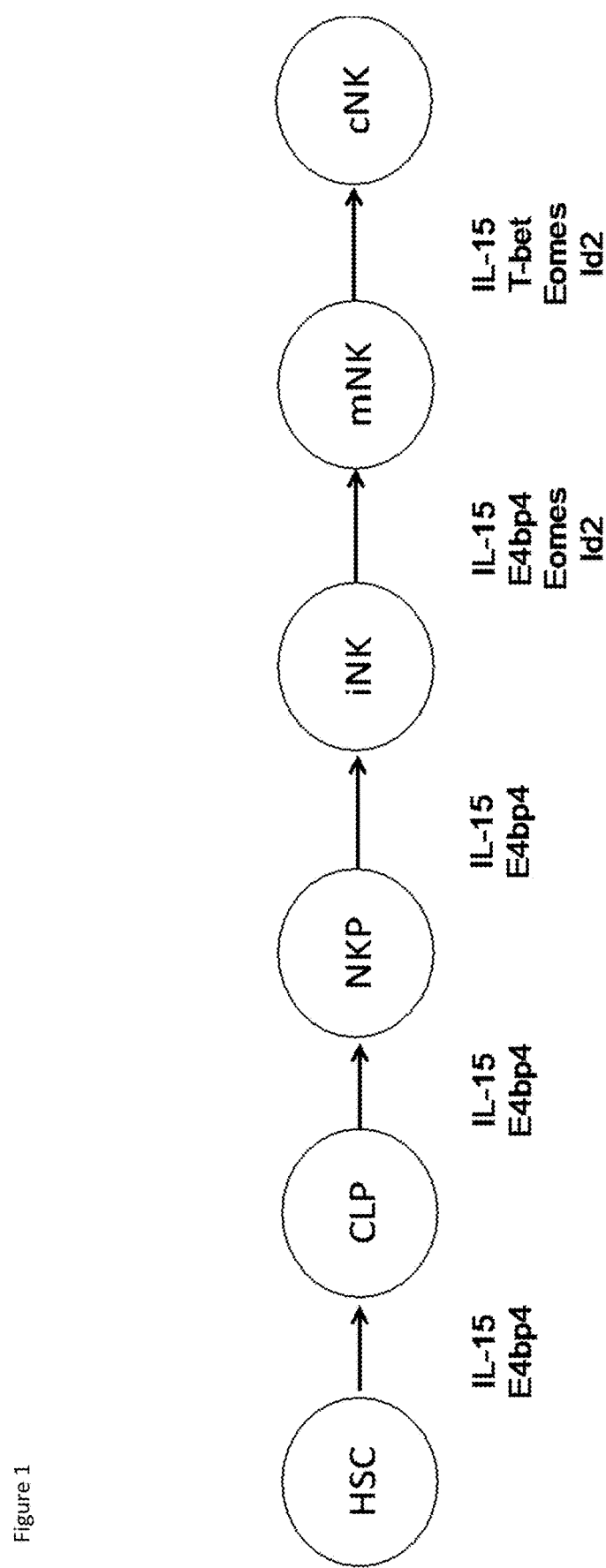
FIG. 1: NK cell developmental pathway. NK cells are differentiated from Hematopoietic Stem Cells (HSCs). NK cells develop from HSC into Common Lymphoid Progenitor (CLP) cells, NK progenitor (NKP) cells, immature NK (iNK) cells, mature NK (mNK) cells and finally into conventional NK (cNK) cells, which circulate in the bloodstream. Below the diagram of the pathway are the cytokines and transcription factors that are required for NK cell development. IL-15 is one of the main cytokine required for the development of NK cells. Others are transcription factors required for the transitions shown on the diagram.

NK cells are differentiated from haematopoietic stem cells (HSCs) via the pathway set out in FIG. 1. In more detail, NK cells develop from HSCs into Common Lymphoid Progenitor (CLP) cells, pre-NK progenitor (pre-NKP) cells, NK progenitor (NKP) cells, immature NK (iNK) cells, mature NK (mNK) cells and finally into conventional NK (cNK) cells, which circulate in the bloodstream. Although this terminology derives from NK cell development in mice, a corresponding pathway occurs in human NK cell development. For example, HSCs develop through multiple stages of precursors (stage 1, 2 and 3), before developing into mature NK cells (stages 4 and 5). For consistency, references HSCs, CLPs, pre-NKPs, NKPs, iNK, mNK, cNK and NK cells are used herein. However, in the context of the present invention, these terms are interchangeable with stages 1 to 5 of the human nomenclature. Below the diagram of the pathway in FIG. 1 are the cytokines and transcription factors that are essential for NK cell development. IL-15 is one of the main cytokine required for the development of NK cells. Other extrinsic factors, such as specific stromal cells, are also required for the development and maturation of NK cells. According to the present invention, Hematopoietic Progenitor Cells (HPCs) are a heterogeneous population containing multi-potential progenitors such as HSCs, CLPs and also NKPs. HPCs are referred to as lineage negative cells, as they have not yet committed to a developmental pathway. Accordingly, in the context of the present invention, HSCs, CLP cells and NKP cells are all HPCs and a reference to HPCs is a reference to any of HSCs, CLP cells and/or CLP cells, or any combination thereof, unless explicitly stated to the contrary.

Due to the importance of NK cells in immune response, multiple clinical trials have tested the efficacy of NK cells in adoptive transfer protocols. Typically this is allogenic transfer, with the NK cells being isolated from a healthy donor and expanded. However, the downregulation of MHC Class I molecules on target cells is partial and the KIR genotype from donors and recipients may be similar. Due to this, NK cells transfused into recipients, even from different individuals may not attach target cells if their KIRs recognise MHC Class I molecules. Therefore, it is crucial that NK cell donors must be screened for their KIR genotype, where the donor must have the appropriate KIR allelic polymorphism to the recipient to allow recognition of target cells for destruction. Moreover, the expanded products were found to have lower clinical success rate than expected, with less ability to kill cancerous or infected cells.

An NK cell may be defined in terms of its marker expression, its function/activity, or a combination thereof. Such definitions are standard in the art and methods are known by which marker expression and/or NK cell activity may be assessed. Thus, one of skill in the art would readily be able to categorise a cell as an NK cell using standard methodology and definitions.

For example, mNK and cNK cells may be recognised by their expression of the surface markers CD16 (FcγRIII) and/or CD56, typically both CD16 and CD56 in humans, and NK1.1 or NK1.2 in some mice strains. NKp46 is another marker for mNK and cNK cells, and is expressed in humans and several mice strains. Thus, NKp46 may be used as a marker for NK cells either with or without CD16 and/or CD56 (in humans) or with or without NK1.1 or NK1.2 (in mice). Other examples of makers which can be used to identify/define NK cells according to the present invention include Ly49, natural cytotoxicity receptors (NCRs), CD94, NKG2, killer-cell immunoglobulin-like receptors (KIRs), and/or leukocyte inhibitory receptors (ILT or LIR), or any combination thereof, including in combination with CD16 and or CD56 (in humans) or NK1.1/NK1.2 (in mice). In some preferred embodiments mature NK cells according to the invention (i.e. mNK and cNK cells) are CD56+ and CD45$^+$, and may be also be CD16$^+$. As used herein, the term mature human NK cell encompasses NK cells that are CD56$^{bright}$ (stage 4) and CD56$^{dim}$ (stage 5), both of which are CD56$^+$. Mature NK cells may also be defined by the absence of markers, such as CD34, and lymphocyte markers CD3 and/or CD19. Thus, mature NK cells of the invention may be CD56$^+$, CD45$^+$, CD16$^+$, CD3$^-$ and/or CD19$^-$, or any combination thereof, such as CD56$^+$, CD45$^+$, CD16$^+$, CD3$^-$ and CD19$^-$.

In addition or alternatively, an NK may be identified by/defined in terms of its activity. For example, an NK cell may be identified/defined by the presence of cytolytic granules within its cytoplasm, by its ability to secrete antimicrobial molecules such as α-defensins, and/or its ability to secrete cytokines such as TNF-α, IL-10, IFN-γ and TFG-β.

Unless otherwise stated herein, a reference to NK cells includes a reference to iNK, mNK and cNK cells. HSCs, CLP cells and NKPs will typically be referred to as such.

Expanded NK Cell Populations

As disclosed herein, the invention provides methods for generating an expanded population of NK cells (referred to interchangeably herein as an expanded NK cell population or an NK cell population). Any of the disclosure herein in relation to NK cells of the present invention may also be applied to an expanded NK cell population of the invention.

Accordingly, the present invention provides an expanded NK cell population. Typically an expanded NK cell population of the invention comprises iNK cells, mNK cells and/or cNK cells, or a combination thereof. Said population may comprise HPCs, such as HSCs, CLP cells and/or NKPs, or a combination thereof, although the numbers of such cells is typically low relative to the number of NK cells, as the majority of these HPCs have differentiated into NK cells in the population. Said population may comprise other immune and/or non-immune cells. Again, the number of any such cells is typically low relative to the number of NK cells present in the population.

As a non-limiting example, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention may be NK cells. Typically at least 80%, preferably at least 85%, more preferably at least 90%, or even more preferably at least 95% of the cells of an expanded NK cell population of the invention are NK cells.

In some embodiments, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention are mature NK cells (i.e. mNK cells and/or cNK cells). Preferably at least 80%, more preferably at least 85%, even more preferably at least 90%, even more preferably at least 95%, even more preferably at least 98% or more of the cells of an expanded NK cell population of the invention are mature NK cells.

The number of HPCs (including HSCs, CLP cells and/or NKPs) may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of HPCs (including HSCs, CLP cells and/or NKPs) is less than 20%, preferably less than 15%, more preferably less than 10%, even more preferably less than 5%, even more preferably less than 2% or less of the cells of the expanded NK cell population.

The number of other immune and/or non-immune cells may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of other immune and/or non-immune cells is less than 20%, preferably less than 15%, more preferably less than 10%, even more preferably less than 5% of the cells, even more preferably less than 2%, or less of the expanded NK cell population.

As described herein, the expanded NK cell populations made by the methods of the present invention offer several advantages over NK cell populations made by conventional adoptive transfer methods. In particular, the methods of the present invention enable the production of expanded populations with greater number of NK cells compared with conventional methods. Further, a greater proportion of the NK cells in a population of the invention are functional, preferably fully functional, compared with populations obtained by conventional methods, in which a large number of the NK cells are "exhausted".

As used herein, the term "exhausted" in the context of NK cells means that an NK cell or expanded NK cell population has lost at least some of its effector functions, such as cytotoxic function, cytokine production and/or ADCC. Thus, an exhausted NK cell or expanded NK cell population may exhibit impaired survival, impaired cytotoxic function, altered or impaired cytokine production and/or impaired ADCC. For example, an exhausted NK cell or exhausted NK cell population may exhibit at least a 50% reduction in one of its effector functions. For example, at least a 50% reduction in cytokine secretion, at least a 50% reduction in ADCC and/or at least 50% reduction in cytotoxic activity. These values may be quantified relative to any appropriate control as defined herein. Any appropriate technique can be used to determine effector function, and hence to quantify and reduction therein. Suitable techniques are known in the art. Alternatively and/or in addition, exhausted NK cells may exhibit altered marker expression, such as an increase in the expression of one or more inhibitory receptor (as described herein) and/or a decrease in the expression of one or more activatory receptor (as described herein). In some embodiments, increased expression of NKG2A and/or Tim3 may be used as a marker for NK cell exhaustion. Again, the expression of these markers may be quantified relative to any appropriate control as defined herein.

In contrast, the terms "functional" and "fully functional" in the context of NK cells means that an NK cell or expanded NK cell population has all of the expected effector functions when responding to a given immune challenge. Thus, a (fully) functional NK cell or expanded NK cell population will typically exhibit cytotoxic function, cytokine production and/or ADCC as would be observed in vivo when NK cells are activated in response to an immune challenge, and will typically exhibit enhanced survival compared with NK cells produced using conventional methods. Alternatively and/or in addition, (fully) functional NK cells may exhibit altered marker expression, such as an increase in the expression of one or more activatory receptor (as described herein) and/or a decrease in the expression of one or more inhibitory receptor (as described herein). As a non-limiting example, a functional (mature) human NK cell may be CD56$^+$ and/or CD45$^+$, preferably both CD56$^+$ and CD45$^+$.

As a non-limiting example, the cytotoxicity of NK cells can be determined using a degranulation assay in NK cells co-incubated with 'target cells'. A degranulation assay involves analysing the expression of CD107a within the NK cell population. The amount of CD107a correlates with cytokine secretion and NK cell-mediated lysis of target cells. NK cells can also be analysed for the expression of Interferon-γ (IFN-γ), which is the main cytokine secreted when functional NK cells are activated. NK cells that are functional should express similar or higher CD107a as well as IFN-γ when compared to a control.

Any increase in NK cell number/functionality in an expanded NK cell population made by a method of the present invention may be compared with the NK cell number/function of an NK cell population obtained from a control method as described herein. A control method may be any standard method known in the art for producing NK cell populations. For example, a control method may use conventional adoptive transfer techniques, rather than a method using a REV-ERB inhibitor according to the present invention. NK cells and NK cell populations produced by such control/standard methods may be used as control cells and populations as described herein.

As an expanded NK cell population of the present invention comprises significantly fewer exhausted NK cells compared to conventionally prepared NK cell populations, but instead contains a higher proportion of fully functional NK cells, this advantageously allows the use of smaller numbers of cells to treat patients.

As described herein, the methods of the invention produce expanded NK cell populations with a higher proportion of (fully) functional NK cells compared with conventional methods, which produce populations with large numbers of "exhausted" NK cells. Typically, in an expanded NK cell population of the invention at least 50%, at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more, up to 100% of the NK cells of an expanded NK cell population of the invention are (fully) functional. Typically at least 80%, preferably at least 85%, more preferably at least 90%, even more preferably at least 95%, even more preferably at least 98% or more of the NK cells of an expanded NK cell population of the invention are fully functional, according to any definition (e.g. marker and/or effector function definition) herein.

An expanded NK cell population of the invention may be produced by any of the methods disclosed herein. Typically an expanded NK cell population of the invention is produced by an ex vivo method as disclosed herein.

Notch Ligand

The Notch signalling pathway is primarily associated with promoting T cell development and repressing concomitant B cell development. Mammals have four types of Notch receptor—Notch1, Notch2, Notch3 and Notch4, all of which are single-pass heterodimeric transmembrane protein. Mammals have two types of canonical Notch ligands—Delta type and Jagged type, collectively known as DSL ligands. There are three delta-like ligands (DLLs), DLL1, DLL3 and DLL4 and two jagged (JAG) ligands, JAG1 and JAG2. DLL and JAG ligands typically comprise the following domains: a module at the N-terminus of Notch ligand (MNNL) domain and a Delta/Serrate/Lag-2 (DSL) domain, together with a number of EGF repeats. DLL3 comprises six EGF repeats. DLL1 and DLL4 comprise eight EGF repeats. JAG1 and JAG2 comprise 16 EGF repeats. There are also numerous non-canonical ligands, which may be membrane-bound or secreted.

Unless explicitly stated herein, a reference herein to a Notch ligand is a reference to any Notch ligand, such as a ligand of Notch1, Notch2, Notch3 and/or Notch 4, preferably a ligand of at least Notch1. The protein sequence of human Notch1 is given in SEQ ID NO: 51 (GenBank Accession No. CR457221, version CR457221.1). Typically the Notch ligand of use in the present invention is a canonical Notch ligand. In some preferred embodiments, the Notch ligand is a DLL, more preferably DLL4. The protein sequence of human DLL4 is given in SEQ ID NO: 2 (GenBank Accession No. AF253468, version AF253468.1).

A reference herein to a Notch ligand also embraces fragments thereof, provided said fragment retains the Notch-binding and activatory activity of the Notch ligand from which it is derived. As a non-limiting example, a Notch ligand fragment of the invention may comprise or consist of 170 consecutive amino acid residues or more in length (e.g. at least 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, or more consecutive amino acid residues in length, up to the total length of the Notch ligand, such as DLL4. Typically a functional fragment of a Notch ligand comprises at least 50%, at least 55%, at least 60%, at least 65%, at least 66%, at least 67%, at least 68%, at least 69%, at least 70% or more of the full-length Notch ligand, such as DLL4. As a non-limiting example, a fragment of a Notch ligand may comprise the MNNL domain and/or the DSL domain of said Notch ligand, such as DLL4. In some preferred embodiments, the Notch ligand fragment comprises (or consists of) both the MNNL and DSL domains of a Notch ligand of interest, such as the MNNL and DSL domains of DLL4. Examples of such fragments include, but are not limited to the following: (i) a Notch ligand fragment comprising or consisting of the portion of a Notch ligand of interest starting at the N-terminus and terminating at the end of the first EGF repeat, otherwise referred to as Notch Ligand (N-EGF1), such as DLL4 (N-EGF1); (ii) a Notch ligand fragment comprising or consisting of the portion of a Notch ligand of interest starting at the N-terminus and terminating at the end of the second EGF repeat, otherwise referred to as Notch Ligand (N-EGF2), such as DLL4 (N-EGF2); (iii) a Notch ligand fragment comprising or consisting of the portion of a Notch ligand of interest starting at the N-terminus and terminating at the end of the third EGF repeat, otherwise referred to as Notch Ligand (N-EGF3), such as DLL4 (N-EGF3); (iv) a Notch ligand fragment comprising or consisting of the portion of a Notch ligand of interest starting at the N-terminus and terminating at the end of the fourth EGF repeat, otherwise referred to as Notch Ligand (N-EGF4), such as DLL4 (N-EGF4); (v) a Notch ligand fragment comprising or consisting of the portion of a Notch ligand of interest starting at the N-terminus and terminating at the end of the fifth EGF repeat, otherwise referred to as Notch Ligand (N-EGF5), such as DLL4 (N-EGF5); (vi) a Notch ligand fragment comprising or consisting of the portion of a Notch ligand of interest starting at the N-terminus and terminating at the end of the sixth EGF repeat, otherwise referred to as Notch Ligand (N-EGF6), such as DLL4 (N-EGF6); or (vii) a Notch ligand fragment comprising or consisting of the portion of a Notch ligand of interest starting at the N-terminus and terminating at the end of the seventh EGF repeat, otherwise referred to as Notch Ligand (N-EGF7), such as DLL4 (N-EGF7). By way of comparision, the full-length DLL4 may be referred to as DLL4 (N-EGF8). Preferred examples of Notch ligand fragments include Notch ligand (N-EGF1) and Notch ligand (N-EGF2), such as DLL4 (N-EGF1) and DLL4 (N-EGF2).

Alternatively or in addition, a Notch ligand, fragment thereof, or molecule that mimics the effect (e.g. function/activity) of a Notch ligand, such as DLL4 may comprise modifications, such as amino acid mutations which alter, typically increase, the affinity of the ligand/fragment/mimetic for its Notch receptor. Techniques for identifying such modifications are known in the art. For example, amino acids which increase the affinity of a Notch ligand/fragment/mimetic can be identified using yeast surface display. As a non-limiting example, in instances where the Notch ligand of interest is DLL4, the DLL4 ligand of the invention, a fragment or mimetic thereof may comprise an amino acid substitution at one or more of the following positions: (G)28, (F)107, (N)118, (I)143, (H)194, (L)206 and/or (K)215, or any combination thereof. In some preferred embodiments, the DLL4 ligand of the invention, a fragment or mimetic thereof comprises amino acid substitutions at positions (G)28, (F)107, and (L)206, more preferably at positions (G)28, (F)107, (N)118, (I)143, (H)194, (L)206 and (K)215. As a further non-limiting example, in instances where the Notch ligand of interest is DLL4, the DLL4 ligand of the invention, a fragment or mimetic thereof may one or more of the following amino acid substitutions G28S, F107L, N118I, I143F, H194Y, L206P and/or K215E, or any combination thereof. In some preferred embodiments, the DLL4 ligand of the invention, a fragment or mimetic thereof comprises the amino acid substitutions, G28S, F107L and L206P, more preferably G28S, F107L, N118I, I143F, H194Y, L206P and/or K215E.

As a further non-limiting example, a functional fragment of DLL4 comprises at least residues 65 to 114 and 179 to 219 of full-length DLL4, preferably held in the correct conformation to allow interaction with the Notch ligand.

In addition, the invention encompasses the use of molecules that would mimic the effect (e.g. activity/function) of a Notch ligand (also referred to herein as mimetics). For example, the use of peptides, stapled peptides, peptoids and peptidomimetics that would mimic the effect of the desired Notch ligand (such as DLL4) is embraced by the present invention. Methods for producing synthetic peptides and peptidomimetics (such as peptoids) are known in the art, as are the sequences of canonical and non-canonical Notch ligands. Thus, it would be routine for one of skill in the art to produce suitable molecules which mimic the effect of a desired Notch ligand using known techniques and based on the known Notch ligand sequences. As a non-limiting example, peptidomimetics may be designed to interact with key residues of Notch (e.g. Notch1) that are known to be involved in binding to DLL4, such as one or more of residues 415 (E415), 418 (L418), 420 (A420), 421 (N421), 422 (P422), 424 (E424), 425 (H425), 436 (F436), 447 (P447), 448 (R448), 450 (E450), 452 (D452), 469 (D469), 477 (I477), 480 (P480) of Notch (Notch1), or any combination thereof.

Peptidomimetics are described herein in relation to REV-ERB inhibitors. That disclosure applies equally and independently to peptidomimetics of Notch ligands.

The methods of the invention may encompass the use of any Notch ligand or fragment thereof which is capable of increasing NK cell production or molecule which mimics the effects thereof, particularly which may act synergistically with a compound of the invention which inhibits REV-ERB activity as disclosed herein, or a compound which results in the post-translational modification of E4bp4, and hence an increase in E4bp4 activity as disclosed herein.

The present inventors have shown that E4bp4 directly binds to the regulatory region of the Notch1 gene in vivo and so could enhance the transcriptional regulation of Notch, and that Notch1 expression E4bp4$^{-/-}$ mice is significantly reduced. Following on from this, the present inventors found that short-term exposure of Notch ligands to murine HSCs and very early progenitors can promote NK cell development, even in the absence of the critical transcription factor E4bp4. Further, the present inventors have shown that the Notch ligand Delta-like ligand 4 (DLL4) is particularly effective in stimulating the expansion of NK cells.

Accordingly, the present invention relates to the expansion of NK cells by exposure of the HPCs to a Notch ligand. In ex vivo or in vitro methods of the invention, this can comprise culturing the HPCs in the presence of a Notch ligand. For in vivo methods, this may comprise administering the compound together with a Notch ligand. In preferred embodiments, the Notch ligand is DLL4, or a fragment or variant thereof which retains the function of DLL4.

In some embodiments, the methods of the invention comprise exposing the HPCs to DLL4, or a fragment or variant thereof which retains the function of DLL4. For example, in the ex vivo or in vitro methods of the invention, the HPCs may be cultured in the presence DLL4, or a fragment or variant thereof which retains the function of DLL4. For the ex vivo and in vitro methods of the invention, an increase in NK cell expansion can be achieved by coated the vessel in which the HPCs are cultured (i.e. the culture vessel) with the Notch ligand, such as DLL4 or a functional fragment or variant thereof.

Variant sequences are described herein in relation to REV-ERB inhibitors. That disclosure applies, inter alia, equally and independently to variants of Notch ligands and fragments/mimetics thereof. The variant Notch ligands/fragments/mimetics of the invention typically at least retain the activity of the corresponding Notch ligands/fragments/mimetics of the invention. Thus, for example, the variant DLL4 ligands or fragments thereof of the invention retain the ability of the corresponding DLL4 molecules to bind to Notch1, and/or to enhance NK cell production. Thus, the variant DLL4 ligands/fragments/mimetics may retain at least 50%, at least 60%, at least 70%, at least 80%, at least 90%, up to and including 100% of the activity of the unmodified DLL4 ligands/fragments/mimetics of the invention. In some embodiments, the variant DLL4 ligands/fragments/mimetics have greater activity than the corresponding unmodified DLL4 ligand/fragment/mimetic. For example, at least 110%, at least 120%, at least 130%, at least 140%, at least 150%, at least 175%, at least 200%, at least 250%, at least 300%, at least 400%, at least 500%, at least 600%, at least 700%, at least 800%, at least 900% or more activity compared with the corresponding unmodified DLL4 ligand/fragment/mimetic. For example, the variant DLL4 ligands/fragments/mimetics may have a $K_D$ value for binding to Notch1 that is at least 10-fold lower, at least 15-fold lower, at least 20-fold lower, at least 25-fold lower, at least 30-fold lower, or less than the corresponding unmodified DLL4 ligand/fragment/mimetic. E.g., the variant DLL4 ligands/fragments/mimetics may have a $K_D$ value for binding to Notch1 of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM or less, preferably less than 500 nM, less than 400 nM, less than 300 nM or less. In some embodiments, the variant DLL4 ligands/fragments/mimetics can increase the number of NK cells, or give rise to an increase in NK cell production, of at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 3 fold or more relative to the corresponding unmodified DLL4 ligand/fragment/mimetic. The variant DLL4 ligands/fragments/mimetics may increase number of NK cells by at least 10%, at least 20%, at least 30%, at least 40%, at least 50%, at least 60, at least 70%, at least 80%, at least 85%, at least 90%, at least 95%, at least 100%, at least 150%, at least 200%, at least 300% or more compared with the corresponding unmodified DLL4 ligand/fragment/mimetic. This applies equally to any variants of the other Notch ligands/fragments/mimetics of the invention.

The Notch ligands/fragments/mimetics of the invention may be labelled (or tagged). Any appropriate label may be used. Suitable labels are known in the art.

E4bp4

E4bp4 (also known as Nfil3) is a basic leucine zipper protein transcription factor which is involved in the regulation of IL-3 expression, and is involved in the coordinating the circadian clock. The genomic DNA sequence of the human E4bp4 gene is given in SEQ ID NO: 3 (Genbank Accession No. X64318, version X64318.1). As shown in FIG. 1, E4bp4 is expressed in CLPs and is critical in the production of NK cells from blood stem cell progenitors. Mice with the E4bp4 gene deleted do not have functional NK cells, but have normal numbers of T and B cells. In contrast, overexpression of E4bp4 in HSCs in vitro increases NK cell production. Thus, E4bp4 is a lineage commitment factor, controlling the development of NKPs from HSCs (FIG. 1). E4bp4's critical function in NK cells is specific to the early stages of the developmental pathway, as specific ablation of E4bp4 in peripheral mNK cells does not affect NK cell number or response to cytomegalovirus infection. In addition E4bp4 regulates other transcription factors that are essential in NK cell development, such as Id2 and Eomes.

Although IL-7 and IL-15 have been shown to regulate E4bp4 expression, generally very little is known about how either extrinsic or intrinsic stimuli influence E4bp4. Transcription factors such as E4bp4 can be hard to target because of their structure and function. For example, they usually lack enzymatic activity or cofactor binding sites. The present inventors have previously demonstrated that E4bp4 expression can be increased using a compound which inhibits the activity of REV-ERB, and that this results in an increase in NK cell number (see GB Application No. 1703476.0, which is herein incorporated by reference in its entirety). Without wishing to be bound by theory, REV-ERB binds to porphyrin heme, and it is this characteristic that is believed to make REV-ERB a druggable target (see below). In sum, the inventors have shown that by targeting REV-ERB and inhibiting its activity, it is possible to increase E4bp4 expression and hence increase NK cell number. Accordingly, the present invention is concerned with compounds which inhibit the action of REV-ERB, and their use in increasing E4bp4 expression, and hence NK cell number.

Increase in E4bp4 Expression

Accordingly, the present invention provides ex vivo methods for producing expanded NK cell populations, and therapeutic methods and applications for increasing NK cell number in a patient in need thereof. As disclosed herein, said methods and applications may involve the use of a compound which inhibits the action of REV-ERB. Typically said compounds act by increasing E4bp4 expression.

An increase in E4bp4 expression may be measured relative to a control. Thus, the expression of E4bp4 in a sample of HPCs, an expanded NK cell population or in a sample obtained from an individual/patient to be treated according to the invention may be compared with the expression of E4bp4 in a control. Expression may be quantified in terms of gene and/or protein expression, and may be compared with expression of a control (e.g. housekeeping gene or protein). The actual amount of the E4bp4 gene, mRNA transcript and/or protein, such as the mass, molar amount, concentration or molarity of the E4bp4 gene, mRNA transcript and/or protein, or the number of mRNA molecules per cell in a sample of HPCs, an expanded NK cell population or in a sample obtained from an individual/patient to be treated according to the invention and the control may be assessed and compared with the corresponding value from the control. Alternatively, the expression of the E4bp4 gene and/or protein in a sample of HPCs, an expanded NK cell population or in a sample obtained from an individual/patient to be treated according to the invention may be compared with that of the control without quantifying the mass, molar amount, concentration or molarity of the one or more gene and/or protein.

Typically the control is an equivalent population or sample in which no increase in E4bp4 expression has been effected. As a non-limiting example, in the case where an individual/patient is treated with a compound that inhibits REV-ERB activity in order to increase E4bp4 expression, a suitable control would be a different individual to which the compound has not been administered or the same individual prior to administration of the compound. Conventional methods for the ex vivo expansion of NK cells, including known methods may be considered control methods according to the present invention.

In the context of the present invention, a reference to increasing E4bp4 expression may be understood to mean that, the expression of E4bp4 is increased by at least 10%, at least 20%, at least 30%, at least 40%, at least 50%, at least 60, at least 70%, at least 80%, at least 85%, at least 90%, at least 95%, at least 100%, at least 150%, at least 200% compared with the control. Typically E4bp4 expression is increased by at least 50%, preferably at least 70%, more preferably at least 80%, even more preferably at least 90% or more compared with the control.

A reference to increasing E4bp4 expression may be understood to mean that, the expression of E4bp4 is increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically E4bp4 gene expression is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control. Typically E4bp4 protein expression is increased by at least 2-fold, at least 3-fold, preferably at least 5-fold, more preferably at least 6-fold or more compared with the control.

The expression of the E4bp4 gene and/or protein according to the invention may be determined by quantitative and/or qualitative analysis. Typically, gene expression may be expressed in terms of mRNA levels.

The expression level of the E4bp4 gene and/or protein according to the invention encompasses the mass of the E4bp4 mRNA transcript and/or protein, the molar amount of the E4bp4 gene, mRNA transcript and/or protein, the concentration of the E4bp4 gene and/or protein and the molarity of the E4bp4 gene and/or protein. This expression level may be given in any appropriate units. For example, the concentration of the E4bp4 gene and/or protein may be given in pg/ml, ng/ml or µg/ml.

The expression level of the E4bp4 gene and/or protein according to the invention may be measured directly or indirectly.

The relative expression of the E4bp4 gene and/or protein according to the invention relative to a control may be determined using any appropriate technique. Suitable standard techniques are known in the art, for example Western blotting, enzyme-linked immunosorbent assays (ELISAs) and RT-qPCR.

The expression level of the E4bp4 gene and/or protein may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the expression level of the E4bp4 gene and/or protein is increased for at least 12 to 72 hours. Typically this is assessed relative to the last administration of the compound which inhibits REV-ERB activity.

The expression level of the E4bp4 gene and/or protein may be increased compared with a control for at least one, at least two, at least three, at least four, at least five, at least ten, at least 20, at least 30, at least 40 or more passages of the NK cell precursors in culture. The expression level of the E4bp4 gene and/or protein may be altered indefinitely.

REV-ERB

REV-ERB proteins are members of the nuclear receptor family of intracellular transcription factors. The mRNA sequence of the human REV-ERBα gene (Nr1d1) is given in SEQ ID NO: 5 (Genbank Accession No. NM_021724, version NM_021724.4). The mRNA sequence of the human REV-ERBβ gene (Nr1d2) is given in SEQ ID NO: 7 (Genbank Accession No. AB307693, version AB307693.1). REV-ERB regulates the circadian clock, and has also been implicated in the regulation of cartilage breakdown.

The present inventors have previously demonstrated that inhibition of REV-ERB activity is sufficient to elicit a significant increase in E4bp4 expression, and that this in turn brings about an expansion of NK cells, resulting in an increase in NK cell number (see GB Application No. 1703476.0, which is herein incorporated by reference in its entirety). Inhibition of REV-ERB activity can bring about an increase in NK cell number, and that typically the resulting NK cells are (fully) functional as defined herein. The effect of REV-ERB inhibition is mediated in an E4pb4-dependent manner. Without wishing to be bound by theory, it is believed that inhibition of REV-ERB activity results in an increase in E4bp4 expression (E4bp4 expression is normally repressed by REV-ERB), and that the E4bp4 acts to stimulate the production of NK cells (as shown in FIG. 1). In particular, the present inventors have previously demonstrated that the small molecule SR8278 is capable of binding to the porphyrin heme moiety of REV-ERB, resulting in inhibition of REV-ERB activity and an increase in NK cell number Accordingly, in some embodiments, the present invention is concerned with compounds which inhibit the action of REV-ERB, and their use in increasing E4bp4 expression, and hence NK cell number.

Inhibition of REV-ERB Activity

In some embodiments, the present invention relates to the use of compounds to inhibit the action of REV-ERB, i.e. compounds which inhibit REV-ERB activity. REV-REB activity may be inhibited by any appropriate means. Suitable standard techniques are known in the art. Inhibition may take place via any suitable mechanism, depending for example on the nature (see below) of the compound used, e.g. steric interference in any direct or indirect interaction or inhibition of REV-ERB. In the context of the present invention a REV-ERB inhibitor (interchangeably referred to herein as a REV-ERB antagonist) is any compound which inhibits, decreases, suppresses or ablates the action of REV-ERB, whether in part or completely.

A decrease in REV-ERB activity may be measured relative to a control. Thus, the activity of REV-ERB in a sample of NK precursor or progenitor cells, an expanded NK cell population or in a sample obtained from an individual/patient to be treated according to the invention may be compared with the activity of REV-ERB in a control. Activity may be quantified in any appropriate terms, for example binding of REV-ERB to the E4bp4 gene, or in terms of E4bp4 expression as defined herein. Any appropriate technique or method may be used for quantifying REV-ERB activity. Suitable techniques are known in the art, for example luciferase assays for quantifying expression of a reporter gene.

Typically the control is an equivalent population or sample in which no REV-ERB inhibitory compound has been added, for example a sample obtained from a different individual to which the compound has not been administered, or the same individual the prior to administration of the compound. Conventional methods for the ex vivo expansion of NK cells, including known methods may be considered control methods according to the present invention.

In the context of the present invention, a reference to inhibiting REV-ERB activity may be understood to mean that, the activity of REV-ERB is decreased by at least 10%, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, up to total (100%) inhibition of REV-ERB activity, as compared with the control. Typically REV-ERB activity is decreased by at least 50%, preferably at least 70%, more preferably at least 80%, more preferably at least 90%, even more preferably at least 95% or more compared with the control.

The activity of REV-ERB may be determined by quantitative and/or qualitative analysis, and may be measured directly or indirectly.

The activity of REV-ERB relative to a control may be determined using any appropriate technique. Suitable standard techniques are known in the art, such as by quantifying E4bp4 expression, and/or luciferase assays.

The activity of REV-ERB may be inhibited compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the activity of REV-ERB is decreased for at least 12 to 72 hours. Typically this is assessed relative to the last administration of the compound which inhibits REV-ERB activity.

The activity of REV-ERB may be inhibited compared with a control for at least one, at least two, at least three, at least four, at least five, at least ten, at least 20, at least 30, at least 40 or more passages of the cells (either in vivo, or cultured ex vivo or in vitro). The activity of REV-ERB may be inhibited and/or the expression level of the E4bp4 gene and/or protein may be altered indefinitely.

In the context of the present invention any reference to inhibiting REV-ERB activity may be understood to mean inhibiting the activity of REV-ERBα and/or REV-ERBβ. In preferred embodiments, the activity of both REV-ERBα and REV-ERBβ is inhibited. Thus, the invention relates to compounds which inhibit REV-ERB activity, including compounds which inhibit REV-ERBα activity (i.e. REV-ERBα inhibitors, also referred to as REV-ERBα antagonists) and/or to compounds which inhibit REV-ERBβ activity (i.e. REV-ERBβ inhibitors, also referred to as REV-ERBβ antagonists). In preferred embodiments, the invention relates to compounds which inhibit the activity of both REV-ERBα and REV-ERBβ (i.e. REV-ERBα and REV-ERBβ inhibitors, also referred to as REV-ERBα and REV-ERBβ antagonists).

REV-ERB Antagonists/Inhibitors

REV-ERB inhibitory compounds of the invention may be specific for REV-ERB. By specific, it will be understood that the compound binds to REV-ERBα and/or REV-ERBβ, with no significant cross-reactivity to any other molecule, particularly any other protein. For example, modulator that is specific for REV-ERBα and/or REV-ERBβ will show no significant cross-reactivity with human neutrophil elastase. Cross-reactivity may be assessed by any suitable method. Cross-reactivity of REV-ERBα and/or REV-ERBβ inhibitor with a molecule other than REV-ERBα and/or REV-ERBβ may be considered significant if the inhibitor binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to REV-ERBα and/or REV-ERBβ. An inhibitor that is specific for REV-ERBα and/or REV-ERBβ may bind to another molecule such as human neutrophil elastase at less than 90%, 85%, 80%, 75%, 70%, 65%, 60%, 55%, 50%, 45%, 40%, 35%, 30%, 25% or 20% the strength that it binds to REV-ERBα and/or REV-ERBβ. Preferably, the inhibitor binds to the other molecule at less than 20%, less than 15%, less than 10% or less than 5%, less than 2% or less than 1% the strength that it binds to REV-ERBα and/or REV-ERBβ.

REV-ERB inhibitory compounds of the invention may have off-target effects. An off-target effect is activity against a target other than REV-ERB. Typically compounds with off-target effects are encompassed by the present invention if the activity against the non-REV-ERB target is not significant compared with the activity against REV-ERB. Whether an off-target effect is significant may depend on the intended use of the compound. As a non-limiting example, a compound which may exert an off-target effect on the central nervous system would not be significant for a compound used in an ex vivo method as disclosed herein, but may be significant (depending on the magnitude of the off-target effect) for an in vivo therapeutic indication as disclosed herein. The presence and magnitude of any potential off target effects can be readily assessed using standard methods known in the art.

Any suitable inhibitor may be used according to the invention, for example small molecules, PROTAC reagents, double stranded RNA (dsRNA), small interfering RNA (siRNA), small hairpin RNA (shRNA), microRNA, antisense (single stranded) RNA, peptides and peptidomimetics, antibodies, aptamers and ribozymes. Preferred inhibitors include small molecules and PROTAC reagents.

Small Molecules

Small molecules may be used to inhibit REV-ERB activity as described herein. As defined herein, small molecules are low molecular weight compounds, typically organic compounds. Typically, a small molecule has a maximum molecule weight of 900 Da, allowing for rapid diffusion across cell membranes. In some embodiments, the maximum molecular weight of a small molecule is 500 Da. Typically a small molecule has a size in the order of 1 nm.

According to the present invention, small molecules may be able to exert an inhibitory effect on REV-ERB activity by binding to the porphyrin heme moiety of REV-ERB. Thus in some preferred embodiments, a compound that inhibits the action of REV-ERB according to the present invention is a compound which binds to the porphyrin heme moiety of REV-ERB, and hence inhibits the activity of REV-ERB. Alternatively, the small molecule may act via a different mechanism, for example, by binding to a non-heme portion of REV-ERB. Standard techniques are known in the art for the production of small molecules, which can then readily be tested for REV-ERB inhibitory activity as described herein

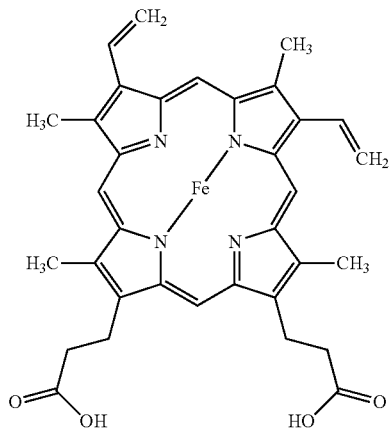

Structure of Porphyrin Heme

In a preferred embodiment, the invention relates to the small molecule 1,2,3,4-Tetrahydro-2-[[5-(methylthio)-2-thienyl]carbonyl]-3-isoquinolinecarboxylic acid ethyl ester, herein referred to as SR8278 as a REV-ERB inhibitor.

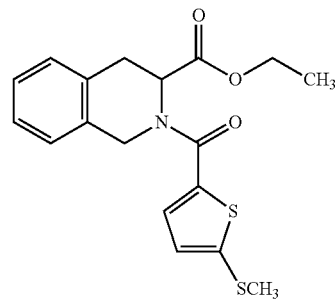 [SMILES: CCOC(=O)C1Cc2ccccc2CN1C(=O)c1ccc(SC)s1]

Structure of SR8278

The invention also encompasses the use of variants of SR8278 which retain the REV-ERB inhibitory function of SR8278.

Any small molecule which exerts an inhibitory effect on REV-ERB activity may be used as a REV-ERB inhibitor according to the present invention. Such small molecule inhibitors may also bind to REV-ERB. Examples of other small molecules which may be used as REV-ERB inhibitors according to the present invention include 4-[[[1-(2-fluorophenyl)cyclopentyl]amino]methyl]-2-[(4-methylpiperazin-1-yl)methyl]phenol (also referred to herein as ARN5187), ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine and 1-(4-fluorophenyl)-N-(3-((1-methylpiperidin-4-yl)methyl)benzyl)cyclopentan-1-amine.

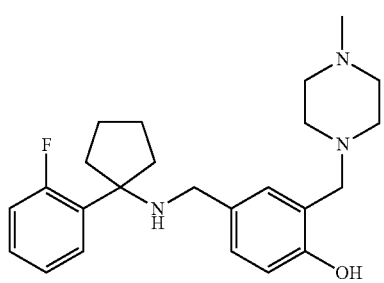 [SMILES: CN1CCN(Cc2cc(CNC3(c4ccccc4F)CCCC3)ccc2O)CC1]

Structure of ARN5187

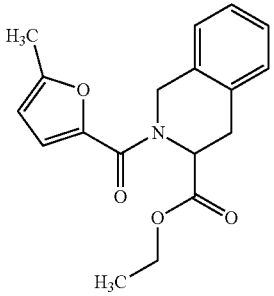 [SMILES: CCOC(=O)C1Cc2ccccc2CN1C(=O)c1ccc(C)o1]

Structure of ethyl 2-(5-methylfuran-2-carbonyl)-1,2,3,4-tetrahydroisoquinoline-3-carboxylate

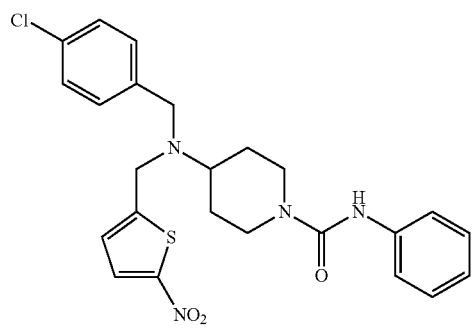 [SMILES: O=C(Nc1ccccc1)N1CCC(N(Cc2ccc(Cl)cc2)Cc2ccc([N+](=O)[O-])s2)CC1]

Structure of 4-((4-chlorobenzyl)((5-nitrothiophen-2-yl)methyl)amino)-N-phenylpiperidine-1-carboxamide

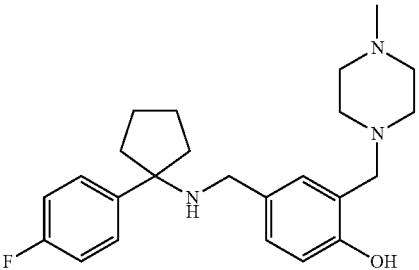 [SMILES: CN1CCN(Cc2cc(CNC3(c4ccc(F)cc4)CCCC3)ccc2O)CC1]

Structure of 4-(((1-(4-fluorophenyl)cyclopentyl)amino)methyl)-2-((4-methylpiperazin-1-yl)methyl)phenol

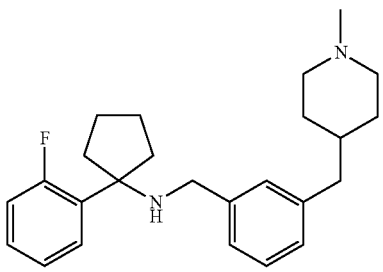 [SMILES: CN1CCC(Cc2cccc(CNC3(c4ccccc4F)CCCC3)c2)CC1]

Structure of 1-(2-fluorophenyl)-N-(3-((1-methylpiperidin-4-yl)methyl)benzyl)cyclopentan-1-amine

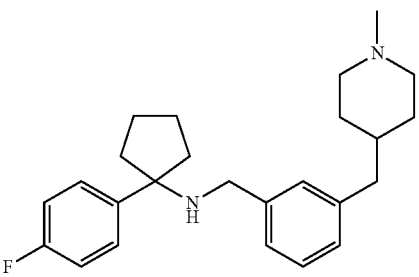 [SMILES: CN1CCC(Cc2cccc(CNC3(c4ccc(F)cc4)CCCC3)c2)CC1]

Structure of 1-(4-fluorophenyl)-N-(3-((1-methylpiperidin-4-yl)methyl)benzyl)cyclopentan-1-amine The invention also encompasses the use of variants of ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine which retain the REV-ERB inhibitory function of ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine respectively.

PROTAC Reagents

Proteolysis targeting chimeras (also referred to as PROTACs or PROTAC reagents) may be used to inhibit REV-ERB activity as described herein. PROTACs are heterobifunctional small molecules that simultaneously bind a target protein and ubiquitin ligase, enabling ubiquitination and degradation of the target. In more detail, a PROTAC reagent typically comprises a ligand for the target protein (in the case of the present invention, REV-ERB) and a ligand for an E3 ligase recognition domain. Through the use of such a PROTAC, an E3 ligase is recruited to the PROTAC-bound REV-ERB, inducing ubiquitin transfer from the E3 ligase complex to the target protein (in the case of the present invention, REV-ERB). Once the PROTAC has induced a sufficient degree of ubiquitination of the target, it is then recognised and degraded by the proteasome.

As a non-limiting example, a PROTAC reagent may be produced by conjugating a ligand for an E3-ligase to a small molecule inhibitor as described herein (preferably SR8278) via a linker. In a preferred embodiment, a PROTAC reagent comprises a ligand for the E3 RING Cullin ligase von-Hippel Lindau protein (VHL) or cereblon—a part of a CRL4 E3 RING Cullin ligase complex, connected to a small molecule inhibitor of the invention via a linker. In some particularly preferred embodiments, the PROTAC reagent comprises a ligand for the E3 RING Cullin ligase von-Hippel Lindau protein (VHL) connected to SR8278, connected via a linker. In other particularly preferred embodiments, the PROTAC reagent comprises cereblon (a part of a CRL4 E3 RING Cullin ligase complex) and SR8278, connected via a linker.

Because of their mechanism of action, PROTAC reagents simply need any ligand for the target protein. The functional pharmacology of the ligand, in the absence of the linker and E3 ligase ligand, is unimportant. Therefore in some embodiments a REV-ERB inhibitory PROTAC reagent of the present invention may comprises a small molecule REV-ERB agonist as the ligand, such as GSK4112 (1,1-Dimethylethyl N-[(4-chlorophenyl)methyl]-N-[(5-nitro-2-thienyl)methyl])glycinate, SR6452).

Double-Stranded RNA

Double-stranded RNA (dsRNA) molecules may be used to inhibit REV-ERB activity as described herein. dsRNA molecules may be used in RNAi to inhibit REV-ERB activity.

Using known techniques and based on a knowledge of the sequence of REV-ERB, dsRNA molecules can be designed to antagonise REV-ERB by sequence homology-based targeting of the corresponding RNA sequence. Such dsRNAs will typically be small interfering RNAs (siRNAs), small hairpin RNAs (shRNAs), or micro-RNAs (miRNAs). The sequence of such dsRNAs will comprise a portion that corresponds with that of a portion of the mRNA encoding REV-ERB. This portion will usually be 100% complementary to the target portion within the mRNA transcribed from the REV-ERB gene, but lower levels of complementarity (e.g. 90% or more or 95% or more) may also be used. Typically the % complementarity is determined over a length of contiguous nucleic acid residues. A dsRNA molecule of the invention may, for example, have at least 80% complementarity to the target portion within the mRNA transcribed from the REV-ERB gene measured over at least 10, at least 20, at least 30, at least 40, at least 50, at least 60, at least 70, at least 80, at least 90, or more nucleic acid residues, up to the dsRNA molecule having at least 80% complementarity the mRNA transcribed from the REV-ERB gene of the invention over the entire length of the dsRNA molecule.

In a preferred embodiment, the dsRNA is a shRNA. ShRNA can be delivered to NK cell precursors by any appropriate means. Suitable techniques are known in the art and include the use of plasmid, viral and bacterial vectors to deliver the shRNA. Typically, the shRNA is delivered using a viral vector delivery system. In a preferred embodiment, the viral vector is a lentiviral vector.

Generally, once the shRNA has been delivered to an NK precursor cell, it is then transcribed in the nucleus and processed. The resulting pre-shRNA is exported from the nucleus and then processed by dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

A variant sequence may have at least 80% sequence identity to an shRNA sequence of the invention, measured over any appropriate length of sequence. Typically the % sequence identity is determined over a length of contiguous nucleic acid or amino acid residues. A variant sequence of the invention may, for example, have at least 80% sequence identity to a sequence of the invention measured over at least 10, at least 20, at least 30, at least 40, at least 50, at least 60, at least 70, at least 80, at least 90, or more nucleic acid or amino acid residues.

For example, a variant shRNA molecule of the invention may have at least 80% sequence identity with an shRNA molecule of the invention measured over at least 10, at least 20, at least 30, at least 40, at least 50, at least 60 or more nucleic acid residues, up to the variant shRNA molecule having at least 80% sequence identity with the shRNA molecule of the invention over the entire length of the variant shRNA molecule.

Antisense RNA

Single-stranded DNA (ssDNA) molecules, also known as antisense RNA, may be used to inhibit REV-ERB activity as described herein.

Using known techniques and based on a knowledge of the sequence of the REV-ERB gene, antisense RNA molecules can be designed to antagonise the REV-ERB gene by sequence homology-based targeting of the corresponding RNA. The sequence of such antisense will comprise a portion that corresponds with that of a portion of the mRNA transcribed from the REV-ERB gene. This portion will usually be 100% complementary to the target portion within the transcribed mRNA but lower levels of complementarity (e.g. 90% or more or 95% or more) may also be used.

Aptamers

Aptamers are generally nucleic acid molecules that bind a specific target molecule. Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

As used herein, "aptamer" refers in general to a single or double stranded oligonucleotide or a mixture of such oligonucleotides, wherein the oligonucleotide or mixture is capable of binding specifically to a target. Oligonucleotide aptamers will be discussed here, but the skilled reader will appreciate that other aptamers having equivalent binding characteristics can also be used, such as peptide aptamers.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by Exponential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579.

The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Peptidomimetics

Peptidomimetics are compounds which mimic a natural peptide or protein with the ability to interact with the biological target and produce the same biological effect. Peptidomimetics may have advantages over peptides in terms of stability and bioavailability associated with a natural peptide. Peptidomimetics can have main- or side-chain modifications of the parent peptide designed for biological function. Examples of classes of peptidomimetics include, but are not limited to, peptoids and β-peptides, as well as peptides incorporating D-amino acids.

Antibodies

Antibodies may be used to inhibit REV-ERB activity as described herein.

As used herein, the term antibody encompasses the use of a monoclonal antibody or polyclonal antibody, as well as the antigen-binding fragments of a monoclonal or polyclonal antibody, or a peptide which binds to REV-ERB with specificity. The antibody may be a Fab, F(ab')2, Fv, scFv, Fd or dAb.

Variant Sequences

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every sequence presented herein and/or to each and every SEQ ID NO presented herein).

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics:1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

Variants of the specific sequences provided above may alternatively be defined by reciting the number of nucleotides or amino acids that differ between the variant sequences and the specific reference sequences provided above. Thus, in one embodiment, the sequence may comprise (or consist of) a nucleotide sequence that differs from the specific sequences provided above at no more than 5, no more than 4, no more than 3, no more than 2 nucleotide positions, for example at no more than 1 nucleotide position. Conservative substitutions are preferred.

The variant nucleic acid molecules and peptides of the invention typically still retain the activity of the corresponding molecules of the invention. Thus, for example, the variant shRNA molecules of the invention retain the ability of the corresponding shRNA molecules to inhibit the expression of REV-ERB. The variant shRNA molecules may retain at least 50%, at least 60%, at least 70%, at least 80%, at least 90%, up to and including 100% of the modulatory activity of the shRNA molecules of the invention. This applies equally to any other variants of the inhibitors of the invention.

The compounds of the invention may be labelled (or tagged). Any appropriate label may be used. Suitable labels are known in the art.

Post-Translational Modification of E4bp4

As shown in the Examples, the present inventors have demonstrated that post-translational modification of E4bp4 can increase E4bp4 activity. Furthermore, increasing E4bp4 activity by post-translational modification results in an increase in NK cell number (as defined herein).

Accordingly, the present invention provides a method of expanding an NK cell population, comprising the steps of: a) culturing an haematopoietic progenitor cell (HPC) comprising sample obtained from an individual/patient; b) contacting said sample with a compound which results in the post-translational modification of E4bp4, thereby causing an increase in E4bp4 activity; and c) expanding said cells in vitro to produce an NK cell population. Said method can be used together with, or independently from the methods disclosed herein relating to increased E4bp4 expression by decreasing REV-ERB activity, and/or the methods disclosed herein relating to increasing NK cell number by culturing HPCs in the presence of a Notch ligand.

The invention also provides a compound which results in the post-translational modification of E4bp4 for use in a method of therapy by increasing production of NK cells in a patient, wherein said compound increases E4bp4 activity. The invention further provides a method of treatment by increasing the number of NK cells in a patient in need thereof, comprising administering to said patient a therapeutically effective amount of a compound which results in the post-translational modification of E4bp4, wherein said compound increases E4bp4 activity. Again, said therapeutic indications can be used together with, or independently from the indications disclosed herein relating to increased E4bp4 expression by decreasing REV-ERB activity, and/or the indications disclosed herein relating to increasing NK cell number by culturing HPCs in the presence of a Notch ligand.

Any of the disclosure herein in relation to methods of increasing NK cell number, methods of expanding NK cells in the context of compounds which inhibit the action of REV-ERB, and/or Notch ligands, expanded NK cell populations produced by said methods and therapeutic indications relating to said compounds and populations applies inter alia to the disclosed methods of increasing E4bp4 activity to increase NK cell number. As non-limiting examples, the feeder cell layers, growth factors and/or other culture conditions and diseases to be treated may be the same in relation to the post-translational modification aspects as for the REV-ERB inhibition and/or Notch ligand aspects disclosed herein.

Types of Post-Translational Modification

Said method encompasses any post-translational modification which results in an increase in E4bp4 activity. Non-limiting examples of post-translation modification include phosphorylation, SUMOylation, the addition of a hydrophobic group (e.g. myristoylation, palmitoylation), addition of a cofactor, the addition of small chemical groups (e.g. acylation, alkylation, amidation, glycosylation), glycation, carbamylation, cabonylation, chemical modifications (e.g. deamidation) and/or structural changes. Typically said post-translational modification results in a reduction in phosphorylation at one or more phosphorylation site within wild-type (unmodified) E4bp4 and/or a reduction in SUMOylation at one or more SUMOylation site within wild-type (unmodified) E4bp4, or a combination thereof. As shown in the Examples herein, wild-type (unmodified) E4bp4 is typically SUMOylated at one or more of residues K10, K116, K219, K337 and/or K394 or residues corresponding thereto, or any combination thereof. Typically wild-type (unmodified) E4bp4 is SUMOylated at least at residue K219 (or a corresponding residue). Alternatively or in addition, wild-type (unmodified) E4bp4 is typically phosphorylated at residues S286, S301 and S353, or residues corresponding thereto, or any combination thereof. Accordingly, in some preferred embodiments, a compound of the invention reduces, inhibits or ablates SUMOylation at residue K219 (or a residue corresponding thereto), and/or reduces, inhibits or ablates phosphorylation at residues S286, S301 and S353 (or corresponding residues), or any combination thereof. Thus, according to the present invention, a compound may be used to (a) reduce SUMOylation at one or more of residues K10, K116, K219, K337 and/or K394 of E4bp4, or a residue corresponding thereto, or any combination thereof; and/or reduce phosphorylation at one or more of residues S286, S301 and/or S454, or a residue corresponding thereto, or any combination thereof.

Any compound which is capable of eliciting a post-translational modification of E4bp4, wherein said modification increases the activity of E4bp4 is encompassed by the present invention. In some preferred embodiments, said compound inhibits, reduces or ablates the phosphorylation and/or SUMOylation that occurs in wild-type (unmodified) E4bp4. Any appropriate kinase inhibitor may be used to inhibit, reduce or ablate phosphorylation of E4bp4. Suitable kinase inhibitors are known in the art and their selection would be routine to one of skill in the art. Non-limiting examples of suitable kinase inhibitors include 4-(4-(2,3-Dihydrobenzo[1,4]dioxin-6-yl)-5-pyridin-2-yl-1H-imidazol-2-yl)benzamide (D4476) and 4,5,6,7-Tetrabromo-2-azabenzimidazole, 4,5,6,7-Tetrabromobenzotriazole (TBB).

Increase in E4bp4 Activity

The present invention relates to the use of compounds post-translationally modify E4bp4 and hence to increase E4bp4 activity. An increase in E4bp4 activity may be measured relative to a control. Thus, the activity of E4bp4 in a sample of NK precursor or progenitor cells, an expanded NK cell population or in a sample obtained from an individual/patient to be treated according to the invention may be compared with the activity of E4bp4 in a control. Activity may be quantified in any appropriate terms, for example an increase in the expression of any downstream target of E4bp4. Any appropriate technique or method may be used for quantifying E4bp4 activity. Suitable techniques are known in the art, for example luciferase assays for quantifying expression of a reporter gene.

Typically the control is an equivalent population or sample in which no compound has been added to post-translationally modify E4bp4, for example a sample obtained from a different individual to which the compound has not been administered, or the same individual the prior to administration of the compound. Conventional methods for the ex vivo expansion of NK cells, including known methods may be considered control methods according to the present invention.

In the context of the present invention, a reference to increasing E4bp4 activity may be understood to mean that, the activity of E4bp4 is increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically E4bp4 activity is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control. E4bp4 activity may be measured indirectly be determining the increase in NK cell number. Thus, the number of NK cells may be increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically the number of NK cells is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control.

The activity of E4bp4 may be determined by quantitative and/or qualitative analysis, and may be measured directly or indirectly. The activity of E4bp4 relative to a control may be determined using any appropriate technique. Suitable standard techniques are known in the art.

The activity of E4bp4 may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the activity of E4bp4 is increased for at least 12 to 72 hours. Typically this is assessed relative to the last administration of the compound which post-translationally modified E4bp4.

The activity of E4bp4 may be increased compared with a control for at least one, at least two, at least three, at least four, at least five, at least ten, at least 20, at least 30, at least 40 or more passages of the cultured cells. The activity of E4bp4 may be increased indefinitely.

Methods of Expanding NK Cells

The present invention relates to a method for expanding an NK cell population. Typically said methods involve culturing NK cell precursors (HPCs) in the presence of a Notch ligand. Said method may be in vitro, in vivo or ex vivo. Typically the method of the invention is ex vivo. Said method comprises containing HPCs with a Notch ligand and expanding said cells to produce an NK cell population. The methods of the invention allow for the rapid expansion of NK cells, reducing the time needed for their culture, and hence the risk of exhaustion, enhancing the cytotoxicity of the NK cells when transfused into a patient.

When said method is carried out in vivo, said method is a therapeutic method as described herein. In such embodiments, all the disclosure herein in relation to therapeutic indications and applications of the invention is applicable to said methods.

As disclosed herein, the present inventors have shown that Notch ligands, particularly DLL4, can be used to enhance the production of NK cells. Accordingly, the invention provides an ex vivo method for expanding an NK cell population comprising: (a) culturing an HPC comprising sample obtained from an individual/patient in the presence of a Notch ligand, a fragment thereof which retains the function of said Notch ligand, or a molecule which mimics the function of said Notch ligand; and (b) culturing the cells produced by step (a) in the presence of IL-15; thereby producing an expanded NK cell population.

Step (a) and (b) may be carried out concurrently or in any order. For example, step (a) may be carried out first, followed by step (b), such that the cells are first exposed to a Notch ligand and then IL-15. Alternatively, step (b) may be carried out first, followed by step (a), such that the cells are first cultured in the presence of IL-15 and then in the presence of a Notch ligand. Alternatively, steps (a) and (b) may be carried out concurrently, such that the cells are simultaneously cultured in the presence of a Notch ligand and IL-15. Preferably step (a) is carried out first, followed by step (b).

The Notch ligand may be any Notch ligand (including functional fragments thereof and molecules which mimic the action/function/effect of the Notch ligand of interest) as defined herein. Typically the Notch ligand is DLL4, a fragment thereof which retains the function of DLL4, or a molecule which mimics the function of DLL4 (as defined herein).

Typically in step (a) the HPCs are cultured in the absence of exogenous IL-15, with exogenous 11-15 being added in step (b) only. As a non-limiting example, IL-15 may be used at a concentration of about 1 ng/ml to about 100 ng/ml, about 1 ng/ml to about 50 ng/ml, about 1 ng/ml to about 40 ng/ml, about 1 ng/ml to about 30 ng/ml, about 1 ng/ml to about 20 ng/ml, about 1 ng/ml to about 10 ng/ml or less. In some embodiments IL-15 is used at a concentration of about 50 ng/ml, about 40 ng/ml, about 35 ng/ml, about 30 ng/ml, about 25 ng/ml, about 20 ng/ml or about 10 ng/ml, preferably about 30 ng/ml.

Additional external stimuli, such as growth factors and/or cytokines, may be used to further enhance the production of NK cells. Said external stimuli may be present in step (a) and/or step (b) as appropriate. Non-limiting examples of suitable external stimuli include IL-7, Flt3L, stem cell factor (SCF), thrombopoietin (TPO), IL-3 and/or IL-6, or any combination thereof. In some preferred embodiments, IL-7, Flt3L and/or SCF, or any combination thereof is used. More preferably IL-7, Flt3L and SCF are used.

As a non-limiting example, IL-7 may be used at a concentration of about 1 ng/ml to about 100 ng/ml, about 1 ng/ml to about 50 ng/ml, about 1 ng/ml to about 25 ng/ml, about 1 ng/ml to about 10 ng/ml or less. In some embodiments IL-7 is used at a concentration of about 50 ng/ml, about 25 ng/ml, about 20 ng/ml, about 15 ng/ml, about 10 ng/ml or about 5 ng/ml, preferably about 10 ng/ml. As a non-limiting example, Flt3L may be used at a concentration of about 1 ng/ml to about 100 ng/ml, about 1 ng/ml to about 50 ng/ml, about 1 ng/ml to about 25 ng/ml, about 1 ng/ml to about 10 ng/ml or less. In some embodiments Flt3L is used at a concentration of about 50 ng/ml, about 25 ng/ml, about 20 ng/ml, about 15 ng/ml, about 10 ng/ml or about 5 ng/ml, preferably about 10 ng/ml. As a non-limiting example, SCF may be used at a concentration of about 1 ng/ml to about 200 ng/ml, about 1 ng/ml to about 150 ng/ml, about 1 ng/ml to about 100 ng/ml, about 1 ng/ml to about 50 ng/ml or less. In some embodiments SCF is used at a concentration of about 150 ng/ml, about 125 ng/ml, about 120 ng/ml, about 110 ng/ml, about 100 ng/ml, about 90 ng/ml, about 80 ng/ml or about 75 ng/ml, preferably about 100 ng/ml.

Typically IL-7, Flt3L and SCF are used together in step (a) only, step (b) only or in both steps (a) and (b). In some preferred embodiments, the HPCs are cultured in the presence of IL-7, Flt3L and/or SCF, more preferably IL-7, Flt3L and SCF, in step (a).

The Notch ligand (such as DLL4) may be present in solution (e.g. in the culture medium) or used to coat the vessel in which the HPCs are cultured. Preferably the Notch ligand (e.g. DLL4) is used to coat the vessel in which the HPCs are cultured. As a non-limiting example, the Notch ligand (e.g. DLL4) may be used at a concentration of about 1 μg/ml to about 100 μg/ml, about 1 μg/ml to about 50 μg/ml, about 1 μg/ml to about 25 μg/ml, about 1 μg/ml to about 10 μg/ml or less. In some embodiments the Notch ligand (e.g. DLL4) is used at a concentration of about 50 μg/ml, about 25 μg/ml, about 20 μg/ml, about 15 μg/ml, about 10 μg/ml, or about 5 μg/ml, preferably about 10 μg/ml. Additional substrates and/or linkers may be used to facilitate the attachment of the Notch ligand (such as DLL4) to the surface of the culture vessels. Examples of such substrates are known in the art, such as poly-L-lysine.

Step (a) and/or step (b) of the method of the invention may involve culturing said cells in the presence or absence of a stromal support cell or feeder cell, or population thereof. As used herein, the terms stromal cell, feeder cell and stromal support cell are synonymous and may be used interchangeably. Examples of such support/feeder cells include, but are not limited to, OP9 cells and/or EL08-1D2 cells. Typically step (a) is carried out in the absence of a stromal support cell or population thereof. In some preferred embodiments, both step (a) and step (b) are carried out in the absence of a stromal support cell or population thereof. In other words, these steps may be carried out coating the Notch ligand of the invention (e.g. DLL4) directly onto tissue culture plastic.

Steps (a) and (b) may be of any appropriate duration to maximise the production of NK cells. As a non-limiting example, step (a) may involve the culture of HPCs in the presence of a Notch ligand (such as DLL4) for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, i.e. step (a) may be any of these durations. Typically step (a) is 72 hours to 1 week in length. As a non-limiting example, step (b) may involve the culture of the cells produced by step (a) in the presence of IL-15 for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, at least 2 weeks, at least 3 weeks or longer, until the desired number of NK cells is produced. Thus, step (b) may be any of these durations. Typically step (b) is 1 week or more in length, in some preferred embodiments step (b) is 7 to 9 days in length, in even more preferred embodiments, step (b) is about two weeks in length.

Alternatively, the duration of step (a) and/or step (b) may be measured in terms of the number of cell passages. For example, step (a) and/or step (b) may be at least one, at least two, at least three, at least four, at least five, at least ten, at least 20, at least 30, at least 40 or more passages of the cells (either in vivo, or cultured ex vivo or in vitro).

The durations of step (a) and step (b) are independent, and any duration of step (a) above may be used in combination with any duration of step (b) above. In some preferred embodiments, step (a) is 72 to 1 week in length and step (b) is 1 week (or more) in length.

The present inventors have also demonstrated that combining the use of a Notch ligand (such as DLL4) and REV-ERB inhibition results in a surprisingly potent means for enhancing NK cell production, allowing for the production of large numbers of functional NK cells that are suitable for in vivo therapeutic use more rapidly than the current methods. It is surprising that these two independent mechanisms (Notch ligand and REV-ERB inhibition) can be used together to demonstrate a greater increase in NK cell number than either mechanism provides alone.

Accordingly, the present invention provides in vitro, in vivo and ex vivo methods for expanding NK cells using the combination of a Notch ligand and REV-ERB inhibition. When said method is carried out in vivo, said method is a therapeutic method as described herein. In such embodiments, all the disclosure herein in relation to therapeutic indications and applications of the invention is applicable to said methods. Typically the method of the invention is ex vivo.

Thus, the invention provides an ex vivo method for expanding an NK cell population comprising the steps of: (a) culturing an HPC comprising sample obtained from an individual/patient with a compound that inhibits the action of REV-ERB (as described herein); (b) culturing said cells in the presence of a Notch ligand (such as DLL4); and (c) expanding said cells in vitro to produce an NK cell population. Step (a) and (b) may be carried out concurrently or in any order. For example, step (a) may be carried out first, followed by step (b), such that the cells are first exposed to a REV-ERB inhibitory compound and then cultured in the presence of a Notch ligand. Alternatively, step (b) may be carried out first, followed by step (a), such that the cells are first cultured in the presence of a Notch ligand and then in the presence of a REV-ERB inhibitory compound. Alternatively, steps (a) and (b) may be carried out concurrently, such that the cells are simultaneously cultured in the presence of a REV-ERB inhibitory compound and a Notch ligand.

In some preferred embodiments, step (a) may be carried out first, followed by step (b), such that the cells are first cultured in the presence of a REV-ERB inhibitory compound and then in the presence of a Notch ligand. Thus, in those embodiments the invention provides an ex vivo method for expanding an NK cell population comprising the steps of: (a) culturing an HPC comprising sample obtained from an individual/patient with a compound that inhibits the action of REV-ERB (as described herein); (b) culturing said cells in the presence of a Notch ligand (such as DLL4); and (c) expanding said cells in vitro to produce an NK cell population.

The compound may be any REV-ERB inhibitory compound of the invention as described herein. Typically said compound increases E4bp4 expression by decreasing REV-ERB activity as described herein. The Notch ligand may be any Notch ligand of the invention as described herein. In some preferred embodiments the REV-ERB inhibitory compound is SR8278. In some preferred embodiments the Notch ligand is DLL4, a functional fragment thereof or a molecule which mimics the activity/function of DLL4. In some particularly preferred embodiments, the REV-ERB inhibitory compound is SR8278 and the Notch ligand is DLL4, a functional fragment thereof or a molecule which mimics the activity/function of DLL4.

The Notch ligand (such as DLL4) may be present in solution (e.g. in the culture medium) or used to coat the vessel in which the HPCs are cultured. Preferably the Notch ligand (e.g. DLL4) is used to coat the vessel in which the HPCs are cultured. Any appropriate concentration of Notch ligand may be used. Non-limiting examples of suitable Notch ligand concentrations are described herein. In other words, these steps may be carried out coating the Notch ligand of the invention (e.g. DLL4) directly onto tissue culture plastic.

The HPCs may be cultured in the presence or absence of a stromal support cell or feeder cell, or population thereof. Any appropriate stromal cell may be used, including, but not limited to OP9 stromal cells and/or EL08-1D2 stromal cells. In some preferred embodiments, the cells are cultured in the absence of a stromal support cell or population thereof.

Alternatively and/or in addition, the HPCs may be cultured in the presence of cytokines and growth factors associated with the development of cells in the NK cell differentiation pathway, including factors required for HPCs growth and/or factors required for NK cell growth and/or differentiation. Non-limiting examples of such factors include IL-3, IL-7, Flt3L, stem cell factor (SCF), TPO, IL-3, IL-6, and/or IL-15, or any combination thereof. Any appropriate concentration of such factors may be used. Non-limiting examples of suitable concentrations of these factors are described herein.

In some embodiments, the ex vivo method comprises a single stage in which the HPCs in a sample obtained from an individual/patient are cultured, contacted with a compound of the invention and a Notch ligand and expanded to form an NK cell population, typically under substantially constant culture conditions (i.e. steps (a) and (b) of the method are carried out concurrently). Typically this involves incubating the HPCs with factors such as IL-3, IL-7, SCF, Flt3L and/or IL-15, preferably all of these factors. The HPCs may be cultured in the presence or absence of stromal cells/cell layer, such as EL08-1D2 stromal cells.

In some embodiments, the ex vivo method comprises two stages. The first is a lymphoid production stage, in which the HPCs in a sample obtained from an individual/patient are cultured. Typically this involves incubating the HPCs with cytokines and growth factors associated with lymphoid production, such as Flt3L, IL-7 and/or SCF. This stage may last for at least one, at least two, at least three, at least four, or more days. In some preferred embodiments, this stage lasts for two days.

This is followed by a stage of NK cell expansion. Typically this involves culturing the cells in cytokines and growth factors associated with NK cell development, such as IL-15, and may involve transferring the cultured HSCs to a suitable stromal (support) cell layer, such as OP9 stromal cells. The second stage lasts for the remainder of the ex vivo culture period (as defined herein). The culture medium may be changed as often as required during this second stage in order to facilitate NK cell expansion.

In some embodiments, the REV-ERB inhibitory compound of the invention is added in stage 1 (lymphoid production) and the Notch ligand in the second stage (NK cell expansion). In other embodiments, the Notch ligand is added in stage 1 (lymphoid production) and the REV-EB inhibitory compound in the second stage (NK cell expansion). In yet other embodiments, both the REV-ERB inhibitory compound and the Notch ligand added in the first stage (lymphoid production). In further embodiments, both the REV-ERB inhibitory compound and the Notch ligand added in the second (NK cell expansion phase). If the REV-ERB inhibitory compound and the Notch ligand added in the same stage (either stage 1 or stage 2), that stage may be further divided so that: (i) the REV-ERB inhibitory compound is added before the Notch ligand; or (ii) the Notch ligand is added before the REV-ERB inhibitory compound. Alternatively, the Notch ligand and REV-ERB inhibitory compound may be added simultaneously in the same stage.

Typically the REV-ERB inhibitory compound is added during the first stage, and the Notch ligand is added during the second stage, and preferably at the start of this second stage.

The HPC comprising sample may be cultured ex vivo for at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days or more. Typically said sample is cultured for at least 9 days in order to produce an expanded NK cell population. These culture periods are for the total culture period of the ex vivo method, i.e. if there are two stages, these periods are for the total (stage 1 plus stage 2).

The REV-ERB inhibitory compound of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the REV-ERB inhibitory compound of the invention is added to the sample within two days of isolating the HPCs in the sample, such as on the day of isolation of the HPCs. Most preferably the REV-ERB inhibitory compound of the invention is added to the sample two days post isolation of the HPCs.

The Notch ligand of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the Notch ligand of the invention is added to the sample within four days of isolating the HPCs in the sample, such as on day two following isolation of the HPCs. Most preferably the Notch ligand of the invention is added to the sample two or four days post isolation of the HPCs.

Preferred embodiments of the invention comprise (i) adding the REV-ERB inhibitory compound and the Notch ligand to the sample on the day of isolation of the HPCs; (ii) adding the REV-ERB inhibitory compound to the sample on the day of isolation of the HPCs and adding the Notch ligand to the sample on day two post isolation of the HPCs; or (iii) adding the REV-ERB inhibitory compound to the sample on day two post isolation of the HPCs and adding the Notch ligand to the sample on day four post isolation of the HPCs; with option (iii) being particularly preferred. As demonstrated in the Examples, these particular conditions maximise the synergy between the REV-ERB inhibition and the Notch ligand, and hence maximising the expansion of NK cells.

The method of the invention may further comprise modulating (increasing or decreasing the expression and/or activity of one or more additional gene and/or protein in the HPCs in order to enhance NK cell expansion. This modulation may be elicited by a compound of the invention, including the same compound of the invention as used to inhibit the activity of REV-ERB. Alternatively, one or more additional compounds may be used to modulate the expression and/or activity of the one or more additional gene and/or protein. Said modulation may occur directly or indirectly. Indirect modulation encompasses downstream effects caused by a compound of the invention inhibiting the activity of REV-ERB.

Any of the methods of the invention may be used on its own or in combination with other methods of the invention. For example, methods of the invention relating to inhibiting the action of REV-ERB and culturing HPCs in the presence of a Notch ligand may be combined with the invention relating to culturing in the presence of DLL4 or a functional fragment thereof (i.e. the Notch ligand is DLL4 or a DLL4 fragment) and in the presence of IL-15 and/or the invention relating to post-translational modification of E4bp4 in order to increase E4bp4 activity. Any combination of the methods as disclosed herein is envisaged by the present invention.

In all methods of the invention, the sample comprising HPCs obtained from an individual/patient may be a sample obtained from bone marrow, cord blood and/or peripheral blood. Thus, the sample may be a cord or peripheral blood sample, or a bone marrow sample or biopsy. The sample may be obtained from the individual who is to be treated with the NK cell population produced by a method of the invention (i.e. a patient). Alternatively, the sample is obtained from a healthy individual.

According to the present invention, a sample comprising HPCs is any sample from an individual which comprises a sufficient number of HPCs (as described herein), such that an expanded NK cell population can be obtained by contacting said sample with a compound according to the present invention. Typically the sample comprises HSCs. Preferably said sample is enriched for HSCs, such as a cord or peripheral blood sample or a bone marrow sample or biopsy as described herein.

A method of the invention may result in an increase in, the number of NK cells of at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically the number of NK cells is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control.

A method of the invention may accelerate the production of phenotypically mature NK cells. In other words, the method of the invention may reduce the time taken to arrive at a population of mature NK cells. A reduction in the run time of the method offers a further advantage over the conventional methods for NK cell expansion known in the art. As a non-limiting example, current clinical procedures for the expansion of NK cells can take more than two weeks to generate an NK cell population that comprises about 20% mature NK cells. In contrast, a method of the invention may achieve an equivalent population in 10 days or less, preferably in one week or less. A method of the invention may achieve a population of at least 40% mature NK cells, preferably at least 45%, at least 46%, at least 47%, at least 48%, or at least 49% mature NK cells, even more preferably at least 50% mature NK cells in three weeks or less, 20 days or less, 19 days or less, 18 days or less, 17 days or less, 16 days or less, 15 days or less, two weeks or less, 13 days or less, or 12 days or less. Preferably a method of the invention can achieve a population of at least 45% mature NK cells within two weeks or less.

Typically any ex vivo method of the present invention involves a final step to purify the expanded NK cell population. This ensures a pure population for therapeutic administration as described herein. Purification of the expanded NK cell population may be by any appropriate means. Standard cell purification methods are known in the art, such as cell sorting, including fluorescence-activated cell sorting (FACS) and magnetic-activated cell sorting (MACS). In some methods of the invention, particularly those involving the combination of a Notch ligand and a REV-ERB inhibitory compound, the % of NK cells in the final cell population may be very high (typically greater than 85%, preferably greater than 90%, more preferably greater than 95%, and may approach 100%). In such instances, a final purification step may optionally be omitted.

Therapeutic Indications

The invention provides products containing a compound which inhibits the action of REV-ERB and a Notch ligand as a combined preparation for simultaneous, separate or sequential use in a method of therapy by increasing the production of NK cells in a patient.

The Notch ligand for use in said method of therapy may be any Notch ligand as described herein. In some preferred embodiments, the Notch ligand is DLL4 or a fragment thereof which retains the function of DLL4.

The REV-ERB antagonist for use in said method of therapy may be any REV-ERB antagonist as described herein. Typically the REV-ERB antagonist for use in said method increases E4bp4 expression by decreasing REV-ERB activity.

A reference herein to products of the invention is a reference to the combination of a REV-ERB antagonist and Notch ligand as described herein (for simultaneous, separate or sequential use).

Any REV-ERB antagonist and any Notch ligand of the invention may be used in combination. As a non-limiting example, DLL4 or a functional fragment thereof may be used in combination with SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine, preferably SR8278.

Typically the method of therapy comprises administering the products (as described herein) to a patient or subject. The Notch ligand and REV-ERB antagonist may be administered simultaneously, separately or sequentially. For separate or sequential administration, the Notch ligand may be administered first, followed by the REV-ERB antagonist, or vice versa.

Sequential administration may mean that the two products are administered immediately one after the other, or that the second product is administered within 1 minute, within two minutes, within three minutes, within four minutes, within five minutes, within 10 minutes, within 15 minutes, within 20 minutes, within 25 minutes, within 30 minutes, within 45 minutes, within one hour, or more of the first product being administered.

Separate administration may mean that the second product is administered within one hour, within two hours, within three hours, within six hours, within 12 hours, within 24 hours, within 2 days, within 3 days, within 4 days, within 5 days, within 6 days, within 7 days or more of the first product being administered.

As used herein, the term "increasing the number of NK cells" and "increasing production of NK cells" can be understood to mean that the compound or products of the invention elicit(s) a significant increase in the number of NK cells in a patient. This increase in NK cell number may be measured relative to a control (as described herein in the context of increasing E4bp4 expression and inhibiting REV-ERB activity).

A reference to an increase in the number of NK cells and/or increasing NK cell production may be quantified in terms of a fold increase relative to a control. Typically a compound of the invention can increase the number of NK cells, or give rise to an increase in NK cell production, of at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 3 fold or more relative to a control.

Alternatively, a reference to increasing the number of NK cells and/or increasing NK cell production may be understood to mean that, the number of NK cells is increased by at least 10%, at least 20%, at least 30%, at least 40%, at least 50%, at least 60, at least 70%, at least 80%, at least 85%, at least 90%, at least 95%, at least 100%, at least 150%, at least 200%, at least 300% or more compared with the control. Typically the number of NK cells is increased by at least 50%, preferably at least 70%, more preferably at least 80%, even more preferably at least 90% or more compared with a control.

In some embodiments, an increase in the number of NK cells and/or increase in NK cell production may be defined in terms of the absolute number of NK cells in a sample or patient, such as the percentage of NK cells, for example the percentage of NK cells in the circulating lymphocyte population. For example, a compound of the invention may cause an increase in NK number, resulting in a percentage of NK cells of at least 10%, at least 15%, at least 20%, at least 25%, at least 30%, at least 35%, at least 40%, at least 45%, at least 50%, at least 55%, at least 60%, at least 65%, at least 70%, at least 75%, at least 80% or more.

The number of NK cells may be determined by quantitative and/or qualitative analysis, and may be measured directly or indirectly. The number of NK cells relative to a control may be determined using any appropriate technique. Suitable standard techniques, such as flow cytometry, FACS and MACS, are known in the art.

The number of NK cells may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, at least 2 weeks, at least 3 weeks, at least 1 month or more. Typically this is assessed relative to the last administration of the compound which inhibits REV-ERB activity and/or the Notch ligand.

The number of NK cells may be quantified in terms of the total number of NK cells in a sample from an individual/patient or culture sample (from an ex vivo method of the invention).

In the context of the therapeutic uses and methods of the invention, a "subject" or "patient" (these terms are used interchangeably herein) is any animal patient that would benefit from an increase in the number of NK cells. Typical animal patients are mammals, such as primates. Preferably the patient is a human.

Thus, the present invention provides a method of treatment by increasing the number of NK cells in a patient in need thereof, comprising administering to said patient a therapeutically effective amount of a compound which inhibits the action of REV-ERB (as described herein) and a Notch ligand (as described herein).

Additionally, the present invention provides the use of a compound which inhibits the action of REV-ERB and a Notch ligand in the manufacture of a medicament. Said medicament increases the number of NK cells in a patient.

The therapeutic use or method of the invention may comprise administering a therapeutically effective amount of a compound or products of the invention (as defined herein), either alone or in combination with other therapeutic agents, to a subject or individual.

As used herein, the term "treatment" or "treating" embraces therapeutic or preventative/prophylactic measures.

The compounds or products of the invention may also be used as a preventative therapy. As used herein, the term "preventing" includes preventing the onset of symptoms associated with a disease or disorder that may be treated by increasing NK cell number and/or reducing the severity or intensity of said symptoms. The term "preventing" includes inducing or providing protective immunity against such diseases or disorders, particularly infectious diseases as described herein. Immunity may be quantified using any appropriate technique, examples of which are known in the art.

A compound or products of the invention may be administered to a patient already having a disease or disorder which may be treated by increasing NK cell number. For example, the patient may be suspected of having an infectious disease or cancer as described herein, and may or may not be showing symptoms of said disease or disorder. When administered to such a patient, a compound or products of the invention can cure, delay, reduce the severity of, or ameliorate one or more symptoms, and/or prolong the survival of a subject beyond that expected in the absence of such treatment.

Alternatively, a compound or products of the invention may be administered to a patient who may ultimately be infected with a particular infectious disease, or develop a disease or disorder as described herein, in order to cure, delay, reduce the severity of, or ameliorate one or more symptoms, and/or prolong the survival of a subject beyond that expected in the absence of such treatment, or, in the case of infectious diseases help prevent that patient from transmitting said disease.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The invention relates to the treatment of any disease or disorder which may be beneficially treated with by increasing the number of NK cells in a patient. Such diseases and disorders include cancer, infectious diseases (acute and chronic), autoimmune diseases and diseases or disorders related to female infertility or pregnancy. Infectious diseases that may be treated according to the present invention include viral infection, and infection by other pathogens, including bacteria, protists, fugal, or helminth pathogens. Typically said pathogens are intracellular pathogens which have at least one intracellular phase in their life cycle. Infections of particular interest include viral infections, and zoonotic infections that are of particular importance from a public health perspective. Cancers that may be treated according to the present invention include bladder cancer, blood cancers, leukaemia, bone cancers, bowel cancer, brain tumours, breast cancer, kidney cancer, liver cancer, lung cancer, melanoma, ovarian cancer, pancreatic cancer, prostate cancer, skin cancer, stomach cancer, testicular cancer and uterine cancer. Autoimmune diseases that may be treated according to the present invention include systemic lupus erythematosus, rheumatoid arthritis, multiple sclerosis and obesity-induced insulin resistance. As used herein, the term diseases or disorders related to female infertility or pregnancy includes, but is not limited to, fetal growth restriction, preterm labour, defects in uterine vascular remodelling and preeclampsia.

The compounds or products of the invention may be used in combination with one or more additional therapeutic agents or treatments, which typically may be selected from a conventional treatment for the disease or disorder to be treated. As a non-limiting example, if a compound or products of the invention are for use in the treatment of a cancer, such as lung cancer, then said compound or products may be used in combination with conventional treatments for lung cancer, such as radiotherapy, chemotherapy or surgery. When used in combination with one or more additional therapeutic agent or treatment, a compound or products of the invention may be administered before, simultaneously with, or after the administration of the one or more additional therapeutic agent or treatment.

In some preferred embodiments, a compound or products of the invention is for use in combination with antibody-mediated immunotherapy. Antibody-mediated immunotherapy involves the administration of antibodies to a patient to target disease-specific antigens. Such antibodies could be used to increase the specificity and killing activity of NK cells, which express receptors for the Fc regions of IgG antibodies. Activation of these Fc receptors, leads to NK cell activation, resulting in cytokine secretion and release of cytotoxic granules by the activated NK cell, causing lysis of the cell expressing the disease antigen. Such combination therapy is particularly preferred for the treatment of cancer (using antibodies to tumour-specific antigens). Any antibody used in immunotherapy may be used in combination with a compound or products of the invention. Non-limiting examples of such antibodies include anti-CD20 mAbs (non-Hodgkin's lymphoma, chronic lymphocytic lymphoma), anti-ganglioside D2 (anti-GD2) mAbs (neuroblastoma, melanoma), anti-human epidermal growth factor (anti-HER2) mAbs (breast and gastric cancers), anti-epidermal growth factor receptor (anti-EGFR) mAbs (colorectal and head and neck cancer).

The invention also provides the use of a compound which results in the post-translational modification of E4bp4, thereby causing an increase in E4bp4 activity (as described herein) in a therapeutic use or method as described herein. Any and all of the disclosure herein in relation to therapeutic indications of a compound or products of the invention may apply equally and independently to therapeutic applications of compounds which result in the post-translational modification of E4bp4, according to the present invention. As a non-limiting example, the present invention provides a compound which results in the post-translational modification of E4bp4, thereby causing an increase in E4bp4 activity (as described herein) for use in a method of therapy, for example in the treatment of cancer, an infectious diseases, an autoimmune disease or a disease or disorder related to female infertility or pregnancy. As another non-limiting example, the invention provides a method of treatment by increasing the number of NK cells in a patient in need thereof, comprising administering to said patient a therapeutically effective amount of a compound which results in the post-translational modification of E4bp4, thereby causing an increase in E4bp4 activity.

In other aspects, the invention provides the use of an expanded NK cell population (as described herein) in a therapeutic use or method as described herein. Any and all of the disclosure herein in relation to therapeutic indications of a compound or products of the invention may apply equally and independently to therapeutic applications of the expanded NK cell populations of the invention. As a non-limiting example, the present invention provides an expanded NK cell population (as described herein) for use in a method of therapy, for example in the treatment of cancer, an infectious diseases, an autoimmune disease or a disease or disorder related to female infertility or pregnancy. As another non-limiting example, the invention provides a method of treatment by increasing the number of NK cells in a patient in need thereof, comprising administering to said patient a therapeutically effective amount of an expanded NK cell population.

Pharmaceutical Compositions and Formulations

The terms "compound" or "products" are herein used interchangeably with the terms "therapeutic/prophylactic composition", "formulation" or "medicament".

The compound, products or expanded NK cell population of the invention (as defined above) can be combined or administered in addition to a pharmaceutically acceptable carrier, diluent and/or excipient. Alternatively or in addition the compound, products or expanded NK cell population of the invention can further be combined with one or more of a salt, excipient, diluent, adjuvant, immunoregulatory agent and/or antimicrobial compound.

Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations is generally by conventional routes e.g. intravenous, subcutaneous, intraperitoneal, or mucosal routes. The administration may be by parenteral injection, for example, a subcutaneous, intradermal or intramuscular injection. For example, formulations comprising antibodies or expanded NK cell populations of the invention may be particularly suited to administration intravenously, intramuscularly, intradermally, or subcutaneously. Administration of small molecule REV-ERB inhibitors may be injection, such as intravenously, intramuscularly, intradermally, or subcutaneously, or by oral administration (small molecules with molecule weight of less than 500 Da typically exhibiting oral bioavailability).

Accordingly, immunogenic compositions, therapeutic formulations, medicaments and prophylactic formulations of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients (such as the compounds, products or expanded NK cell populations of the invention) are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, where the composition comprises a compound or products of the invention, this may be in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IFA), Saponin, a purified extract fraction of Saponin such as Quil A, a derivative of Saponin such as QS-21, lipid particles based on Saponin such as ISCOM/ISCOMATRIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, AS01, AS03 and AS04 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

The dosage ranges for administration of the compounds or products of the present invention are those which produce the desired therapeutic effect. It will be appreciated that the dosage range required depends on the precise nature of the compound or products, the route of administration, the nature of the formulation, the age of the patient, the nature, extent or severity of the patient's condition, contraindications, if any, and the judgement of the attending physician. Variations in these dosage levels can be adjusted using standard empirical routines for optimisation. Similarly, the dose of a compound or products of the invention for use in a method of the invention, particularly an ex vivo method, can be readily determined by one of skill in the art, and is any dose that produces the desired increase in NK cell number and/or elicits the desired expansion in NK cells, to produce an expanded NK cell population. As a non-limiting example, doses of SR8278 according to the present invention may give rise to a final concentration of about 2 to about 20 µM, about 2 to about 15 µM, about 5 to about 15 µM, about 5 to about 14 µM, about 4 to about 13 µM, about 5 to about 12 µM, about 5 to about 11 µM, or preferably about 5 to about 10 µM.

The invention also provides the use of an expanded NK cell population (as described herein) in a pharmaceutical formulation. Any and all of the disclosure herein in relation to formulations of a compound of the invention may apply equally and independently to therapeutic applications of the expanded NK cell populations of the invention.

Key to SEQ ID NOs

```
Delta-like ligand 4 gene sequence (AF253468.1)
                                                                SEQ ID NO: 1
       1    atggcggcag cgtcccggag cgcctctggc tgggcgctac tgctgctggt ggcactttgg 61    cagcagcgcg cggccggctc cggcgtcttc cagctgcagc tgcaggagtt catcaacgag 121    cgcggcgtac tggccagtgg gcggccttgc gagcccggct gccggacttt cttccgcgtc 181    tgccttaagc acttccaggc ggtcgtctcg cccggaccct gcaccttcgg gaccgtctcc 241    acgccggtat tgggcaccaa ctccttcgct gtccgggacg acagtagcgg cggggggcgc 301    aaccctctcc aactgcccct caatttcacc tggccgggta ccttctcgct catcatcgaa 361    gcttggcacg cgccaggaga cgacctgcgg ccagaggcct tgccaccaga tgcactcatc 421    agcaagatcg ccatccaggg ctccctagct gtgggtcaga actggttatt ggatgagcaa 481    accagcaccc tcacaaggct gcgctactct taccgggtca tctgcagtga caactactat 541    ggagacaact gctcccgcct gtgcaagaag cgcaatgacc acttcggcca ctatgtgtgc 601    cagccagatg gcaacttgtc ctgcctgccc ggttggactg gggaatattg ccaacagcct 661    atctgtcttt cgggctgtca tgaacagaat ggctactgca gcaagccagc agagtgcctc 721    tgccgcccag gctggcaggg ccggctgtgt aacgaatgca tcccccacaa tggctgtcgc 781    cacggcacct gcagcactcc ctggcaatgt acttgtgatg agggctgggg aggcctgttt 841    tgtgaccaag atctcaacta ctgcacccac cactccccat gcaagaatgg ggcaacgtgc 901    tccaacagtg ggcagcgaag ctacacctgc acctgtcgcc caggctacac tggtgtggac 961    tgtgagctgg agctcagcga gtgtgacagc aacccctgtc gcaatggagg cagctgtaag 1021    gaccaggagg atgctaccac ctgcctgtgt cctccgggct actatggcct gcattgtgaa 1081    cacagcacct tgagctgcgc cgactccccc tgcttcaatg ggggctcctg ccgggagcgc
```

```
1141   aaccagggggg ccaactatgc ttgtgaatgt ccccccaact tcaccggctc caactgcgag
1201   aagaaagtgg acaggtgcac cagcaacccc tgtgccaacg ggggacagtg cctgaaccga
1261   ggtccaagcc gcatgtgccg ctgccgtcct ggattcacgg gcacctactg tgaactccac
1321   gtcagcgact gtgcccgtaa cccttgcgcc cacggtggca cttgccatga cctggagaat
1381   gggctcatgt gcacctgccc tgccggcttc tctggccgac gctgtgaggt gcggacatcc
1441   atcgatgcct gtgcctcgag tccctgcttc aacagggcca cctgctacac cgacctctcc
1501   acagacacct tgtgtgcaa ctgcccttat ggctttgtgg gcagccgctg cgagttcccc
1561   gtgggcttgc cgcccagctt ccctgggtg gccgtctcgc tgggtgtggg gctggcagtg
1621   ctgctggtac tgctgggcat ggtggcagtg gctgtgcggc agctgcggct tcgacggccg
1681   gacgacggca gcagggaagc catgaacaac ttgtcggact tccagaagga caacctgatt
1741   cctgccgccc agcttaaaaa cacaaaccag aagaaggagc tggaagtgga ctgtggcctg
1801   gacaagtcca actgtggcaa acagcaaaac cacacattgg actataatct ggccccaggg
1861   cccctggggc gggggaccat gccaggaaag tttccccaca gtgacaagag cttaggagag
1921   aaggcgccac tgcggttaca cagtgaaaag ccagagtgtc ggatatcagc gatatgctcc
1981   cccagggact ccatgtacca gtctgtgtgt ttgatatcag aggagaggaa tgaatgtgtc
2041   attgccacgg aggtataa
```

Delta-like ligand 4 amino acid sequence (AF253468.1)
SEQ ID NO: 2

MAAASRSASGWALLLLVALWQQRAAGSGVFQLQLQEFINERGVLASGRPCEPGCRTFERVCLKHFQAVVSPGPCT
FGTVSTPVLGTNSFAVRDDSSGGGRNPLQLPFNFTWPGTFSLIITEAWHAPGDDLRPEALPPDALISKIAIQGSLA
VGQNWLLDEQTSTLTRLRYSYRVICSDNYYGDNCSRLCKKRNDHFGHYVCQPDGNLSCLPGWTGEYCQQPICLSG
CHEQNGYCSKPAECLCRPGWQGRLCNECIPHNGCRHGTCSTPWQCTCDEGWGGLFCDQDLNYCTHHSPCKNGATC
SNSGQRSYTCTCRPGYTGVDCELELSECDSNPCRNGGSCKDQEDGYHCLCPPGYYGLHCEHSTLSCADSPCFNGG
SCRERNQGANYACECPPNFTGSNCEKKVDRCTSNPCANGGQCLNRGPSRMCRCRPGFTGTYCELHVSDCARNPCA
HGGTCHDLENGLMCTCPAGFSGRRCEVRTSIDACASSPCFNRATCYTDLSTDTFVCNCPYGFVGSRCEFPVGLPP
SFPWVAVSLGVGLAVLLVLLGMVAVAVRQLRLRRPDDGSREAMNNLSDFQKDNLIPAAQLKNTNQKKELEVDCGL
DKSNCGKQQNHTLDYNLAPGPLGRGTMPGKEPHSDKSLGEKAPLRLHSEKPECRISAICSPRDSMYQSVCLISEE
RNECVIATEV

E4bp4 gene sequence (X64318.1)
SEQ ID NO: 3

```
  1   gccccttttct ttctcctcgt cggcccgaga gcaggaacac gataacgaag gaggcccaac
 61   ttcattcaat aaggagcctg acggatttat cccagacggt agaacaaaag gaagaatatt
121   gatggatttt aaaccagagt ttttaaagag cttgagaata cggggaaatt aatttgttct
181   cctacacaca tagatagggt aaggttgttt ctgatgcagc tgagaaaaat gcagaccgtc
241   aaaaaggagc aggcgtctct tgatgccagt agcaatgtgg acaagatgat ggtccttaat
301   tctgctttaa cggaagtgtc agaagactcc acaacaggtg aggacgtgct tctcagtgaa
361   ggaagtgtgg ggaagaacaa atcttctgca tgtcggagga acgggaatt cattcctgat
421   gaaaagaaag atgctatgta ttgggaaaaa aggcggaaaa ataatgaagc tgccaaaaga
481   tctcgtgaga agcgtcgact gaatgacctg gttttagaga acaaactaat tgcactggga
541   gaagaaaacg ccactttaaa agctgagctg cttttcacta aaattaaagtt tggtttaatt
601   agctccacag catatgctca agagattcag aaactcagta attctacagc tgtgtacttt
661   caagattacc agacttccaa atccaatgtg agttcatttg tggacgagca cgaaccctcg
721   atggtgtcaa gtagttgtat ttctgtcatt aaacactctc cacaaagctc gctgtccgat
```

```
 781   gtttcagaag tgtcctcagt agaacacacg caggagagct ctgtgcaggg aagctgcaga
 841   agtcctgaaa acaagttcca gattatcaag caagagccga tggaattaga gagctacaca
 901   agggagccaa gagatgaccg aggctcttac acagcgtcca tctatcaaaa ctatatgggg
 961   aattctttct ctgggtactc acactctccc ccactactgc aagtcaaccg atcctccagc
1021   aactccccga gaacgtcgga aactgatgat ggtgtggtag gaaagtcatc tgatggagaa
1081   gacgagcaac aggtccccaa gggccccatc cattctccag ttgaactcaa gcatgtgcat
1141   gcaactgtgg ttaaagttcc agaagtgaat tcctctgcct tgccacacaa gctccggatc
1201   aaagccaaag ccatgcagat caaagtagaa gcctttgata tgaatttga ggccacgcaa
1261   aaactttcct cacctattga catgacatct aaaagacatt tcgaactcga aaagcatagt
1321   gccccaagta tggtacattc ttctcttact cctttctcag tgcaagtgac taacattcaa
1381   gattggtctc tcaaatcgga gcactggcat caaaaagaac tgagtggcaa aactcagaat
1441   agtttcaaaa ctggagttgt tgaaatgaaa gacagtggct acaaagtttc tgacccagag
1501   aacttgtatt tgaagcaggg gatagcaaac ttatctgcag aggttgtctc actcaagaga
1561   cttatagcca cacaaccaat ctctgcttca gactctgggt aaattactac tgagtaagag
1621   ctgggcattt agaaagatgt catttgcaat agagcagtcc attttgtatt atgctgaatt
1681   ttcactggac ctgtgatgtc atttcactgt gatgtgcaca tgttgtctgt ttggtgtctt
1741   tttgtgcaca gattatgatg aagattagat tgtgttatca ctctgcctgt gtatagtcag
1801   atagtcatat gcgtaaggct gtatatatta agnttttatt tttgttgttc tattataaag
1861   tgtgtaagtt accagtttca ataaggatt ggtgacaaac acagaaaaaa aaaaaaaaaa
1921   aaa
```

E4bp4 amino acid sequence (X64318.1)

SEQ ID NO: 4

MQLRKMQTVKKEQASLDASSNVDKMMVLNSALTEVSEDSTIGEDVLLSEGSVGKNKSSACRRKREFIPDEKKDAM
YWEKRRKNNEAAKRSREKRRLNDLVLENKLIALGEENATLKAELLSLKLKFGLISSTAYAQEIQKLSNSTAVYFQ
DYQTSKSNVSSFVDEHEPSMVSSSCISVIKHSPQSSLSDVSEVSSVEHTQESSVQGSCRSPENKFQIIKQEPMEL
ESYTREPRDDRGSYTASIYQNYMGNSFSGYSHSPPLLQVNRSSSNSPRISETDDGVVGKSSDGEDEQQVPKGPIH
SPVELKHVHATVVKVPEVNSSALPHKLRIKAKAMQIKVEAFDNEFEATQKLSSPIDMISKRHFELEKHSAPSMVH
SSLIPFSVQVINIQDWSLKSEHWHQKELSGKTQNSFKIGVVEMKDSGYKVSDPENLYLKQGIANLSAEVVSLKRL
IATQPISASDSG

REV-ERBα gene sequence (NM_021724.4)

SEQ ID NO: 5

```
   1   gggcacgagg cgctccctgg gatcacatgg tacctgctcc agtgccgcgt gcggcccggg
  61   aaccctgggc tgctggcgcc tgcgcagagc cctctgtccc agggaaaggc tcgggcaaaa
 121   ggcggctgag attggcagag tgaaatatta ctgccgaggg aacgtagcag ggcacacgtc
 181   tcgcctcttt gcgactcggt gcccgtttc tccccatcac ctacttactt cctggttgca
 241   acctctcttc ctctgggact tttgcaccgg gagctccaga ttcgccaccc cgcagcgctg
 301   cggagccggc aggcagaggc acccgtaca ctgcagagac ccgaccctcc ttgctacctt
 361   ctagccagaa ctactgcagg ctgattcccc tacacactc tctctgctct tcccatgcaa
 421   agcagaactc cgttgcctca acgtccaacc cttctgcagg gctgcagtcc ggccacccca
 481   agaccttgct gcagggtgct tcggatcctg atcgtgagtc gcggggtcca ctccccgccc
 541   ttagccagtg cccaggggc aacagcggcg atcgcaacct ctagtttgag tcaaggtcca
 601   gtttgaatga ccgctctcag ctggtgaaga catgacgacc ctggactcca acaacaacac
```

```
                                   -continued
 661      aggtggcgtc atcacctaca ttggctccag tggctcctcc ccaagccgca ccagccctga
 721      atccctctat agtgacaact ccaatggcag cttccagtcc ctgacccaag gctgtcccac
 781      ctacttccca ccatccccca ctggctccct cacccaagac ccggctcgct cctttgggag
 841      cattccaccc agcctgagtg atgacggctc cccttcttcc tcatcttcct cgtcgtcatc
 901      ctcctcctcc ttctataatg ggagccccc tgggagtcta caagtggcca tggaggacag
 961      cagccgagtg tcccccagca agagcaccag caacatcacc aagctgaatg gcatggtgtt
1021      actgtgtaaa gtgtgtgggg acgttgcctc gggcttccac tacggtgtgc acgcctgcga
1081      gggctgcaag ggcttttttcc gtcggagcat ccagcagaac atccagtaca aaaggtgtct
1141      gaagaatgag aattgctcca tcgtccgcat caatcgcaac cgctgccagc aatgtcgctt
1201      caagaagtgt ctctctgtgg gcatgtctcg agacgctgtg cgttttgggc gcatcccaa
1261      acgagagaag cagcggatgc ttgctgagat gcagagtgcc atgaacctgg ccaacaacca
1321      gttgagcagc cagtgcccgc tggagacttc acccacccag caccccaccc caggccccat
1381      gggcccctcg ccaccccctg ctccggtccc ctcaccctg gtgggcttct cccagtttcc
1441      acaacagctg acgcctccca gatccccaag ccctgagccc acagtggagg atgtgatatc
1501      ccaggtggcc cgggcccatc gagagatctt cacctacgcc catgacaagc tgggcagctc
1561      acctggcaac ttcaatgcca accatgcatc aggtagccct ccagccacca ccccacatcg
1621      ctgggaaaat cagggctgcc cacctgcccc caatgacaac aacacccttg ctgcccagcg
1681      tcataacgag gccctaaatg gtctgcgcca ggctccctcc tctacccctc ccacctggcc
1741      tcctggccct gcacaccaca gctgccacca gtccaacagc aacgggcacc gtctatgccc
1801      cacccacgtg tatgcagccc cagaaggcaa ggcacctgcc aacagtcccc ggcagggcaa
1861      ctcaaagaat gttctgctgg catgtcctat gaacatgtac ccgcatggac gcagtgggcg
1921      aacggtgcag gagatctggg aggatttctc catgagcttc acgcccgctg tgcgggaggt
1981      ggtagagttt gccaaacaca tcccgggctt ccgtgacctt ctcagcatg ccaagtcac
2041      cctgcttaag gctggcacct ttgaggtgct gatggtgcgc tttgcttcgt tgttcaacgt
2101      gaaggaccag acagtgatgt tcctaagccg caccacctac agcctgcagg agcttggtgc
2161      catgggcatg ggagacctgc tcagtgccat gttcgacttc agcgagaagc tcaactccct
2221      ggcgcttacc gaggaggagc tgggcctctt caccgcggtg gtgcttgtct ctgcagaccg
2281      ctcgggcatg gagaattccg cttcggtgga gcagctccag gagacgctgc tgcgggctct
2341      tcgggctctg gtgctgaaga accggccctt ggagacttcc cgcttcacca agctgctgct
2401      caagctgccg gacctgcgga ccctgaacaa catgcattcc gagaagctgc tgtccttccg
2461      ggtggacgcc cagtgacccg ccggccggc cttctgccgc tgccccttg tacagaatcg
2521      aactctgcac ttctctctcc tttacgagac gaaaaggaaa agcaaaccag aatcttattt
2581      atattgttat aaaatattcc aagatgagcc tctggccccc tgagccttct tgtaaatacc
2641      tgcctccctc ccccatcacc gaacttcccc tcctcccta tttaaaccac tctgtctccc
2701      ccacaaccct cccctggccc tctgatttgt tctgttcctg tctcaaatcc aatagttcac
2761      agctgagctg gcttcaaaaa aaaaaaaaa aaa
```
REV-ERBα amino acid sequence (NM_021724.4)

SEQ ID NO: 6
MTTLDSNNNTGGVITYIGSSGSSPSRTSPESLYSDNSNGSFQSLTQGCPTYFPPSPTGSLTQDPARSFGSIPPSL

SDDGSPSSSSSSSSSSSFYNGSPPGSLQVAMEDSSRVSPSKSTSNITKLNGMVLLCKVCGDVASGEHYGVHACE

GCKGFERRSIQQNIQYKRCLKNENCSIVRINRNRCQQCRFKKCLSVGMSRDAVREGRIPKREKQRMLAEMQSAMN

LANNQLSSQCPLETSPTQHPTPGPMGPSPPPAPVPSPLVGESQFPQQLTPPRSPSPEPTVEDVISQVARAHREIF

TYAHDKLGSSPGNFNANHASGSPPATTPHRWENQGCPPAPNDNNTLAAQRHNEALNGLRQAPSSYPPTWPPGPAH

HSCHQSNSNGHRLCPTHVYAAPEGKAPANSPRQGNSKNVLLACPMNMYPHGRSGRTVQEIWEDFSMSFTPAVREV

VEFAKHIPGFRDLSQHDQVTLLKAGTFEVLMVRFASLFNVKDQTVMFLSRTTYSLQELGAMGMGDLLSAMFDFSE

KLNSLALTEEELGLETAVVLVSADRSGMENSASVEQLQETLLRALRALVLKNRPLETSRFTKLLLKLPDLRTLNN

MHSEKLLSFRVDAQ

REV-ERBβ gene sequence (AB307693.1)

SEQ ID NO: 7

```
   1   atggaggtga atgcaggagg tgtgattgcc tatatcagtt cttccagctc agcctcaagc
  61   cctgcctctt gtcacagtga gggttctgag aatagtttcc agtcctcctc ctcttctgtt
 121   ccatcttctc caaatagctc taattctgat accaatggta atcccaagaa tggtgatctc
 181   gccaatattg aaggcatctt gaagaatgat cgaatagatt gttctatgaa aacaagcaaa
 241   tcgagtgcac ctgggatgac aaaaaatcat agtggtgtga caaaatttag tggcatggtt
 301   ctactgtgta aagtctgtgg ggatgtggcg tcaggattcc actatggagt tcatgcttgc
 361   gaaggctgta agggtttctt tcggagaagt attcaacaaa acatccagta caagaagtgc
 421   ctgaagaatg aaaactgttc tataatgaga atgaatagga acagatgtca gcaatgtcgc
 481   ttcaaaaagt gtctgtctgt tggaatgtca agagatgctg ttcggtttgg tcgtattcct
 541   aagcgtgaaa acagaggat gctaattgaa atgcaaagtg caatgaagac catgatgaac
 601   agccagttca gtggtcactt gcaaaatgac acattagtag aacatcatga acagacagcc
 661   ttgccagccc aggaacagct gcgacccaag ccccaactgg agcaagaaaa catcaaaagc
 721   tcttctcctc catcttctga ttttgcaaag gaagaagtga ttggcatggt gaccagagct
 781   cacaaggata ccttatgta taatcaagag cagcaagaaa actcagctga gagcatgcag
 841   ccccagagag agaacggat tcccaagaac atggagcaat ataatttaaa tcatgatcat
 901   tgcggcaatg gcttagcag ccatttccc tgtagtgaga gccagcagca tctcaatgga
 961   cagttcaaag ggaggaatat aatgcattac ccanatggcc atgccatttg tattgcaaat
1021   ggacattgta tgaacttctc caatgcttat actcaaagag tatgtgatag agttccgata
1081   gatggatttt ctcagaatga aacaagaat agttacctgt gcaacactgg aggaagaatg
1141   catctggttt gtccaatgag taagtctcca tatgtggatc ctcataaatc aggacatgaa
1201   atctgggaag aattttcgat gagcttcact ccagcagtga agaagtggt ggaatttgca
1261   aagcgtattc ctgggttcag agatctctct cagcatgacc aggtcaacct tttaaaggct
1321   gggactttg aggttttaat ggtacggttc gcatcattat ttgatgcaaa ggaacgtact
1381   gtcacctttt aagtggaaa gaaatatagt gtggatgatt tacactcaat gggagcaggg
1441   gatctgctaa actctatgtt tgaatttagt gagaagctaa atgccctcca acttagtgat
1501   gaagagatga gtttgtttac agctgttgtc ctggtatctg cagatcgatc tggaatagaa
1561   aacgtcaact ctgtggaggc tttgcaggaa actctcattc gtgcactaag gaccttaata
1621   atgaaaaacc atccaaatga ggcctctatt tttacaaaac tgcttctaaa gttgccagat
1681   cttcgatctt taaacaacat gcactctgag gagctcttgg cctttaaagt tcacccttaa
```

REV-ERBβ amino acid sequence (AB307693.1)

SEQ ID NO: 8

MEVNAGGVIAYISSSSSASSPASCHSEGSENSFQSSSSSVPSSPNSSNSDTNGNPKNGDLANIEGILKNDRIDCS

MKTSKSSAPGMTKNHSGVTKFSGMVLLCKVCGDVASGFHYGVHACEGCKGFFRRSIQQNIQYKKCLKNENCSIMR

MNRNRCQQCRFKKCLSVGMSRDAVREGRIPKREKQRMLIEMQSAMKTMMNSQFSGHLQNDTLVEHHEQTALPAQE

QLRPKPQLEQENIKSSSPPSSDFAKEEVIGMVTRAHKDTFMYNQEQQENSAESMQPQRGERIPKNMEQYNLNHDH

-continued

```
CGNGLSSHFPCSESQQHLNGQFKGRNIMHYPXGHAICIANGHCMNFSNAYTQRVCDRVPIDGFSQNENKNSYLCN

TGGRMHLVCPMSKSPYVDPHKSGHEIWEEFSMSFTPAVKEVVEFAKRIPGFRDLSQHDQVNLLKAGTFEVLMVRF

ASLFDAKERTVTELSGKKYSVDDLHSMGAGDLLNSMFEFSEKLNALQLSDEEMSLFTAVVLVSADRSGIENVNSV

EALQETLIRALRTLIMKNHPNEASIFTKLLLKLPDLRSLNNMHSEELLAFKVH
``` forward primer A for detection of E4bp4 wildtype allele  
SEQ ID NO: 9  
CTCTGAGCTTGGCTGATGTG reverse primer for the detection of E4bp4  
SEQ ID NO: 10  
GCTTCAAGTCTCCACCAAGC primer for the detection of the E4bp4 null allele  
SEQ ID NO: 11  
CCATGCTCCTGTCTTGATGA side chain on SUMO modified peptide  
SEQ ID NO: 12  
GGTQQQFV mouse E4bp4 peptide comprising potential SUMO modification site  
SEQ ID NO: 13  
MQLRKMQTIKKEPAPLDPTS rat E4bp4 peptide comprising potential SUMO modification site  
SEQ ID NO: 14  
MQLRKMQAIKKEPASLDPTG human E4bp4 peptide comprising potential SUMO modification site  
SEQ ID NO: 15  
MQLRKMQTVKKEQASLDASS chicken E4bp4 peptide comprising potential SUMO modification site  
SEQ ID NO: 16  
MQLRKMQTLKKEHGSVDTSS Xenopus E4bp4 peptide comprising potential SUMO modification site  
SEQ ID NO: 17  
MPTIKKEQECADSRM mouse E4bp4 peptide comprising potential SUMO modification site  
SEQ ID NO: 18  
LENKLIALGEENATLKAELL rat E4bp4 peptide comprising potential SUMO modification site  
SEQ ID NO: 19  
LENKLIALGEENATLKAELL human E4bp4 peptide comprising potential SUMO modification site  
SEQ ID NO: 20  
LENKLIALGEENATLKAELL chicken E4bp4 peptide comprising potential SUMO modification site  
SEQ ID NO: 21  
LENKLIALGEENATLKAELL Xenopus E4bp4 peptide comprising potential SUMO modification site  
SEQ ID NO: 22  
LENKLIALGEENASLKTELL mouse E4bp4 peptide comprising potential SUMO modification site  
SEQ ID NO: 23  
PENKFPVIKQEPVELESFAR rat E4bp4 peptide comprising potential SUMO modification site  
SEQ ID NO: 24  
PENKFPVIKQEPVELESFAR human E4bp4 peptide comprising potential SUMO modification site  
SEQ ID NO: 25  
PENKFQIIKQEPMELESYTR chicken E4bp4 peptide comprising potential SUMO modification site  
SEQ ID NO: 26  
PENKFQIIKQEPIELER -continued Xenopus E4bp4 peptide comprising potential SUMO modification site
SEQ ID NO: 27
TDIKSQRIKQEQMEAGNFSR mouse E4bp4 peptide comprising potential SUMO modification site
SEQ ID NO: 28
RIKAKAMQVKVEALDSEFEG rat E4bp4 peptide comprising potential SUMO modification site
SEQ ID NO: 29
RIKAKAMQVKVEALDSEFEG human E4bp4 peptide comprising potential SUMO modification site
SEQ ID NO: 30
RIKAKAMQIKVEAFDNEFEA chicken E4bp4 peptide comprising potential SUMO modification site
SEQ ID NO: 31
RIKAKAMQVKVEAMDNDYDA Xenopus E4bp4 peptide comprising potential SUMO modification site
SEQ ID NO: 32
RIKAKAMQIKVESLESELNS mouse E4bp4 peptide comprising potential SUMO modification site
SEQ ID NO: 33
VTNIQDWSLKSEHWHHKELS rat E4bp4 peptide comprising potential SUMO modification site
SEQ ID NO: 34
VTNIQDWSLRSEHWHHKELG human E4bp4 peptide comprising potential SUMO modification site
SEQ ID NO: 35
VTNIQDWSLKSEHWHQKELS chicken E4bp4 peptide comprising potential SUMO modification site
SEQ ID NO: 36
VTNIQDWSLKPELWHQKELN Xenopus E4bp4 peptide comprising potential SUMO modification site
SEQ ID NO: 37
VTNIQDWPLKPGQWHHRELE Forward primer for amplification of putative E4bp4-binding regions in Notch1 locus
SEQ ID NO: 38
CTATATTTTTGCCTTGACAGCTAAAGG Reverse primer for amplification of putative E4bp4-binding regions in Notch1 locus
SEQ ID NO: 39
GAAGTACGAAGCATGCTTGC Forward primer for amplification of putative E4bp4-binding regions in Notch1 locus
SEQ ID NO: 40
CACATCTGTGAGCTATTTTGG Reverse primer for amplification of putative E4bp4-binding regions in Notch1 locus
SEQ ID NO: 41
GACTGACTAAACTAACATTCCCAC Forward primer for amplification of putative E4bp4-binding regions in Notch1 locus
SEQ ID NO: 42
CTCAGAAACTGGCCTCAAGC Reverse primer for amplification of putative E4bp4-binding regions in Notch1 locus
SEQ ID NO: 43
CACTTGCAGTCAGGCGTTC Forward primer for amplification of putative E4bp4-binding regions in Notch1 locus
SEQ ID NO: 44
CACGCCATCTTAAAGAGCTC Reverse primer for amplification of putative E4bp4-binding regions in Notch1 locus
SEQ ID NO: 45
GTAACCAACTGCACTCTTCTCC Forward primer for amplification of putative E4bp4-binding regions in Notch1 locus
SEQ ID NO: 46
CACCAAGAATTCCCAGGAG -continued Reverse primer for amplification of putative E4bp4-binding regions in Notch1 locus
SEQ ID NO: 47

GAGTGCAGTCACGTGCTGAC

Forward primer for amplification of putative E4bp4-binding regions in Notch1 locus
SEQ ID NO: 48

CTCAGACTCTCTCGGTAAGTGTC

Reverse primer for amplification of putative E4bp4-binding regions in Notch1 locus
SEQ ID NO: 49

CGTGTGGAGCTACTCTGGC

Human Notch1 cDNA sequence (CR457221.1)
SEQ ID NO: 50

```
  1    atgtcaaaca tgagatgtgt ggactgtggc acttgcctgg gtcacacacg gaggcatcct 61    acccttttct ggggaaagac actgcctggg ctgaccccgg tggcggcccc agcacctcag 121    cctgcacagt gtcccccagg ttccgaagaa gatgctccag caacacagcc tgggcccag 181    ctcgcgggac ccgaccccc gtgggctccc gtgttttgta ggagacttgc cagagccggg 241    cacattgagc tgtgcaacgc cgtgggctgc gtcctttggt cctgtccccg cagccctggc 301    aggggggcatg cggtcgggca ggggctggag ggaggcgggg gctgcccttg ggccacccct 361    cctagtttgg gaggagcaga ttttttgcaat accaagtata gcctatggca gaaaaaatgt 421    ctttaa
```

Human Notch1 protein sequence (CR457221.1)
SEQ ID NO: 51

MSNMRCVDCGTCLGHTRRHPTLFWGKTLPGLTPVAAPAPQPAQCPPGSEEDAPATQPGPQLAGPDPPWAPVFCRR

LARAGHIELCNAVGCVLWSCPRSPGRGHAVGQGLEGGGGCPWATPPSLGGADFCNTKYSLWQKKCL

EXAMPLES

The invention will be further clarified by the following examples, which are intended to be purely exemplary of the invention and are in no way limiting.

Example 1—E4bp4 is SUMOlylated

To investigate how E4bp4 protein functions might be regulated, a yeast-two-hybrid screen was performed to try to identify binding partners for the E4bp4 protein. Eleven proteins received multiple hits in the screen, but the protein with the highest number of positive identifications was PIAS1 (Table 1). PIAS1 is a small ubiquitin-like modifier (SUMO) E3 ligase required for the addition of post-translational SUMO modifications, suggesting that E4bp4 may be post-translationally SUMOylated.

TABLE 1

E4bp4 interacting partners from yeast-two-hybrid screen.

| Gene Name | Positive clones | Protein function |
|---|---|---|
| C18orf25 | 1 | Unknown |
| CHD1 | 1 | DNA helicase binding protein |
| DSP | 2 | Cytoskeletal protein |
| FLJ13057 | 5 | Unknown |
| FLJ544447 | 1 | Unknown |
| FLNA | 1 | Cytoskeletal protein |
| HIPK1 | 1 | Serine/threonine protein kinase |
| HIPK3 | 5 | Serine/threonine protein kinase |
| PIAS1 | 20 | SUMO E3 ligase |
| PIAS3 | 2 | SUMO E3 ligase |
| RANBP2 | 1 | SUMO E3 ligase |
| RNF111 | 1 | SUMO-targeted ubiquitin ligase |
| SETX | 2 | DNA helicase |
| SNRP70 | 2 | Splicesomal ribonucleoprotein |
| SORL1 | 1 | Neuronal apolipoprotein E receptor |

TABLE 1-continued

E4bp4 interacting partners from yeast-two-hybrid screen.

| Gene Name | Positive clones | Protein function |
|---|---|---|
| TLK2 | 2 | Tousled-like serine/threonine kinase |
| U5-200KD | 1 | RNA helicase |
| ZBTB16 | 1 | Zinc finger transcription factor |
| ZMYM5 | 5 | Zinc Finger MYM-Type Protein |
| ZNF198 | 5 | Zinc Finger Transcriptional cofactor |
| ZNF237 | 5 | Zinc Finger Transcriptional cofactor |

Figure 2:
FIG. 2: (A) E4bp4 was expressed in HeLa cells stably expressing 6His-SUMO1, 6His-SUMO2 or 6His-SUMO3. Protein extracts were purified by $Ni^{2+}$ affinity chromatography under denaturing conditions and analysed by Western blot. Input samples were lysed in Laemlli sample buffer and directly compared. (B) FLAG-E4bp4 was expressed in 6His-SUMO1, 6His-SUMO2 and 6His-SUMO3 HeLa cells and anti-FLAG antibody was used to immunoprecipitate E4bp4 before Western blot analysis. Grey arrows indicate unmodified E4bp4 and black arrows indicate SUMO modified forms of E4bp4 with higher molecular weights. Both are representative of three independent experiments.
Figure 2:
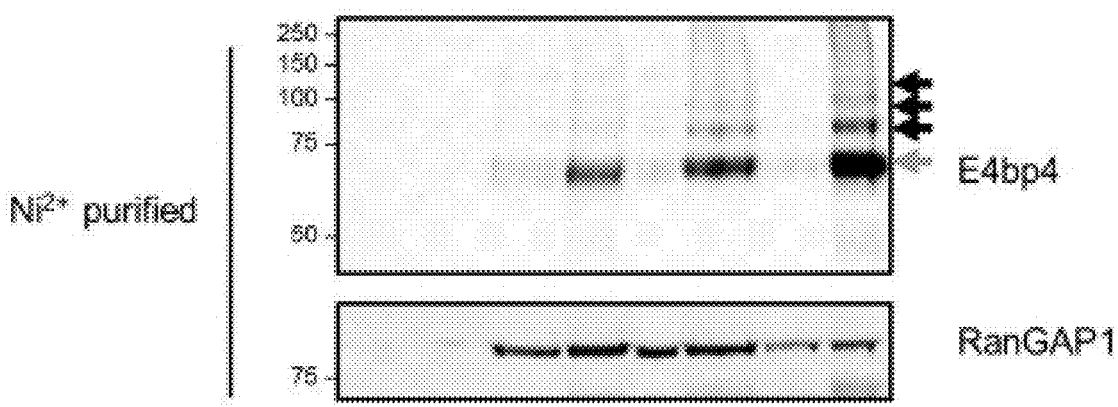
Figure 2:
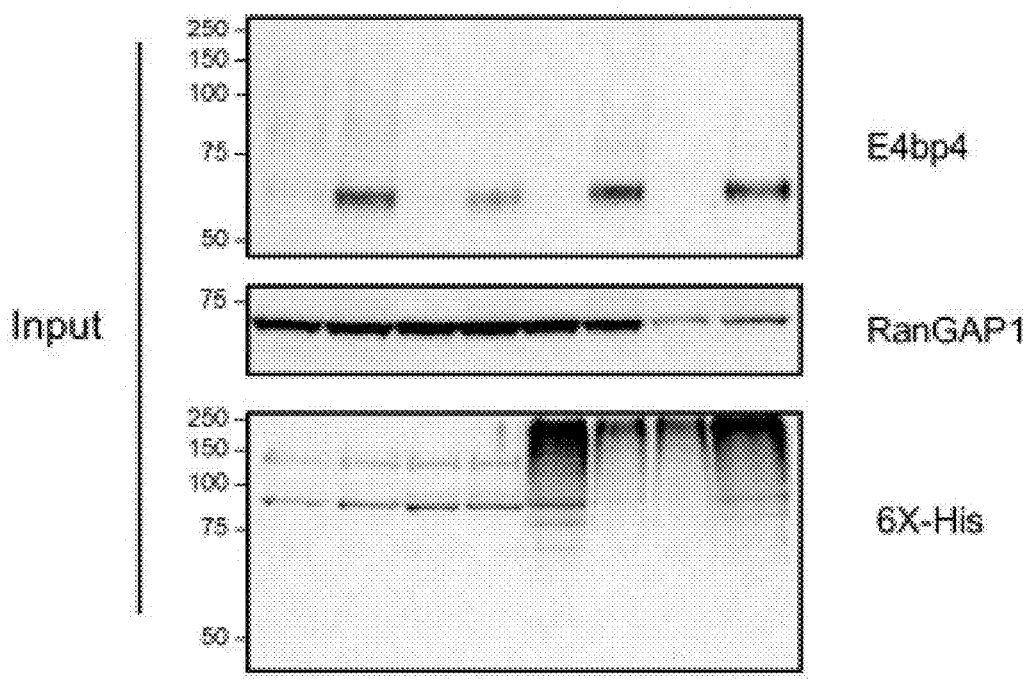
Figure 2:
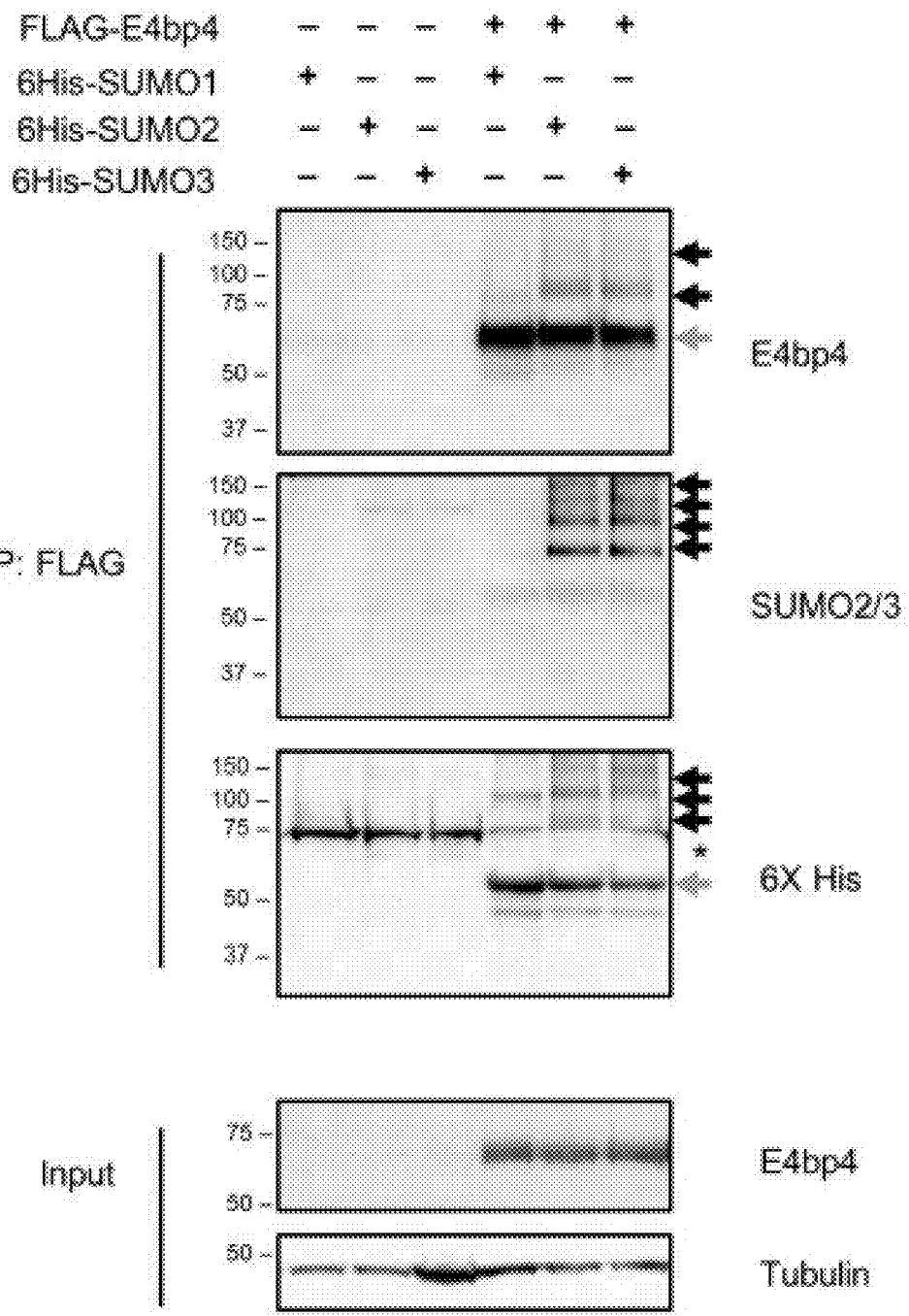

SUMO proteins are reversible post-translational protein modifiers and mammals express four SUMO isoforms, designated SUMO1 to SUMO4. Mature SUMO2 and SUMO3 proteins differ by only three amino acids and are functionally homologous, whilst SUMO4 cannot be efficiently processed in mammalian cells and is not thought to be functional. E4bp4 was expressed in HeLa cells stably expressing 6His-SUMO1, 6His-SUMO2 and 6His-SUMO3 and, following enrichment of all SUMOylated proteins by $Ni^{2+}$ affinity chromatography, higher molecular weight forms of E4bp4 were observed (FIG. 2A). Each SUMO conjugate adds 10-15 kDa onto the apparent molecular weight of a protein, so the higher molecular weight forms of E4bp4 correspond to multiply SUMOylated versions of the protein. FLAG tagged E4bp4 was also expressed in each 6His-SUMO HeLa cell line and purified using anti-FLAG affinity resin and the same multiple higher molecular weight forms of E4bp4 were observed in the presence of 6His-SUMO2 and 6His-SUMO3 (FIG. 21B).

Figure 3:
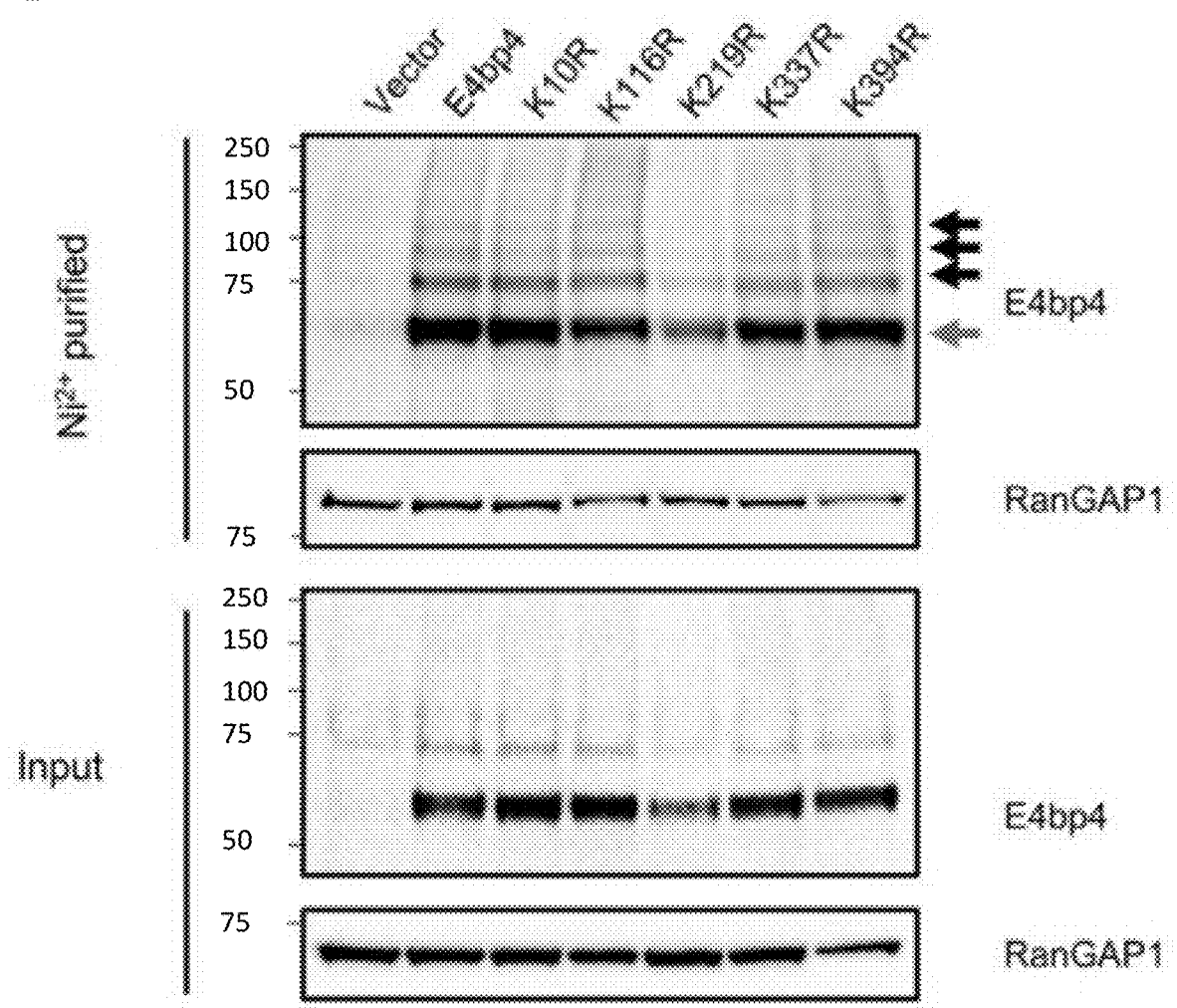
FIG. 3: (A) Sites of potential E4bp4 SUMO modification based on the presence of the ψJ-K-x-E motif. Asterisks highlight perfectly conserved residues and dots highlight partially conserved residues. Position of last amino acid in sequence indicated. (B) Mutant versions of E4bp4 lacking SUMOylation sites (lysine to arginine point mutations) were expressed in 6His-SUMO2 HeLa cells and protein extracts were purified by $Ni^{2+}$ affinity chromatography under denaturing conditions and analysed by Western blots. Grey arrows highlight unmodified E4bp4 and black arrows highlight SUMO modified forms of E4bp4 with higher molecular weights, representative of three independent experiments. (C) Mass spectrometry identification of E4bp4 peptide SUMO2/3 modified at K219. FLAG-E4bp4 was expressed in 293T cells, purified from whole cell lysate using anti-FLAG immunoprecipitation and subjected to sequential digest by trypsin and Glu-C. E4bp4 peptides were purified and analysed by LC-MS/MS and SUMOylated peptides were identified by the presence of a GGTQQQFV modification on a lysine side chain. Annotated CID tandem mass spectra of +2 ion at m/z 853.95, with schematic representation of the identified peptide shown with detected b and y ions labelled from the fragmentation of E4bp4 peptide and SUMO tag.
Figure 3:
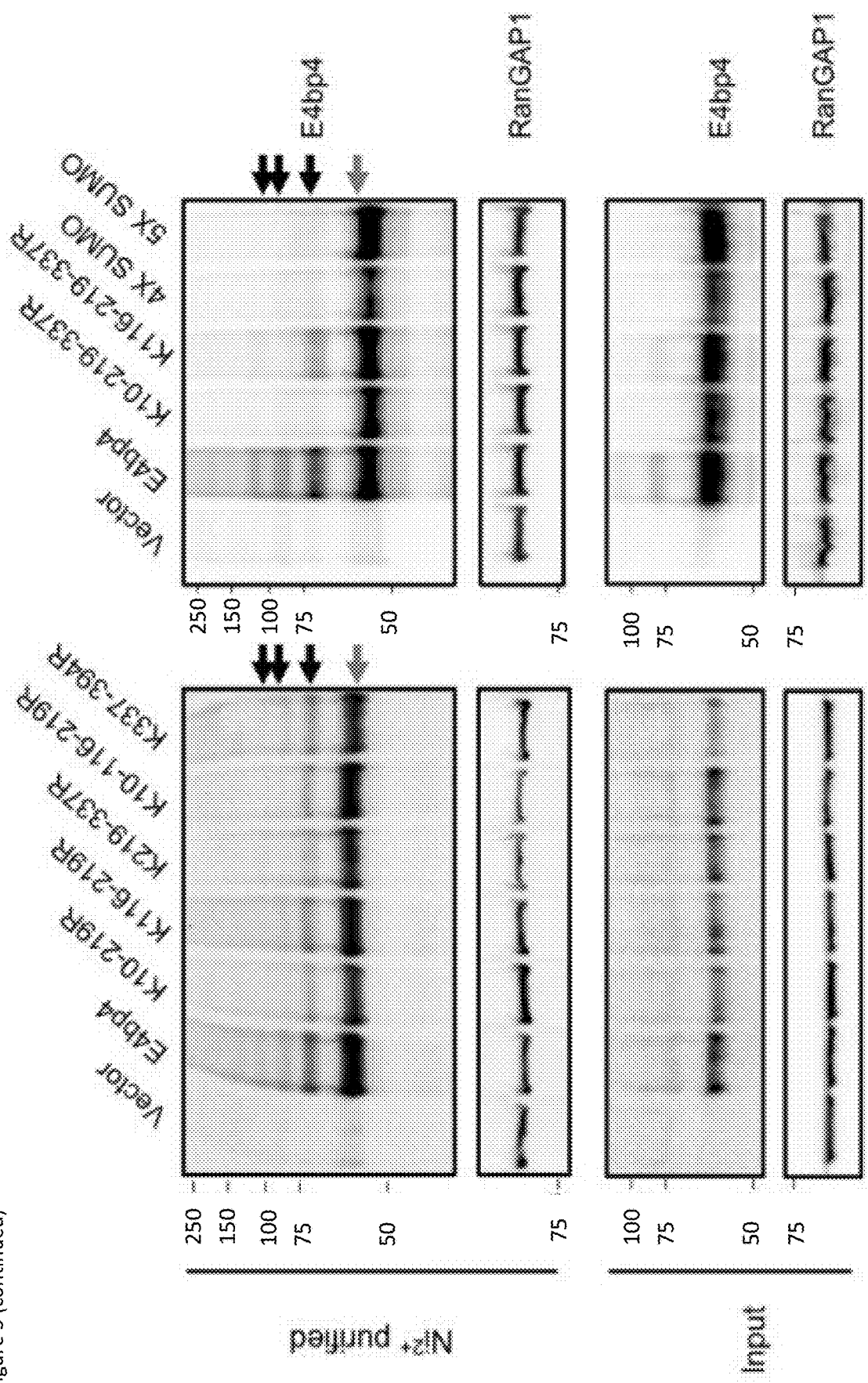
Figure 3:
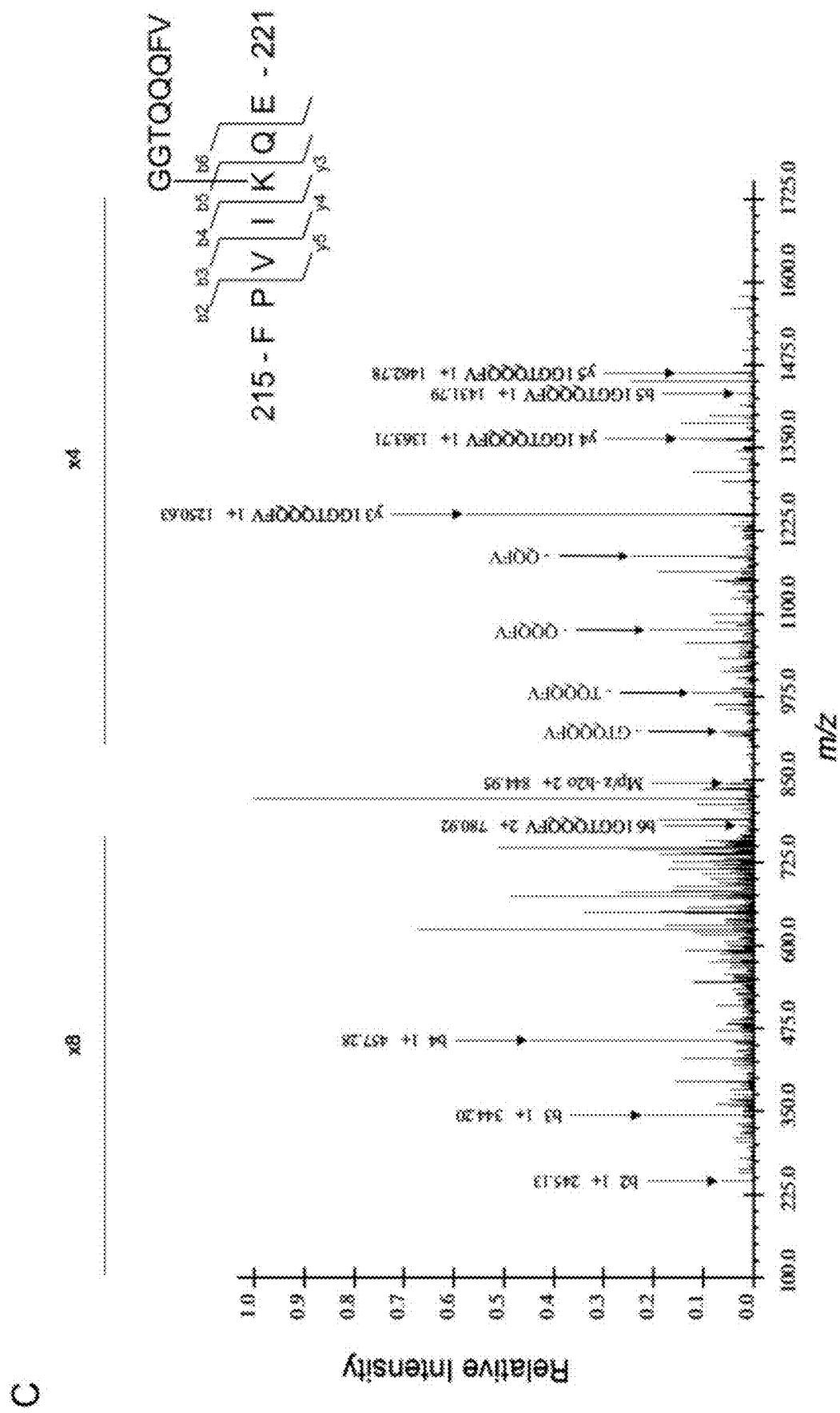

E4bp4 was examined for the presence of the SUMOylation consensus motif ψ-K-x-E in its primary amino acid sequence (FIG. 3A). Five potential modification sites were discovered that were all highly conserved across a range of species (FIG. 3A). To establish if any of these sites were SUMOylated, the central lysine residue at each site was individually mutated to an arginine in the E4bp4 cDNA by site-directed mutagenesis. This mutation abolishes any SUMO modification at that site while maintaining the structural integrity of the protein. To assess the effect of the mutations, each SUMO mutant was expressed in the 6His-SUMO2 HeLa cells (FIG. 3B). E4bp4-K219R was the only individual mutant to affect the SUMOylation of E4bp4, but it did not fully remove all E4bp4 SUMOylation (FIG. 3B). All multi-site mutants affected SUMOylation of E4bp4, in particular, the 5x-SUMO mutant lacking all 5 putative SUMOylation sites, had no higher molecular weight forms of E4bp4 (FIG. 3B).

To confirm the presence of SUMO modifications, purified E4bp4 protein was analysed by mass spectrometry (MS). Studying SUMO modifications by MS is challenging as SUMOylated forms of a protein are generally low in abundance and standard trypsin cleavage results in long SUMO peptide 'tails' remaining conjugated to target peptides, making them difficult to detect in standard MS21. A system was developed where FLAG epitope-tagged E4bp4 protein was expressed in 293T cells, purified by immunoprecipitation and sequentially digested with both trypsin and Glu-C. This novel double digest strategy aimed to produce short E4bp4 peptides with reduced SUMO isopeptide side chains on modified peptides. Using this approach a SUMO modified peptide was predicted to have a -GGTQQQFV side chain attached to a modified lysine. MS/MS analysis readily identified an E4bp4 peptide with a SUMO modification at K219, further confirming the presence of this POST-TRANSLATIONAL MODIFICATION (PTM) (FIG. 3C). These data demonstrated that the E4bp4 protein has SUMO modifications.

Example 2—SUMOylation of E4bp4 Influences NK Cell Development

The potential effect of these SUMO modifications on E4bp4's function as a transcription factor in NK cell development was then investigated.

Figure 4:
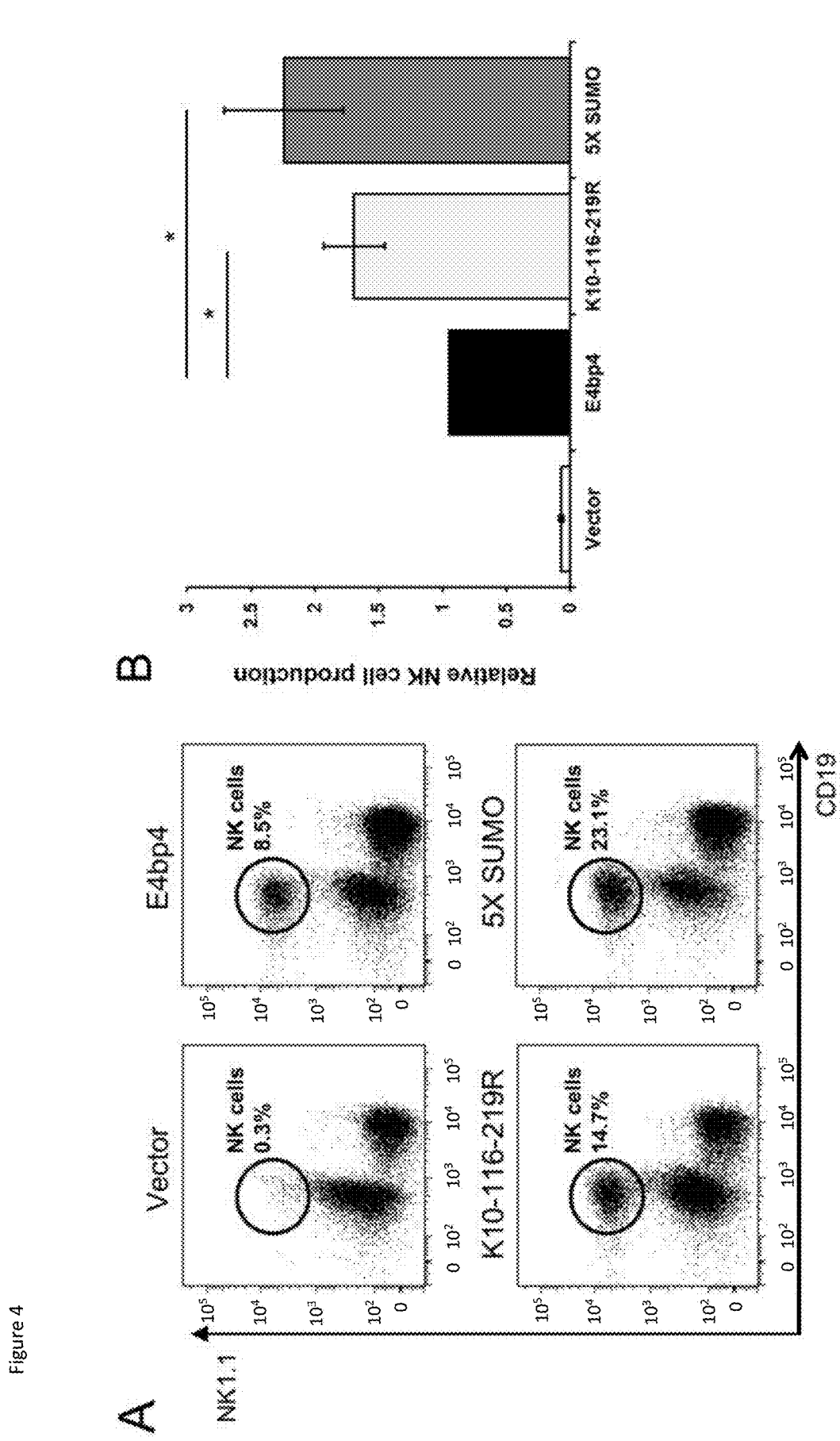
FIG. 4: $Lin^-$ BM cells were isolated from E4bp4$^{-/-}$ (A) or E4bp4+/+(C) mouse BM and cultured for two days in the presence of IL-7, Flt3-L and SCF before retroviral transduction with a MSCV-IRES-hCD2 construct. Transduced cells were cultured for three days, before being transferred onto OP9 stromal cells and cultured in the presence of IL-15 for 7 days. (A, C) Flow cytometry analysis identified hCD2+ (transduced) cells and the presence of NK1.1$^+$CD19$^-$ NK cells. (B, D) Relative levels of NK cell production between E4bp4 mutants normalised to WT-form E4bp4 (B) or empty vector (D). Data are representative of four independent experiments for each mutant. Error bars show SEM. *, P<0.05.
Figure 4:
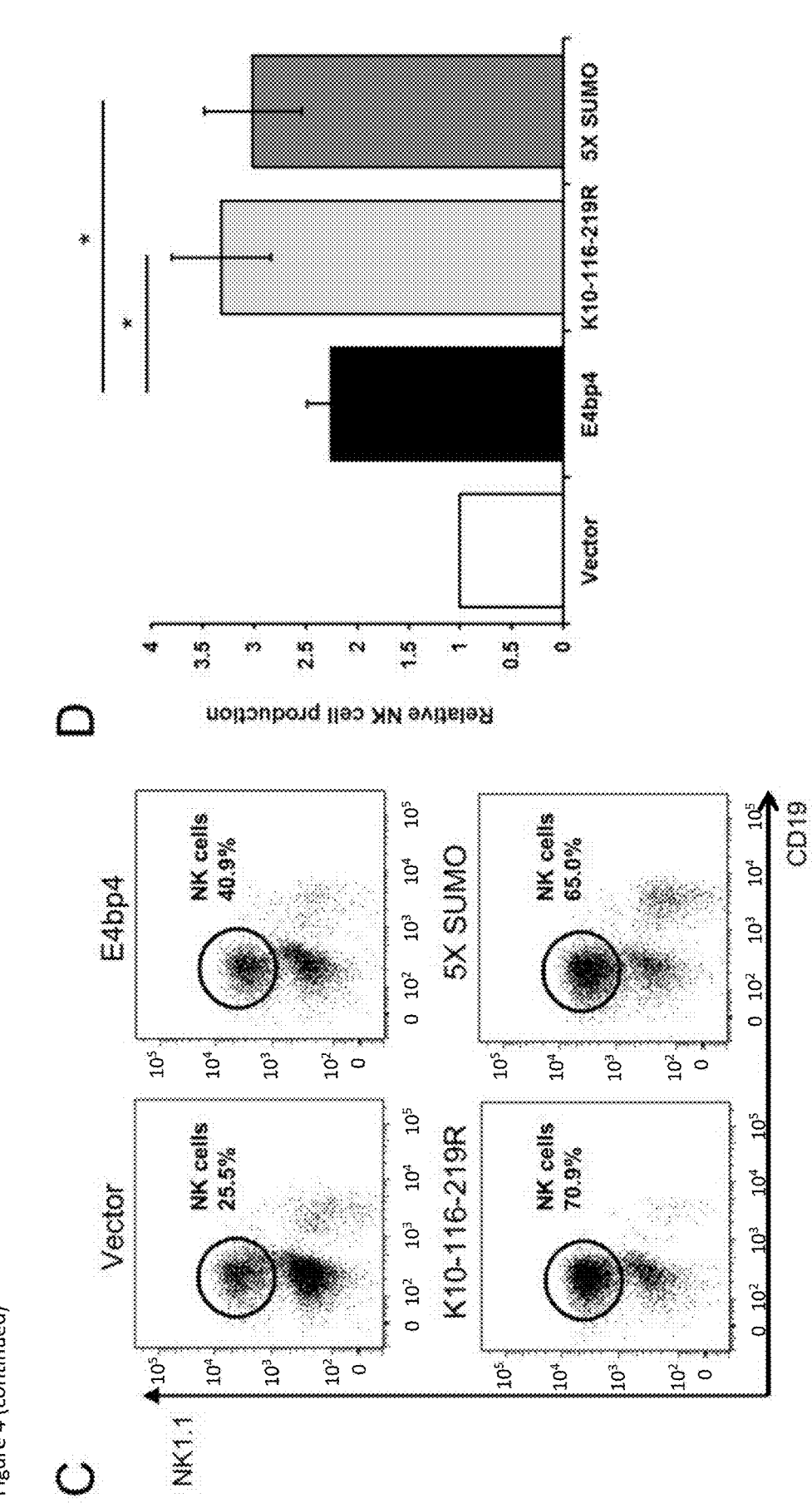

SUMOylation can affect the function of a transcription factor in different ways: cellular localisation; interactions with other proteins or; ability to regulate the expression of target genes. As E4bp4 is critical for the development of NK cells, it was postulated that SUMOylation may regulate this function. Therefore, the ability of E4bp4 to promote NK cell development with and without SUMO modifications was compared. Lineage negative (Lin⁻) BM cells were isolated from E4bp4$^{-/-}$ mice and transduced with a retrovirus expressing either the WT-form of E4bp4 or one of the E4bp4 mutants lacking SUMO modification sites. WT-form E4bp4 rescued NK cell development from E4bp4$^{--}$ Lin⁻ BM cells as previously reported, however, the number of NK cells produced was significantly higher when the cells expressed E4bp4 SUMOylation mutants (FIG. 4A-C). As the number of NK cells produced can vary between assays, the percentage of NK cells produced by each mutant was normalised to the positive control condition (i.e. WT-form E4bp4) (FIG. 4B). The same assay was also performed using E4bp4$^{+/+}$ Lin⁻ BM cells. In the E4bp4$^{+/+}$ Lin⁻ BM cells, expression of WT-form E4bp4 increased the level of NK cell production compared to the empty vector, but again the expression of E4bp4 SUMO mutants led to significantly greater levels of NK cell production (FIG. 4C,D). These findings showed that SUMOylation can influence the function of E4bp4 and in its absence the activity of E4bp4, as measured by NK cell output, is substantially increased.

Figure 5:
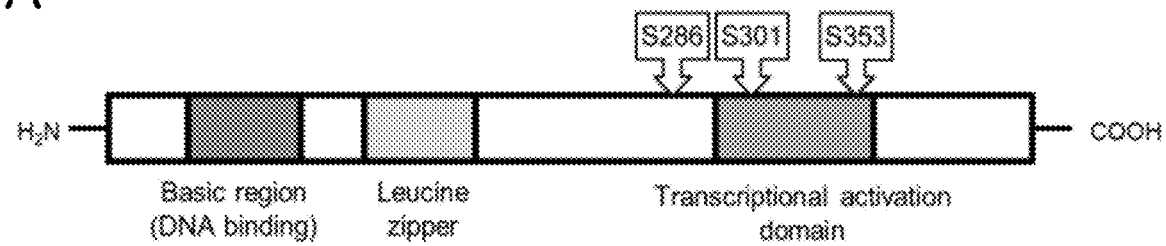
FIG. 5: (A) Schematic representation of the E4bp4 protein showing the positions of phosphorylation sites identified by LC-MS/MS. Conserved domain structure of E4bp4 shown (not to scale), which has been identified through sequence homology and mutational studies50. (B, D) Lin-BM cells were isolated from E4bp4$^{-/-}$ (B) or E4bp4$^{+/+}$ (D) mouse BM and cultured for two days in the presence of IL-7, Flt3-L and SCF before retroviral transduction with a MSCV-IRES-hCD2 construct. Transduced cells were cultured for three days, before being transferred onto OP9 stromal cells and cultured in the presence of IL-15 for 7 days. Flow cytometry analysis identified hCD2$^+$ (transduced) cells and the presence of NK1.1$^+$ CD19$^-$ NK cells. (C, E) Relative levels of NK cell production between E4bp4 mutants normalised to WT-form E4bp4 (C) or empty vector (E). Data are representative of three independent experiments for each mutant. Error bars show SEM. *, P<0.05.
Figure 5:
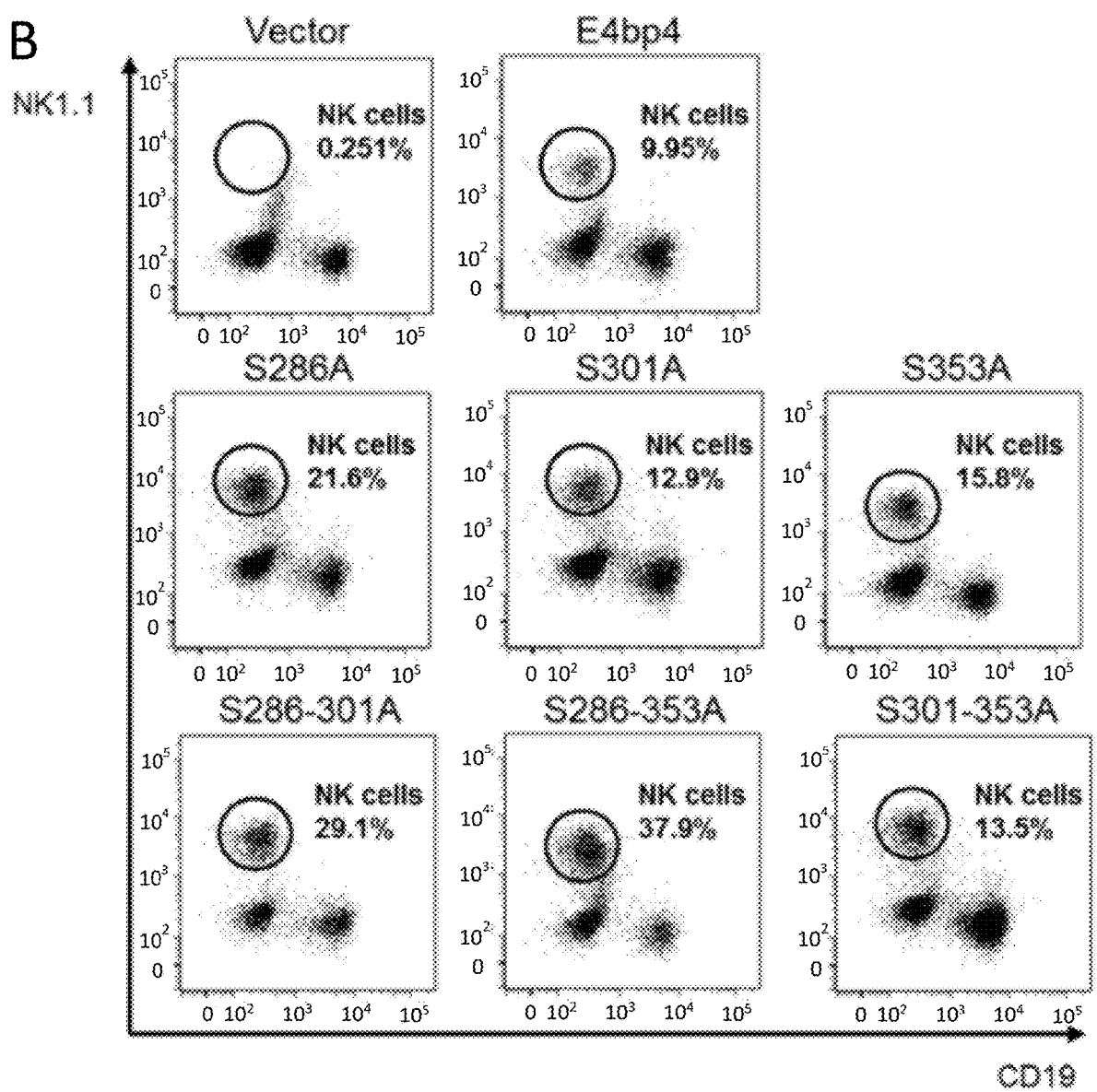
Figure 5:
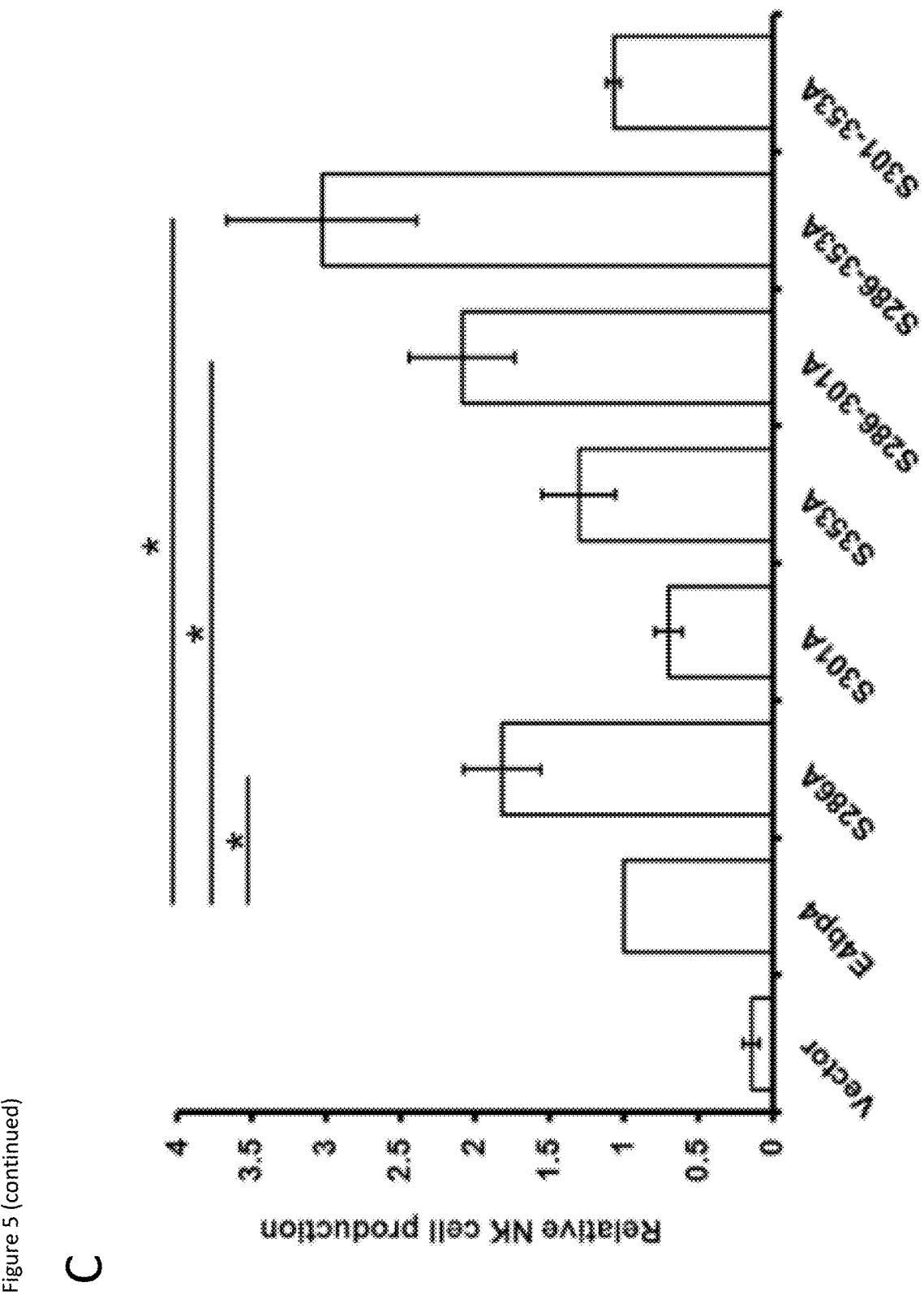
Figure 5:
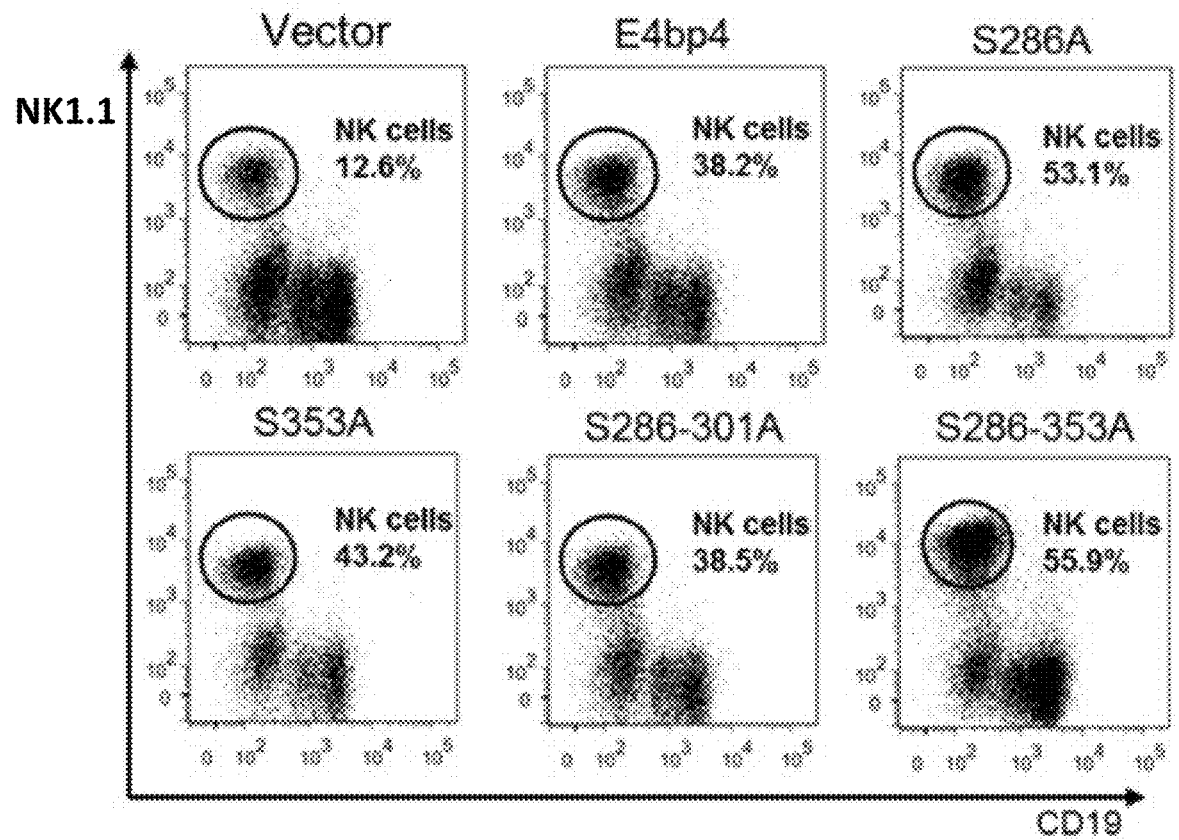
Figure 5:
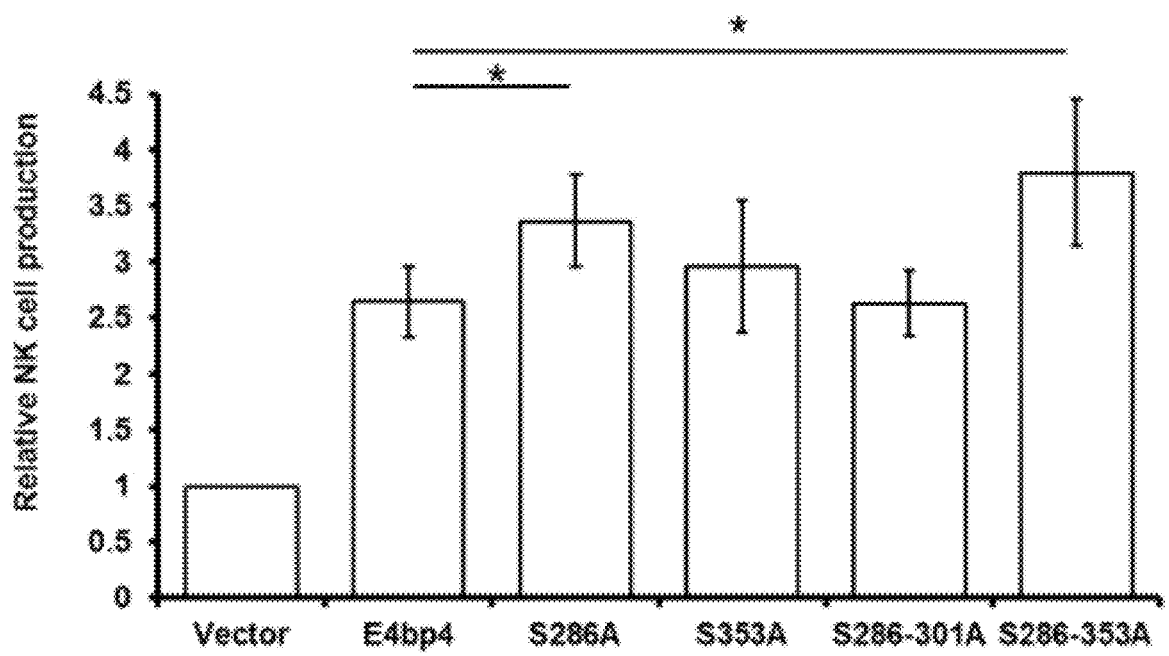
Figure 6:
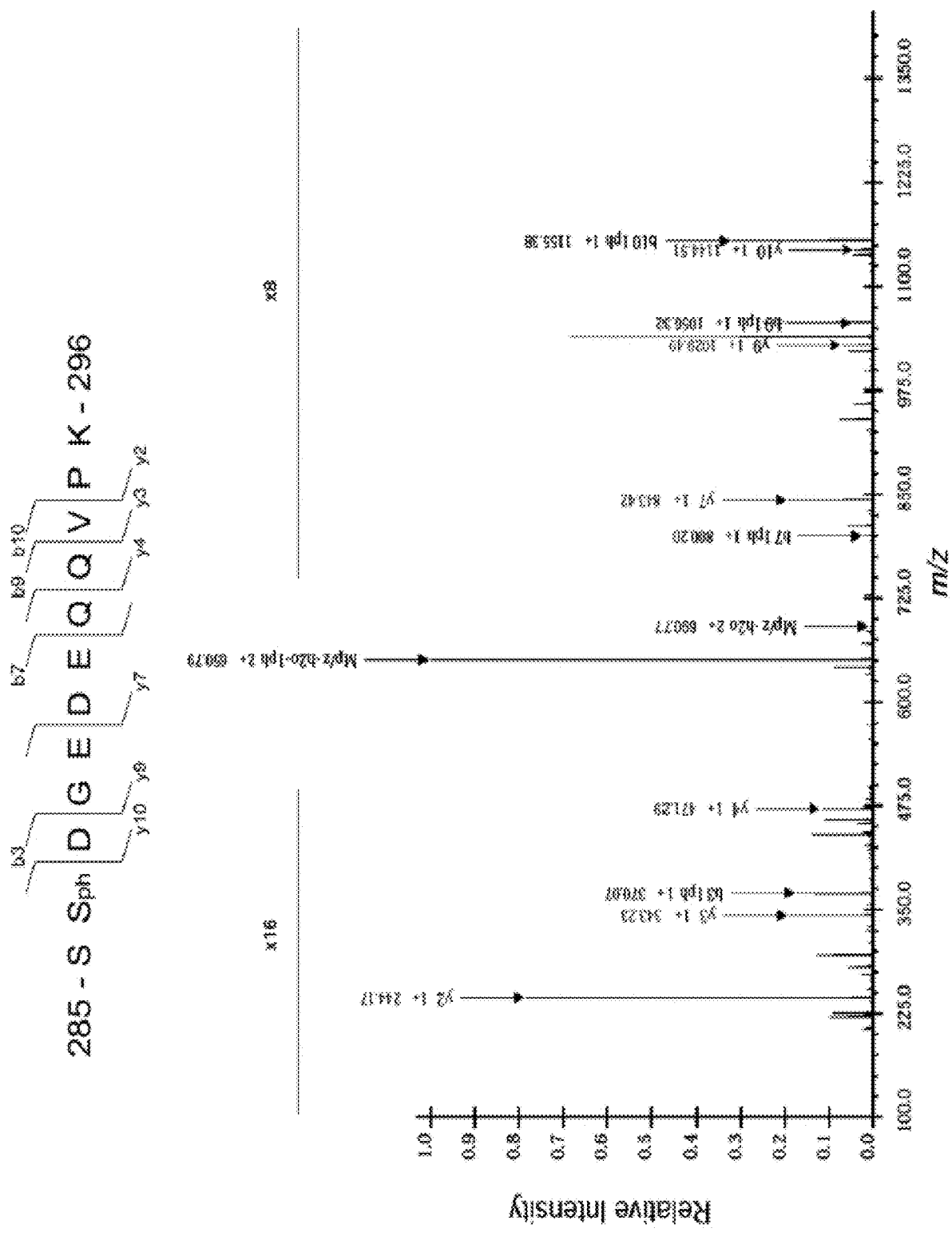
FIG. 6: Annotated CID tandem mass spectrum of the +2 ion at m/z 699.77, confirming phosphorylation of E4bp4 at S286. Tandem mass spectra acquired with an electrospray ionization LTQ/Orbitrap mass spectrometer from purified FLAG-E4bp4. FLAG-E4bp4 was expressed in HEK-293T cells and purified by immunoprecipitation with anti-FLAG M2 affinity resin and the purified protein competitively eluted using 3× FLAG peptide. Purified E4bp4 was digested with trypsin and subjected to phosphopeptide enrichment using $TiO_2$ beads to reduce background from unphosphorylated E4bp4 peptides. Magnification of certain regions of the spectra is highlighted. Spectra is schematic representation of fragmented peptide with identified ions labelled.
Figure 7:
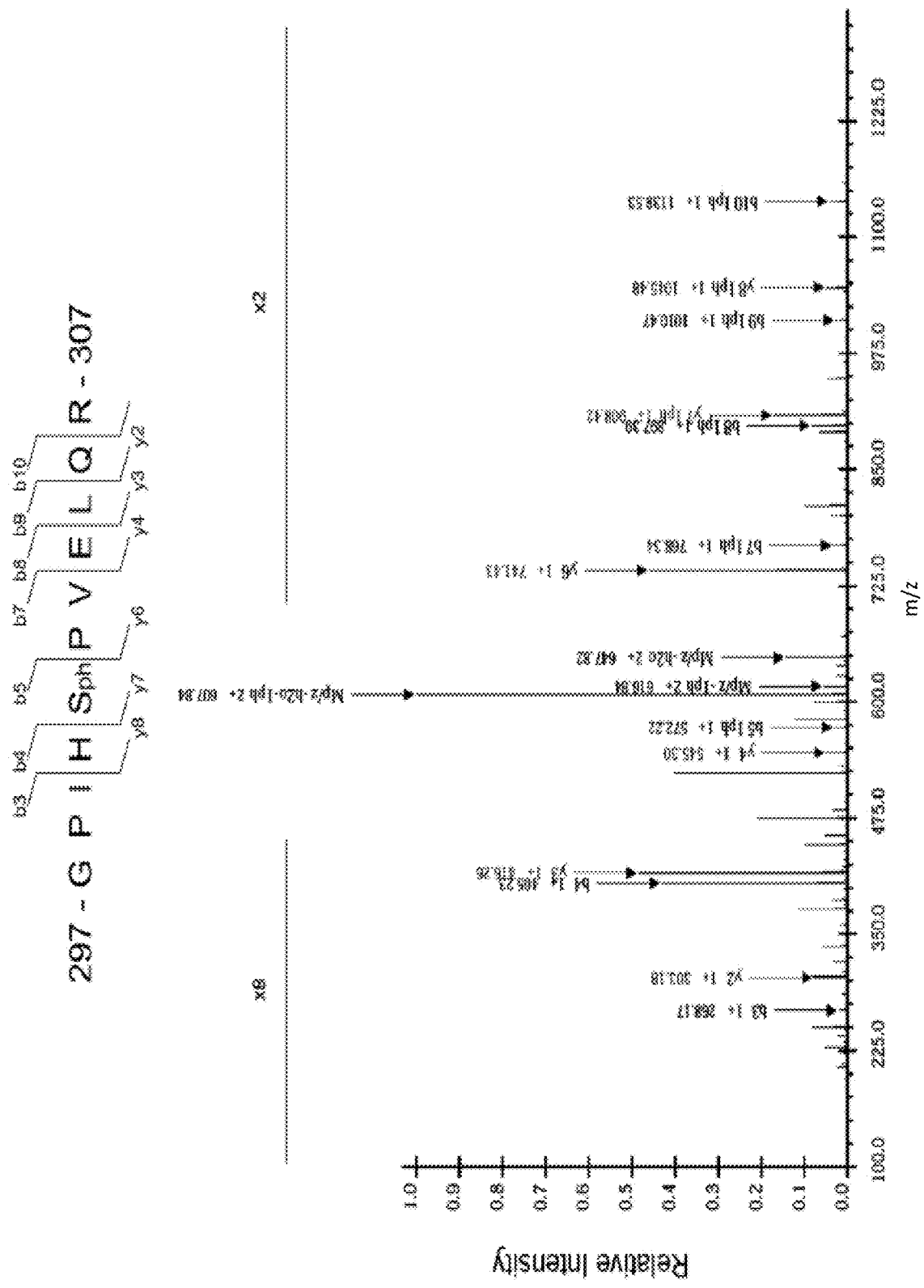
FIG. 7: Annotated CID tandem mass spectrum of the +2 ion at m/z 656.83, confirming phosphorylation of E4bp4 at S301. Details of method as above for FIG. 6.
Figure 8:
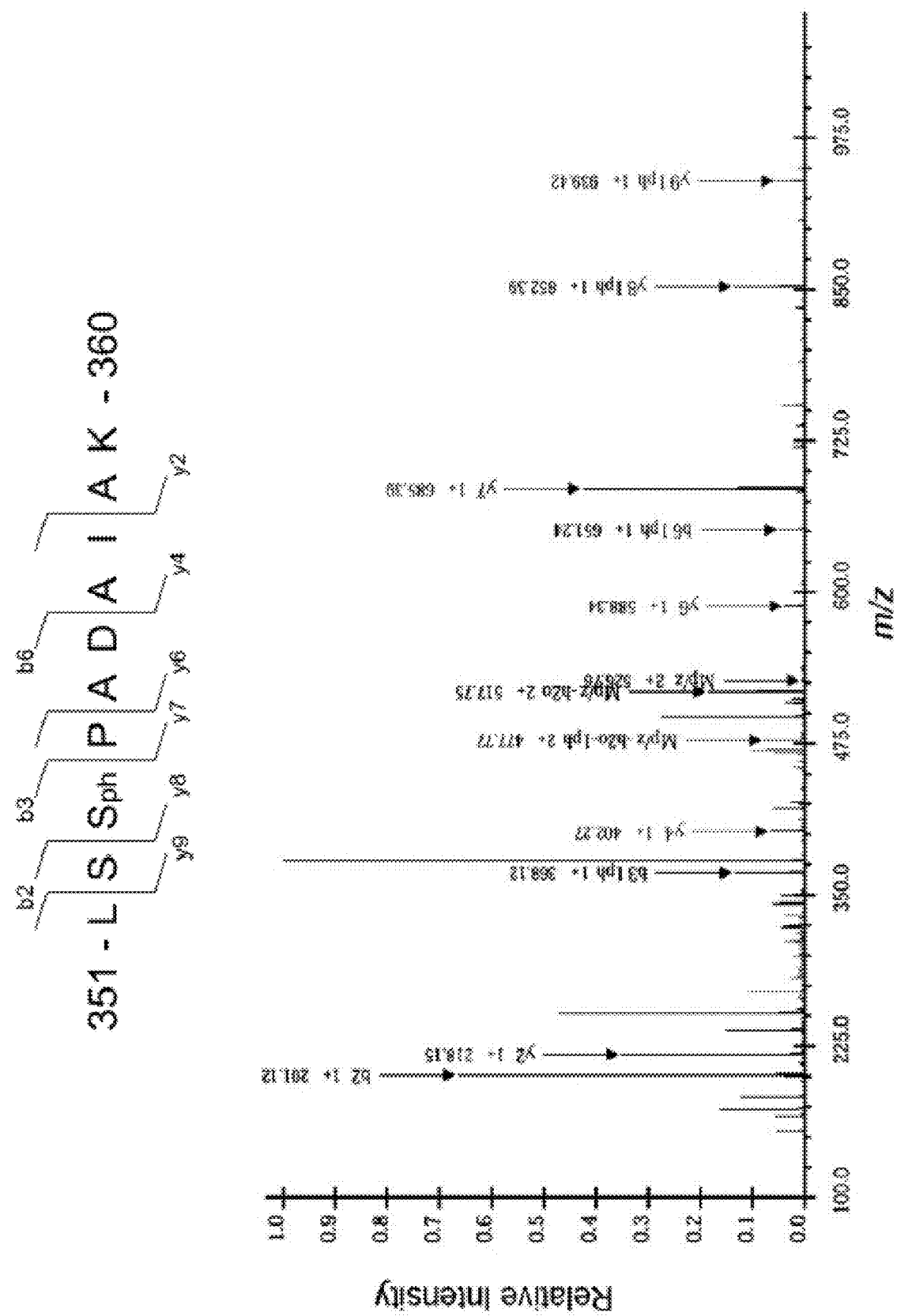
FIG. 8: Annotated CID tandem mass spectrum of the +2 ion at m/z 526.76, confirming phosphorylation of E4bp4 at S301. Details of method as above for FIG. 6.

Example 3—E4bp4 is Multiply Phosphorylated and these Modifications Influence NK Cell Development To determine which residues of E4bp4 are phosphorylated FLAG-E4bp4 expressed in 293T cells was purified and digested the protein using trypsin for LC-MS/MS analysis. The tandem MS conclusively revealed that E4bp4 has three phosphorylation sites at serines 286, 301 and 353 (FIGS. 5A and 6-8). Each of these serine residues was mutated to alanine to abolish any phosphorylation but maintain protein conformation. As described for SUMOylation, the aim was to determine if phosphorylation regulates the function of E4bp4. Each phosphorylation mutant was expressed by retroviral expression vector in E4bp4$^{-/-}$ Lin⁻ BM cells and these were cultured in conditions promoting NK cell development. The ability of the phosphorylation mutants to rescue NK cell development was compared to the WT-form of E4bp4 and several of the mutants were found to promote significantly higher levels of NK cell production (FIG. 5B, C). In particular, the S286A mutant produced double the number of NK cells as WT-form E4bp4 (FIG. 5B). The phosphorylation mutants were also transduced into E4bp4$^{+/+}$ Lin⁻ BM cells and NK cell production was greatly enhanced in the cells transduced with the phosphorylation mutants compared to those transduced with the WT-form of E4bp4, particularly with the S286A and S286-353A mutants (FIG. 5E, E). The phenotype observed when phosphorylation sites were mutated replicated that described above for SUMOylation. Therefore, both post-translational modifications (PTMs) negatively regulate the function of E4bp4 in NK cells and manipulating the PTMs of E4bp4 provides a simple mechanism to control NK cell production.

Example 4—SUMOylation and Phosphorylation do not Affect the Stability of E4bp4

Figure 9:
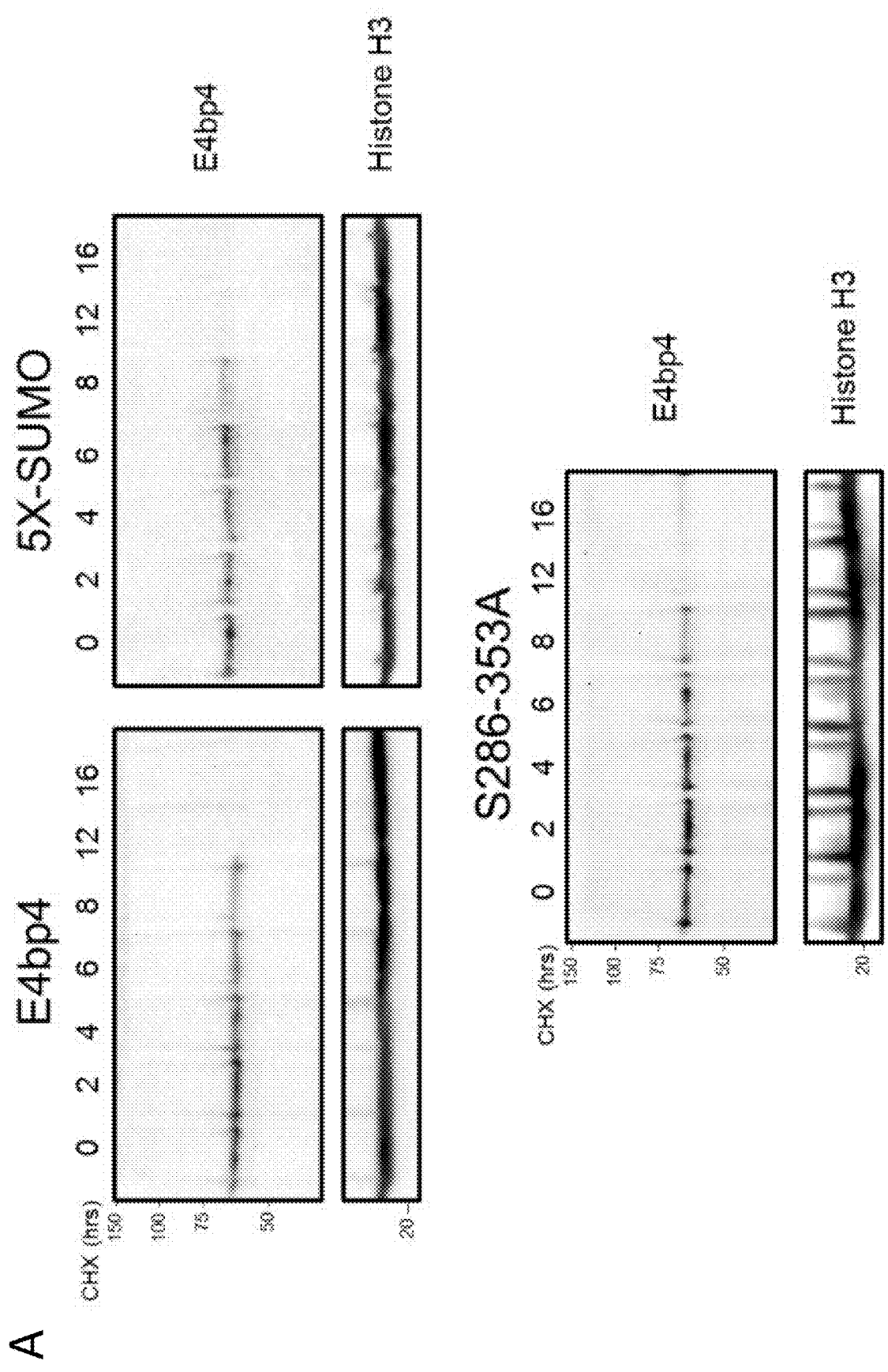
FIG. 9: (A) 3T3 cells stably expressing E4bp4, 5×-SUMO and S286-353A were treated with cycloheximide (CHX, 50 µg ml$^{-1}$) for the times indicated. Western blotting was used to compare nuclear extracts. (B) Quantification of relative E4bp4 expression from Western blot signals using densitometry. Level of E4bp4 is represented in arbitrary units after signals were normalised relative to those of Histone H3. (C, D) Transcriptional reporter assay using a Firefly Luciferase gene downstream of E4bp4 consensus binding sites. Relative luciferase activity was measured after 48 h from 3T3 cells transfected with MSCV-E4bp4-IRES-hCD2 and Firefly luciferase construct. Data are representative of ten independent experiments for each mutant. (E) MNK-1 cells were transduced with either vector control, E4bp4, 5×-SUMO or S286-353A. Expression of Eomes, Gata3, Tbet and Notch1 were determined by QPCR. Data are representative of three independent experiments for each mutant. Error bars show SEM. *, P<0.05.
Figure 9:
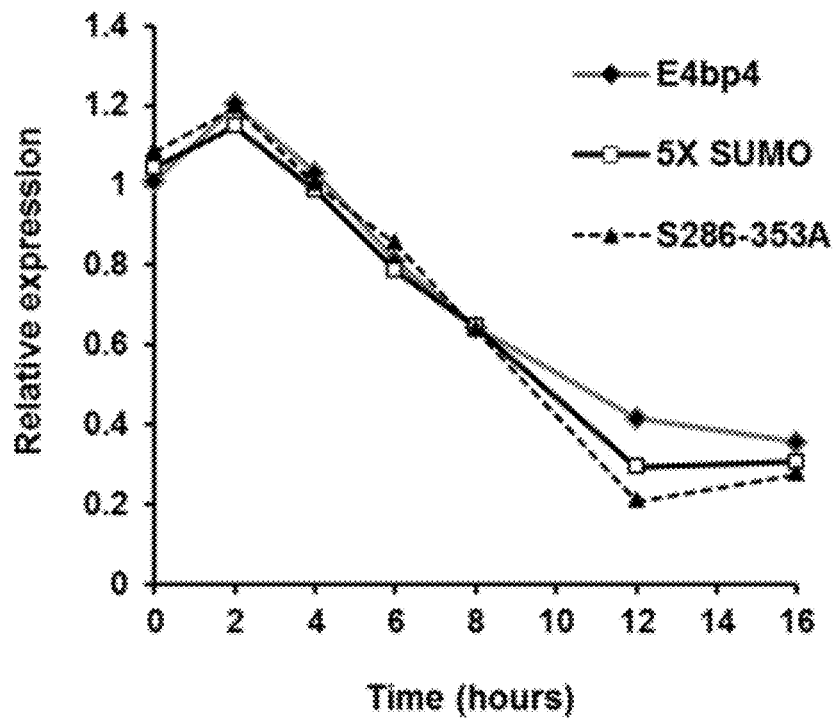
Figure 9:
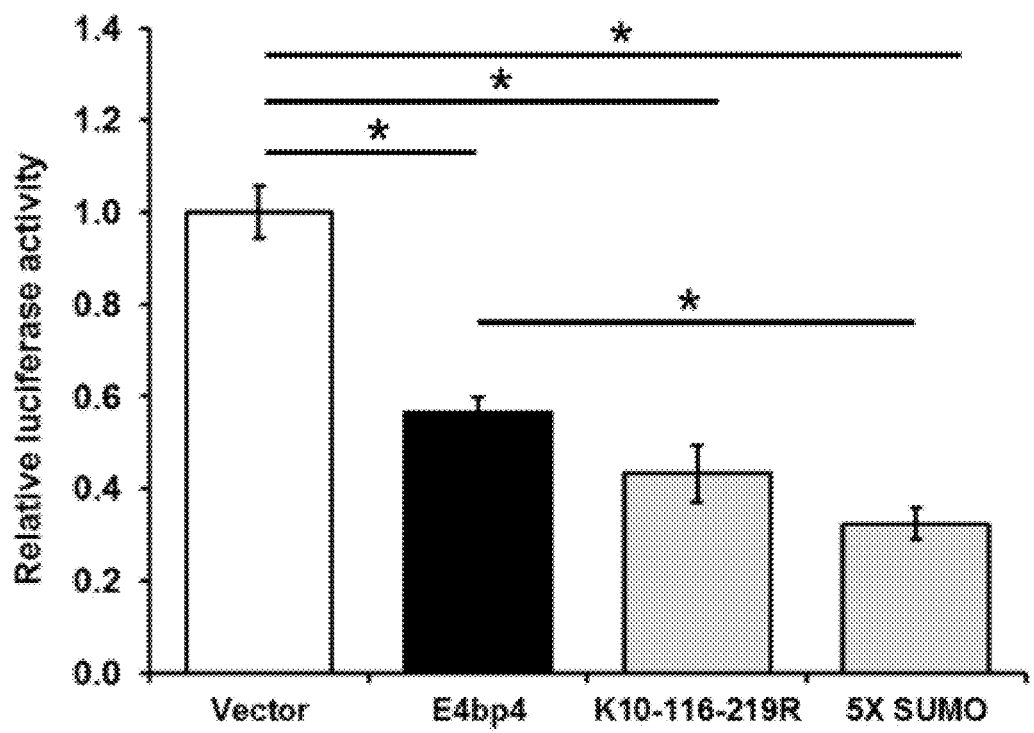
Figure 9:
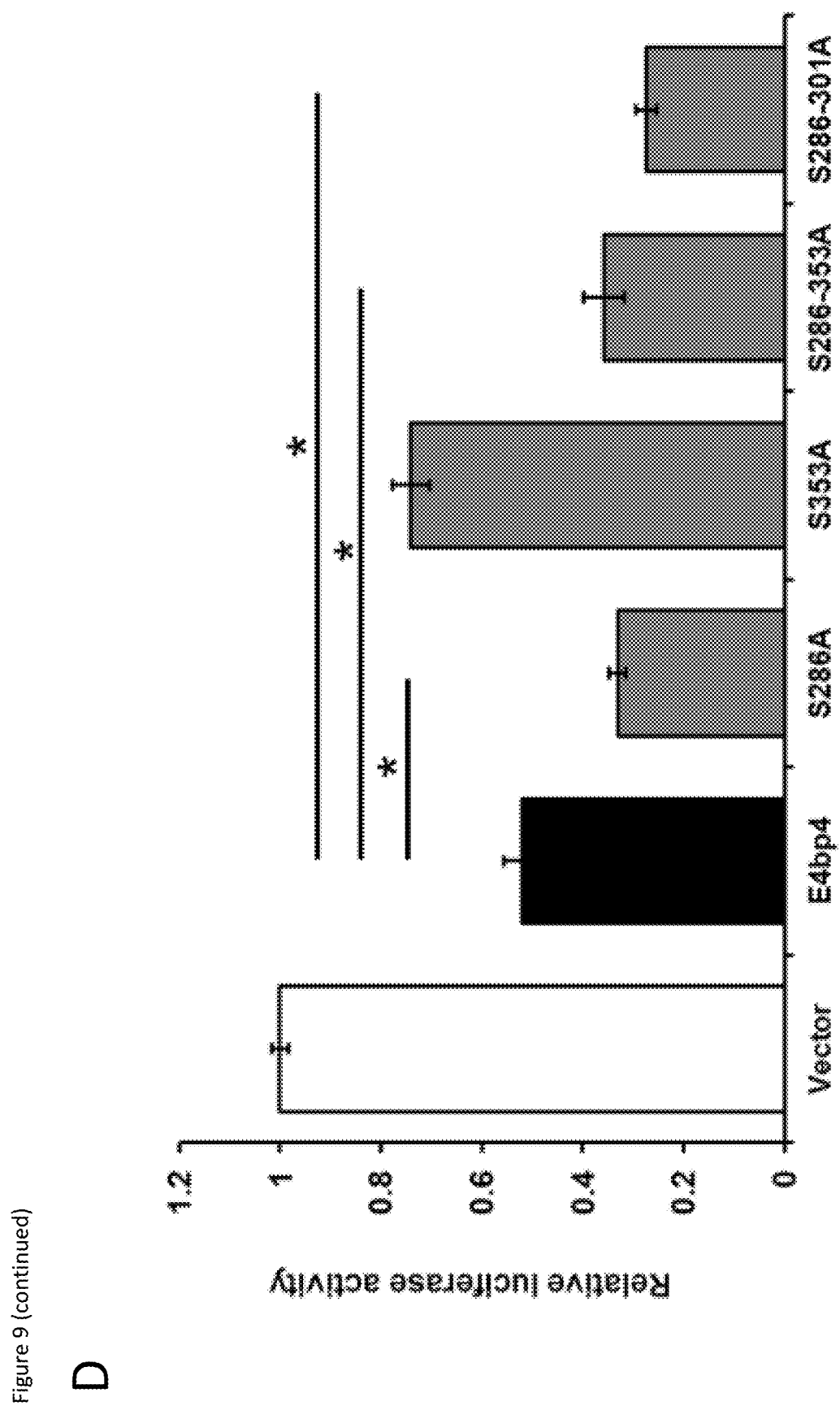
Figure 9:
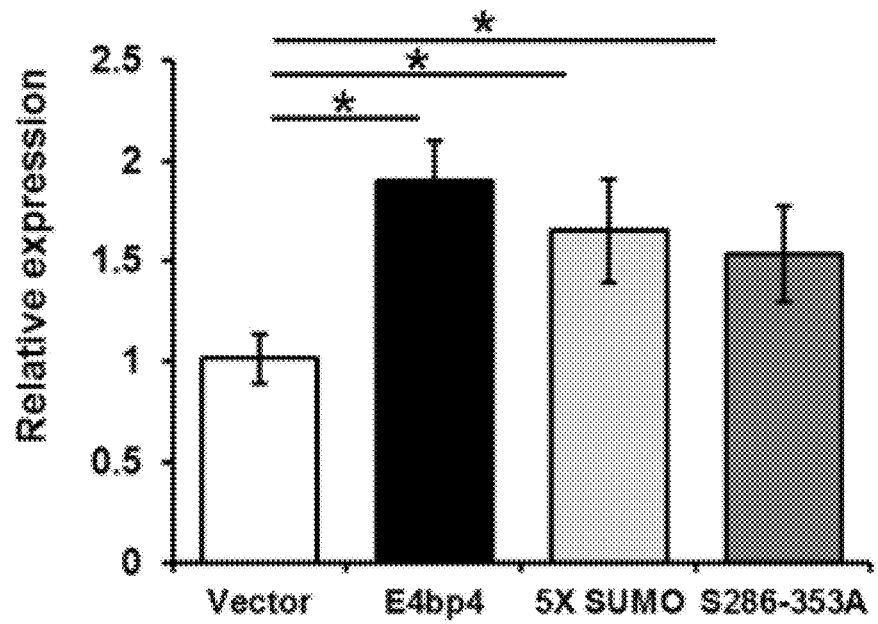
Figure 9:
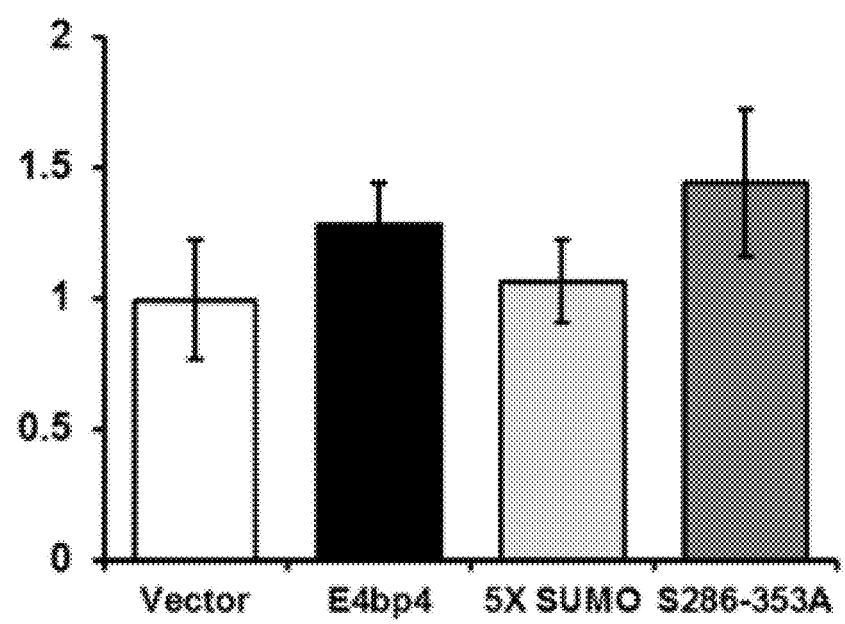
Figure 9:
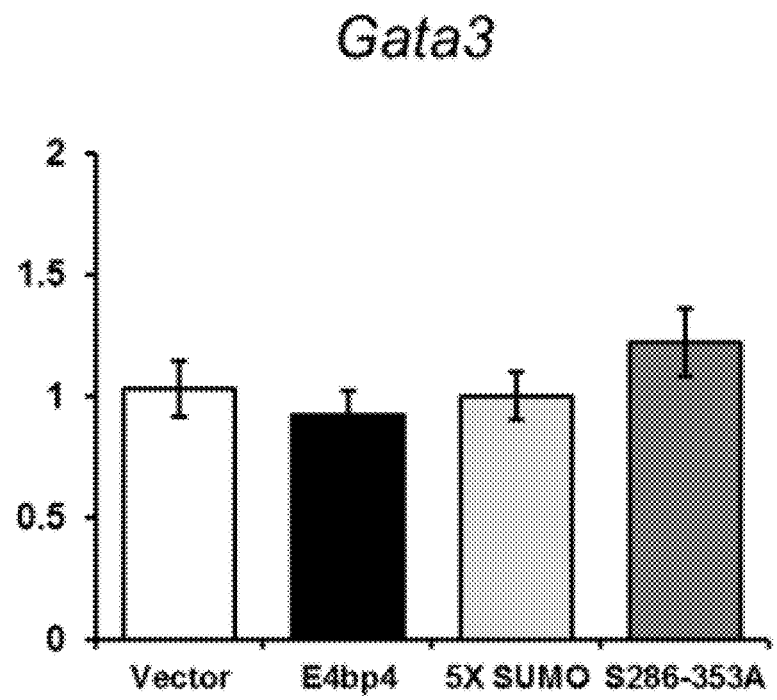
Figure 9:
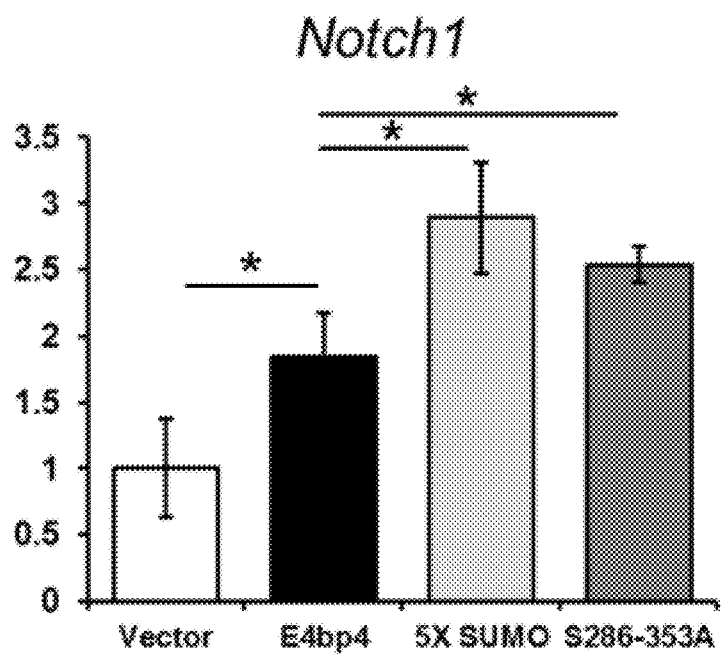

SUMOylation and phosphorylation can both affect the stability of a transcription factor and influence its proteasomal degradation. As the absence of both of these PTMs enhanced the function of E4bp4 during NK cell development, it was investigated whether the mutant versions of E4bp4, lacking PTM sites, had altered stability. Using a cycloheximide time course assay on cell lines stably expressing the 5x-SUMO, S286-353A mutants or the WT-form of E4bp4, the stability of each form of E4bp4 was compared. Both mutants had very similar half-lives to WT E4bp4 with protein levels reduced by almost half after 8 hours of cycloheximide treatment (FIG. 9A, B).

Example 5—the Transcriptional Activity of E4bp4 can be Regulated by SUMOylation and Phosphorylation E4bp4 was first identified as a transcriptional repressor and has been shown to repress the expression of numerous target genes in vivo e.g. 11-13 in TH2 cells. However, E4bp4 has likewise been found to transactivate the expression of various target genes, including Id2 and Eomes in NK cells. It was postulated that SUMOylation and phosphorylation might influence the ability of E4bp4 to control target gene expression. To analyse the effect on gene transcription, a luciferase reporter gene assay was used as readout. Cells were co-transfected with an E4bp4 expression vector and a plasmid with three E4bp4 DNA binding sequences upstream of the pGL3 promoter luciferase reporter. E4bp4 was found to act as a transcriptional repressor in this context (FIG. 9C). The WT-form of E4bp4 consistently led to a 50% decrease in luciferase expression, as previously reported 24, but the E4bp4 5x-SUMO mutant promoted even greater transcriptional repression than the WT-form of E4bp4 (FIG. 9C). A similar observation was observed for the E4bp4 phosphorylation mutants, particularly those containing a S286A mutant residue (FIG. 9D). These data indicate the E4bp4 PTM mutants influence transcription via E4bp4-binding consensus sequences in an episomal context. Based on these findings, it was decided to test, in a NK cell context, if the E4bp4 PTM mutants had any effect on the expression of endogenous genes known to strongly influence lymphoid cell development.

The mouse NK cell line MNK was transduced with the WT-form of E4bp4, the 5x-SUMO and S286-353A mutants. E4bp4 promoted Eomes expression in these cells and a similar level of expression was seen in the presence of both E4bp4 mutants (FIG. 19E). E4bp4 did not affect the transcription of Gata3 or Tbet, however, it was found to promote the expression of Notch1 and, strikingly, an even greater increase in expression was seen with the 5x-SUMO and S286-353A E4bp4 mutants (FIG. 9E). This provided evidence that SUMOylation and phosphorylation negatively regulate the transcriptional activation effect of E4bp4. These data show that removing these PTMs makes the E4bp4 protein both a more potent transcriptional activator or more potent transcriptional repressor depending on context. This observation provides an insight into the mechanism by which the mutant forms of E4bp4 enhance NK cell production to a greater extent than WT-form E4bp4 and suggests a previously unknown mechanism of NK cell development, namely, that E4bp4 might act on the Notch signalling pathway.

Example 6—E4bp4 can Act Through Notch to Promote NK Cell Development

Figure 10:
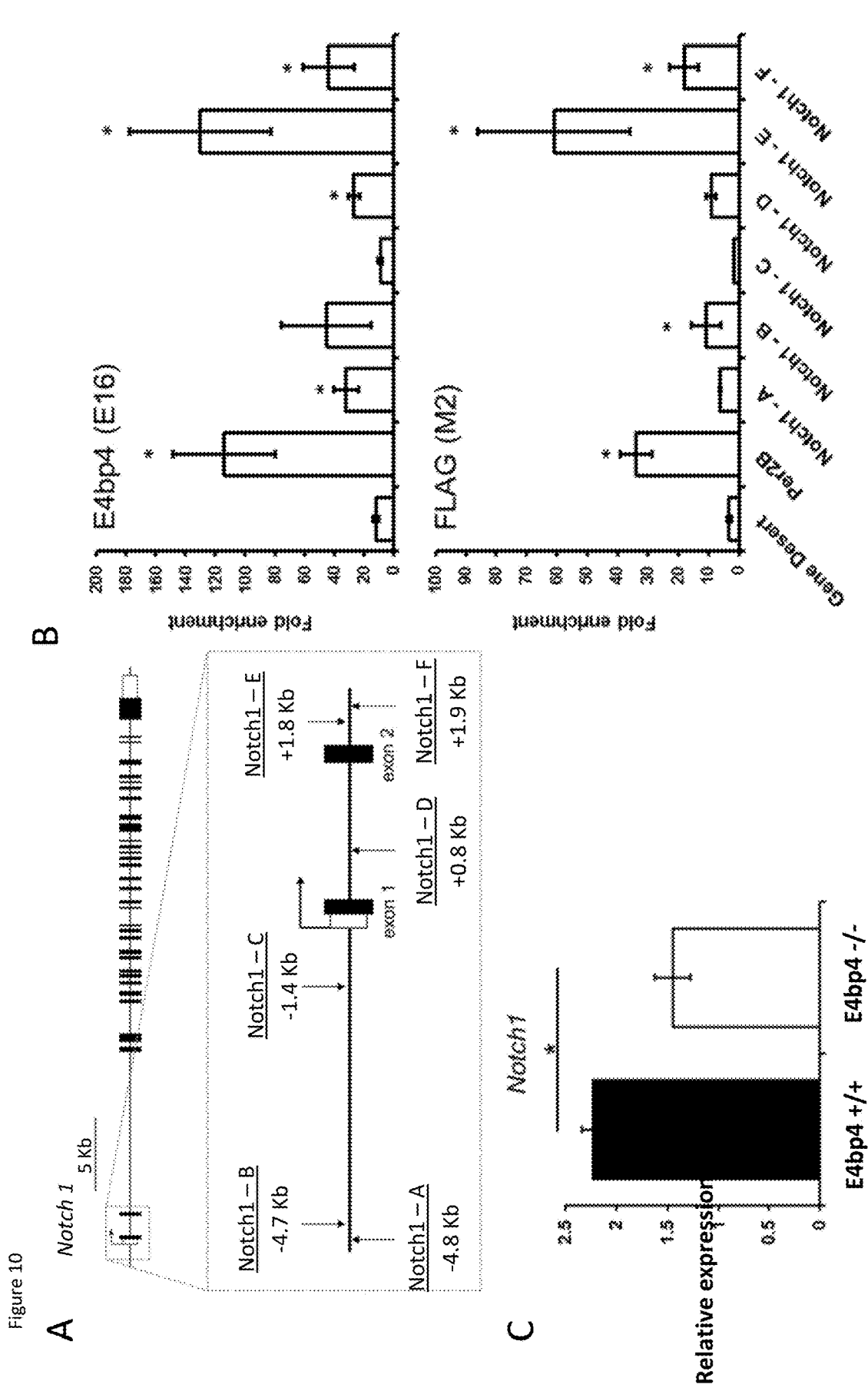
FIG. 10: Notch1 is a transcriptional target of E4bp4 in NK cells. (A) Notch1 locus showing location of predicted E4bp4 binding sites identified through the presence of the E4bp4 minimal consensus binding sequence TTA(T/C)(G/A)TAA (C/T). Filled boxes=exons; clear boxes=UTR regions (B) ChIP analysis of E4bp4 binding at the Notch1 loci in chromatin from MNK-1 cells stably transduced with FLAG-E4bp4. E16 is a polyclonal antibody to E4bp4 and M2 is a monoclonal antibody to FLAG. Per2B was used as a positive control and gene desert as a negative control. Data is representative of three biological replicates. Error bars show SEM. *, P<0.05. (C) QPCR analysis of Notch1 expression in Lin$^-$ BM cells. Data is representative of six biological replicates. Error bars show SEM. *, P<0.05.

The effect of E4bp4 on the expression of Notch1, and whether this might potentially influence NK cell production, was investigated. Transient Notch signalling has previously been shown to induce the development of NK cells from Pax5$^{-/-}$ pro-B cells and murine HSCs. First, it was examined whether Notch1 is a direct transcriptional target of E4bp4. Using chromatin immunoprecipitation (ChIP) it was determined whether E4bp4 could directly bind to the regulatory region of the Notch1 gene in vivo. MNK-1 cells were transduced with FLAG-tagged E4bp4 and protein-chromatin complexes were precipitated by either IgG, anti-FLAG or anti-E4bp4 antibodies. The regulatory regions around the transcriptional start site (TSS) of Notch1 were searched and six putative E4bp4 binding sites identified (FIG. 10A). E4bp4 binding was found to be highly enriched at predicted site E, to an even greater degree than the previously best characterised E4bp4 binding regulatory region found in the Per2B gene. In addition, sites A and B upstream of the TSS and sites D and F downstream of the TSS were also enriched in the E4bp4 immunoprecipitated samples (FIG. 10B). This indicated that E4bp4 binds to regulatory regions of Notch1 that could enhance its transcriptional activation. To further test the hypothesis that E4bp4 can regulate the expression of Notch1, it was postulated that a loss of E4bp4 should influence Notch1 expression in HPCs in vivo. The expression of Notch1 in E4bp4$^{+/+}$ and E4bp4$^{-/-}$ Lin$^-$ bone marrow (BM) cells was compared and found that, in the absence of E4bp4, Notch1 expression was indeed significantly reduced as shown previously for another E4bp4 target gene, Id23 (FIG. 10C).

Figure 11:
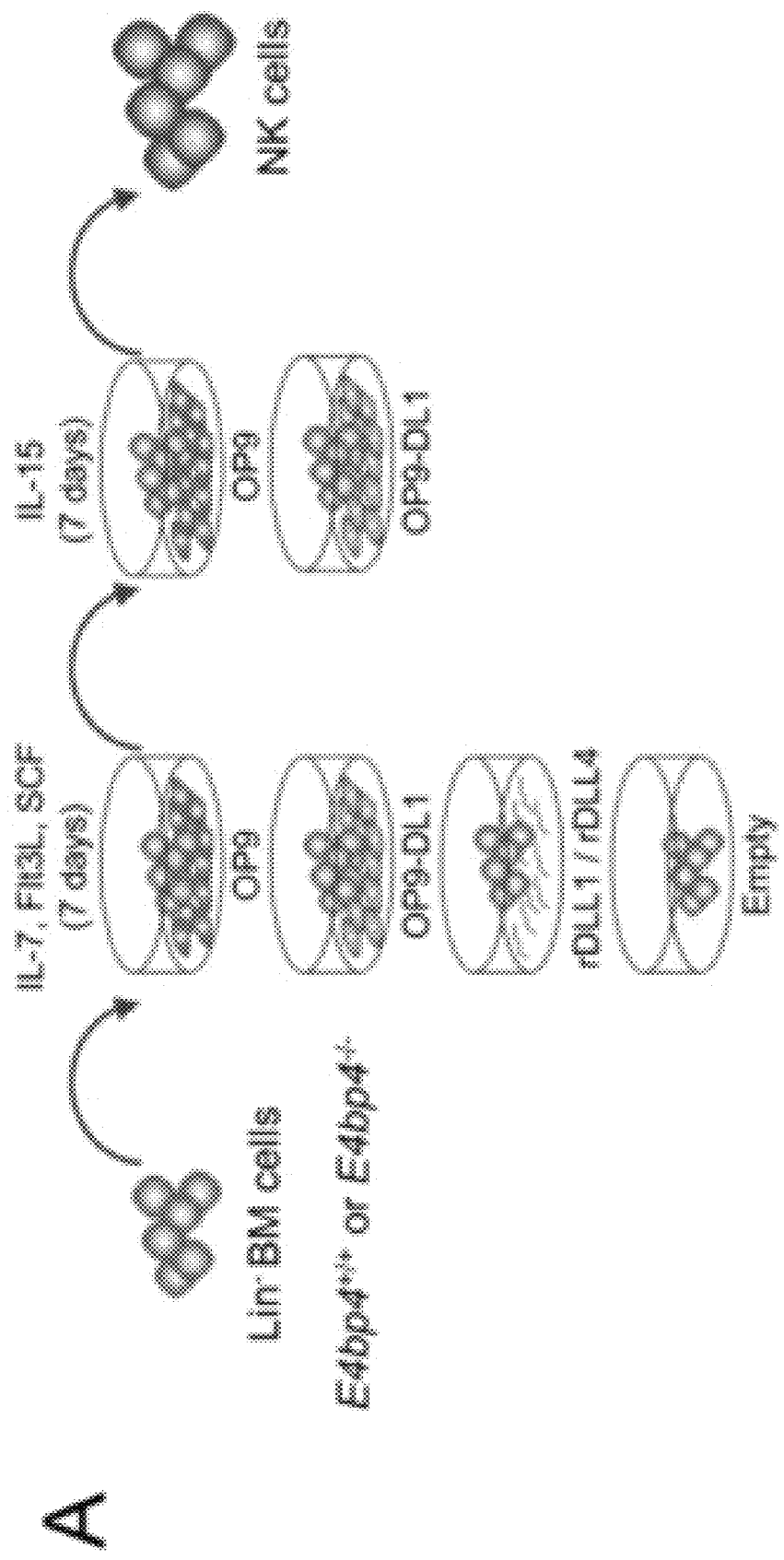
FIG. 11: Notch signalling at an early stage can induce NK cell development in the absence of E4bp4. (A) Schematic representation of culture system used to induce Notch signalling and promote NK cell development from Lin$^-$ BM cells. (B) Flow cytometry analysis of NK cell production following cultivation on indicated combination of OP9 or OP9-DL1 stromal cells or (C) on empty plates or plates coated with recombinant rDLL1/rDLL4. Lin$^-$ BM cells were first cultured for 7 days in IL-7, Flt3L, SCF before transferring to new plates for culture in IL-15. Data is representative of four (B) or two (C) biological replicates. (D) Schematic representation of two-stage culture of NK cell development from Lin$^-$ BM cells following from Cre-mediated deletion of Rbpj gene following lentiviral transduction. (E) Flow cytometry analysis of NK cell production derived from Lin$^-$ BM isolated from Rbpj floxed mice and transduced with either empty or Cre-expressing lentiviral vector. Cells were cultivated either on OP9 stromal cells alone or on rDLL4-coated plates before transfer on to OP9 as indicated. Data shown is for cells gated on hCD2 expression.
Figure 11:
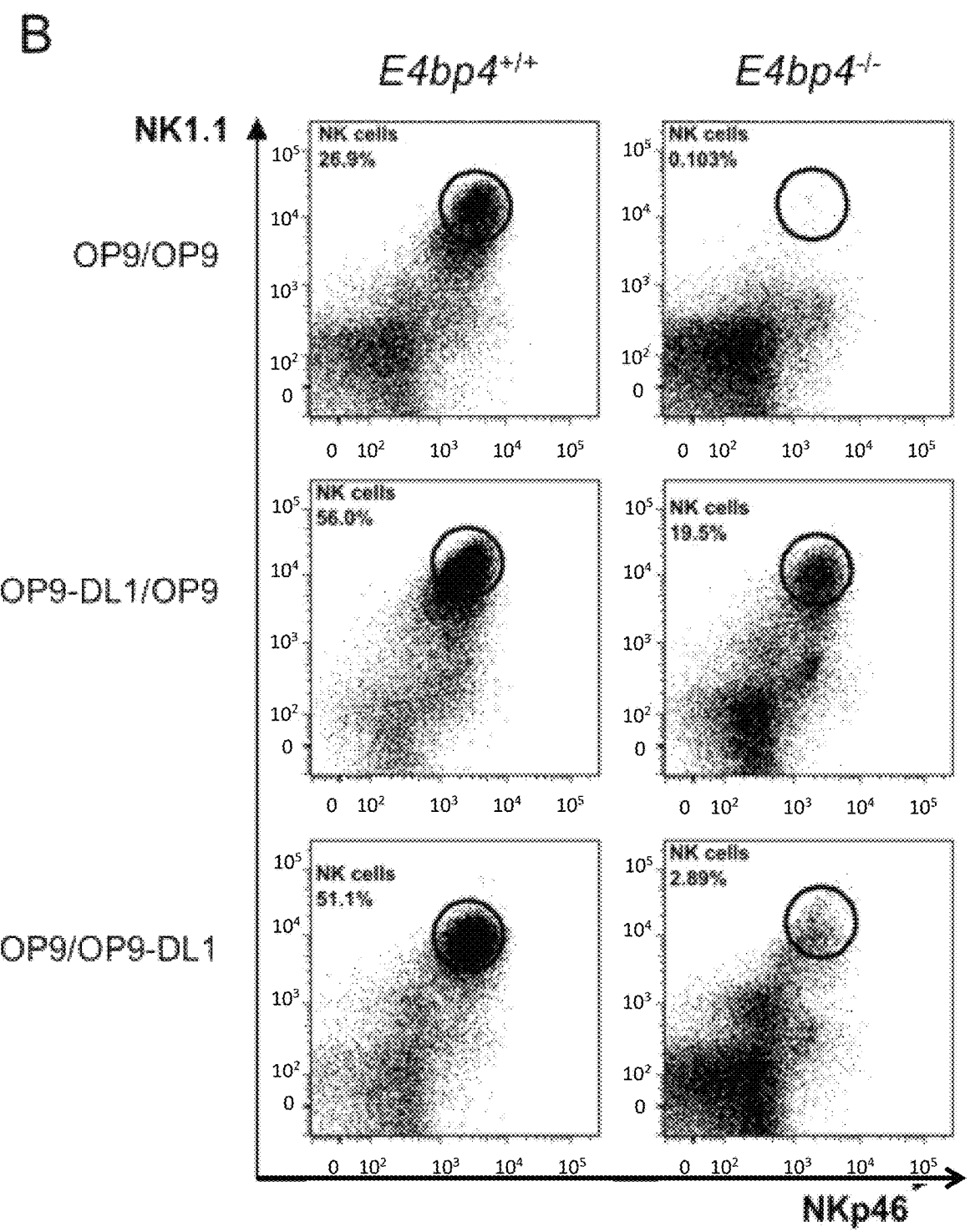
Figure 11:
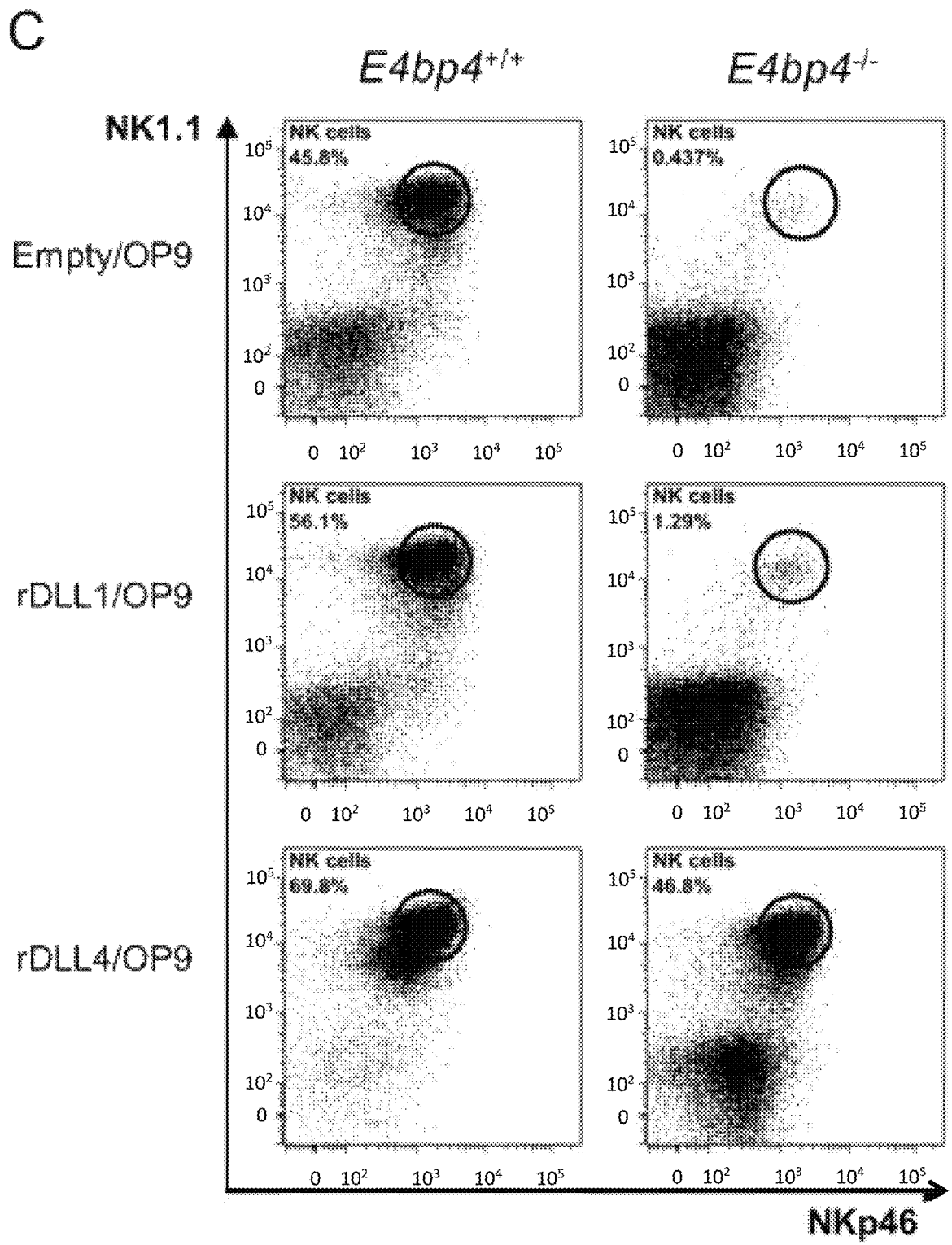
Figure 11:
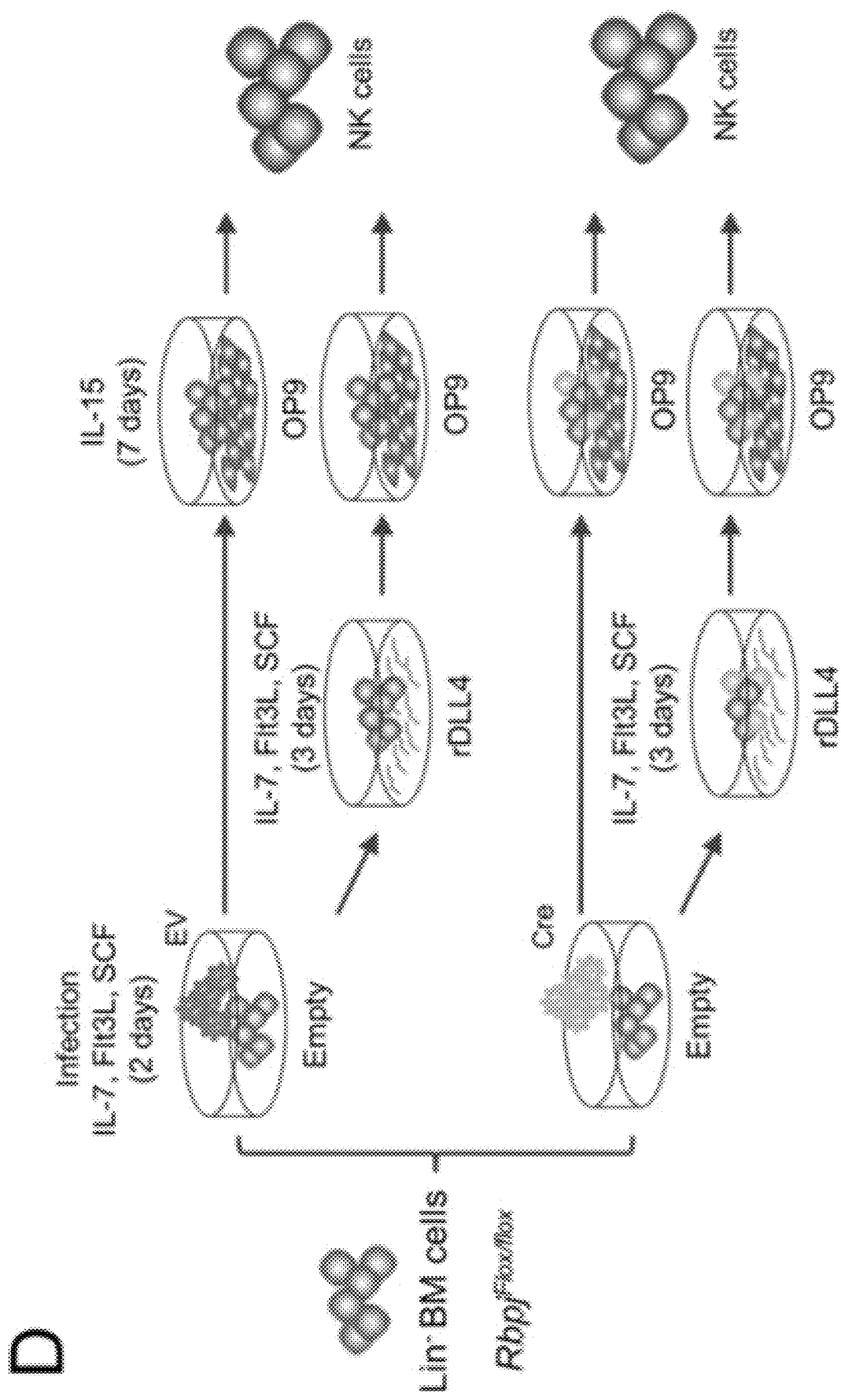
Figure 11:
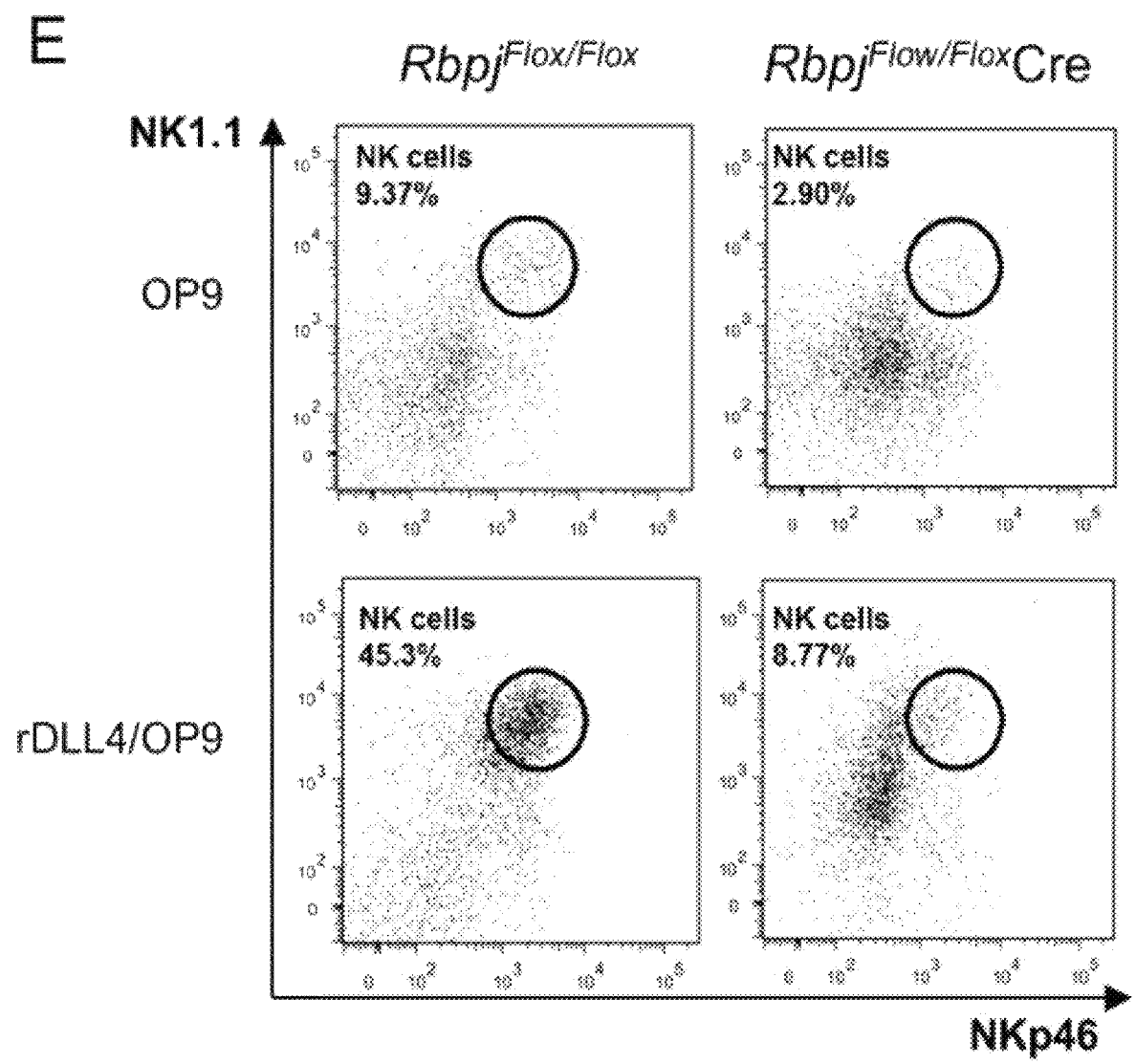

As E4bp4 appeared to regulate Notch1 expression, it was speculated that enhanced Notch signalling, at an early stage, could potentially affect the development of NK cells from E4bp4$^{-/-}$ HPCs. To study NK cell development from HPCs in the presence or absence of Notch signalling, Lin$^-$ BM cells were cultured on either OP9 stromal cells or OP9-DL1 cells (that express the Notch ligand delta-like 1) (FIG. 10C). Subsequently, cells were transferred onto fresh OP9 and cultured in the presence of IL-15 (FIG. 11A). When E4bp4$^{-/-}$ cells were grown on control OP9, no NK cell development was observed, but when the E4bp4$^{-/-}$ cells were grown on OP9-DL1 for the first part of the culture, remarkably, NK cell development was rescued (FIG. 11B). The same result was not observed when the cells were grown on OP9-DL1 for the second part of the culture (FIG. 11B). To eliminate the influence of stromal cells, tissue culture plates were coated with either recombinant delta-like ligand 1 (rDLL1) or rDLL4 protein. These plates were used for the first 7-day period of the culture (FIG. 11B). Some Delta-like ligands have previously been shown to efficiently induce Notch signalling when immobilised onto plastic surfaces. When cultured on empty plates, the E4bp4$^{-/-}$ Lin$^-$ BM cells did not develop into NK cells, but when grown on rDLL4-coated plates the production of NK cells could be dramatically rescued entirely in the absence of the critical transcription factor for NK cell development (FIG. 11C). Only a very partial rescue was observed when the cells were cultured on rDLL1-coated plates (FIG. 11C). Additionally, when E4bp4$^{+/+}$ HPCs were cultured on rDLL4-coated plates, the level of NK cell production was increased compared to cells grown on uncoated plates (FIG. 11C).

It was then investigated whether abrogation of Notch signalling would have any direct influence on NK cell development by using a method engendering Cre-mediated deletion of the Rbpj$^{flox/flox}$ gene. Recombination signal-binding protein J$_K$ (RBP-J) is a transcriptional cofactor critical for the expression of target genes activated by the Notch signalling pathway. HPCs isolated from Rbpj$^{flox/flox}$ mice were transduced by a lentivirus co-expressing Cre recombinase and truncated human CD2. The human CD2 expression served to mark all transduced cells. Following transduction, HPCs were cultured on OP9 cells with IL-15 or first cultured on rDLL4-coated plates for 3 days before transfer to OP9 plus IL-15 (FIG. 11D). Much reduced numbers of mature NK cells developed from those HPCs subject to Cre-deletion (FIG. 11E). This differential effect was greatly accentuated by pre-incubation with rDLL4 that selectively enhances NK cell development from HPCs (FIG. 11E). These data suggest that Notch signalling can play a role in the early stages of NK cell development and this action is as an integral part of the E4bp4-mediated transcriptional network that controls NK cell production.

Example 7—the Combination of SR8278 and DLL4 Treatment Results in a Significant Increase in NK Cell Production Ex Vivo The effect of combining REV-ERB inhibition and Notch ligand exposure on NK cell production was investigated.

HPCs were cultured in four sets of conditions in addition to control (non-treated) conditions: (i) treated with SR8278 on day 2 of culture (no recombinant DLL4, rDLL4); (ii) cultured on rDLL4 (no SR8278); (iii) cultured on rDLL4 and treated with SR8278 on day 0 of culture; or (iv) treated with SR8278 on day 0 of culture, cultured on rDLL4 from day 2. Aside from the different treatments, the culture conditions were otherwise identical to those previously described for NK cell production from HPCs.

Figure 12:
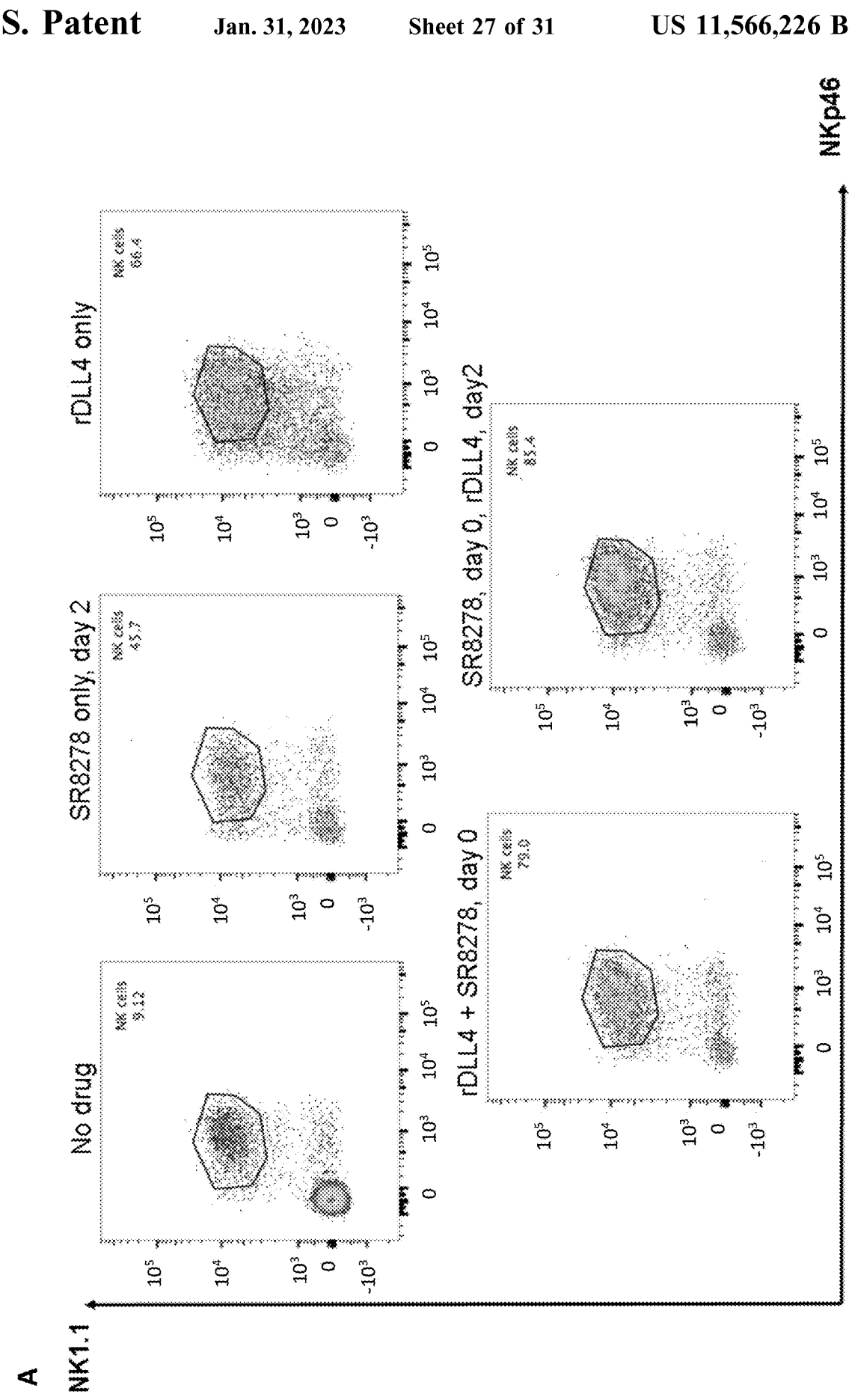
FIG. 12: Synergy between REV-ERB antagonism and the Notch ligand, rDLL4. (A) Flow cytometry analysis of NK cell production following cultivation with the indicated combinations of SR8278 and rDLL4. (B) The graph shows the percentage of mature (NK1.1$^+$NKp46$^+$) NK cells against the different conditions.
Figure 12:
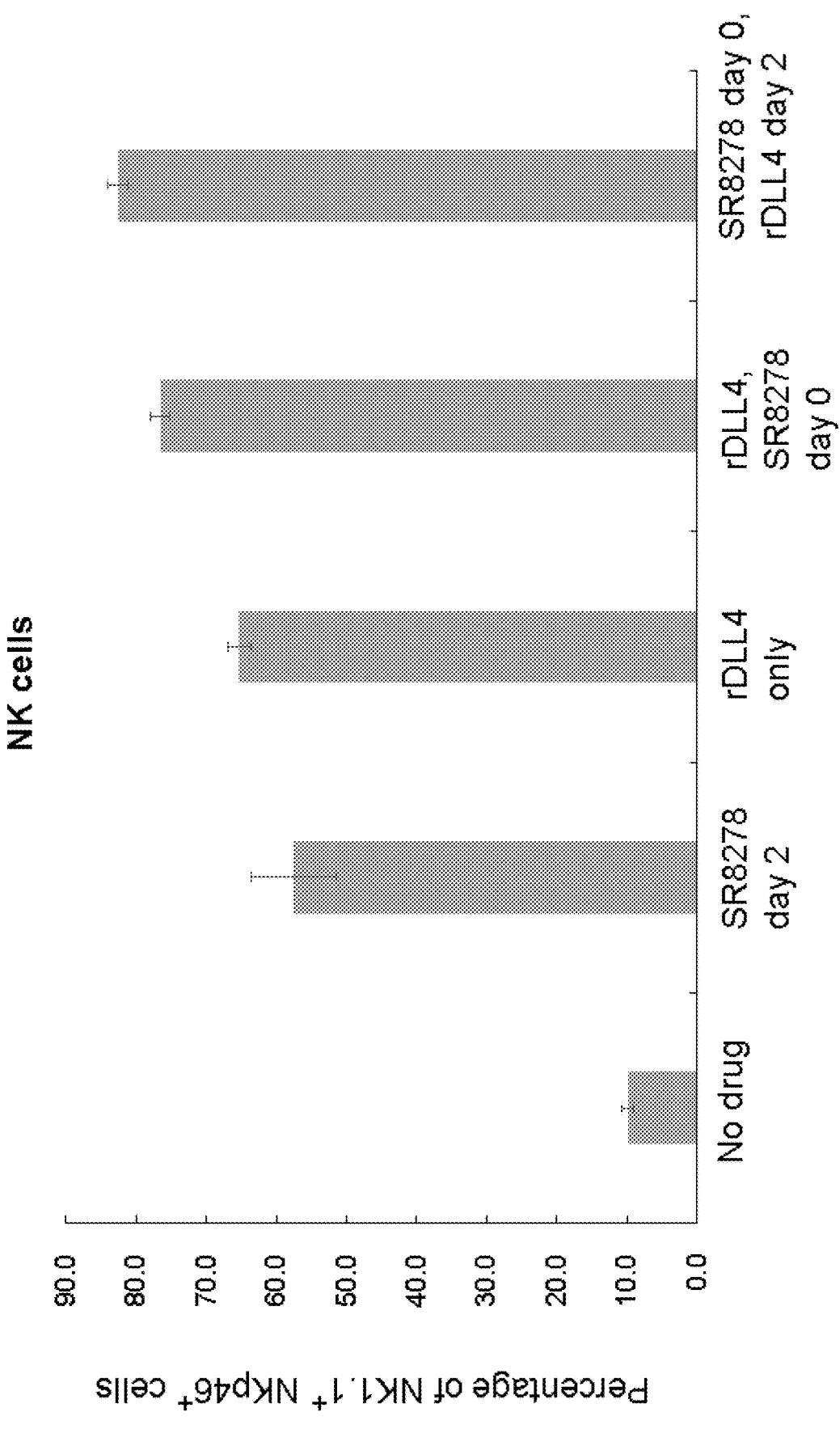

As shown in FIGS. 12A and B, the percentage of NK cells in the absence of both SR8278 and rDLL4 was low (less than 10%). The percentages (in FIG. 12B) are the average of separate triplicate experiments. The addition of SR8278 on day 2 of culture produced a significant increase in the % of NK cells produced (57.5%), as did culturing the HPCs on rDLL4 in the absence of SR8278 (65.3%). Culturing the HPCs on rDLL4 with SR8278 treatment on day 0 of culture elicited a further increase in NK cell production (77%). However, first incubating the HPCs with SR8278 on day 0 and then switching to culture on rDLL4 on day 2 had an even greater effect, with an average of 82.5% of the cells produced being NK cells (and in some repeats, over 85% of cells produced were NK cells).

Figure 13:
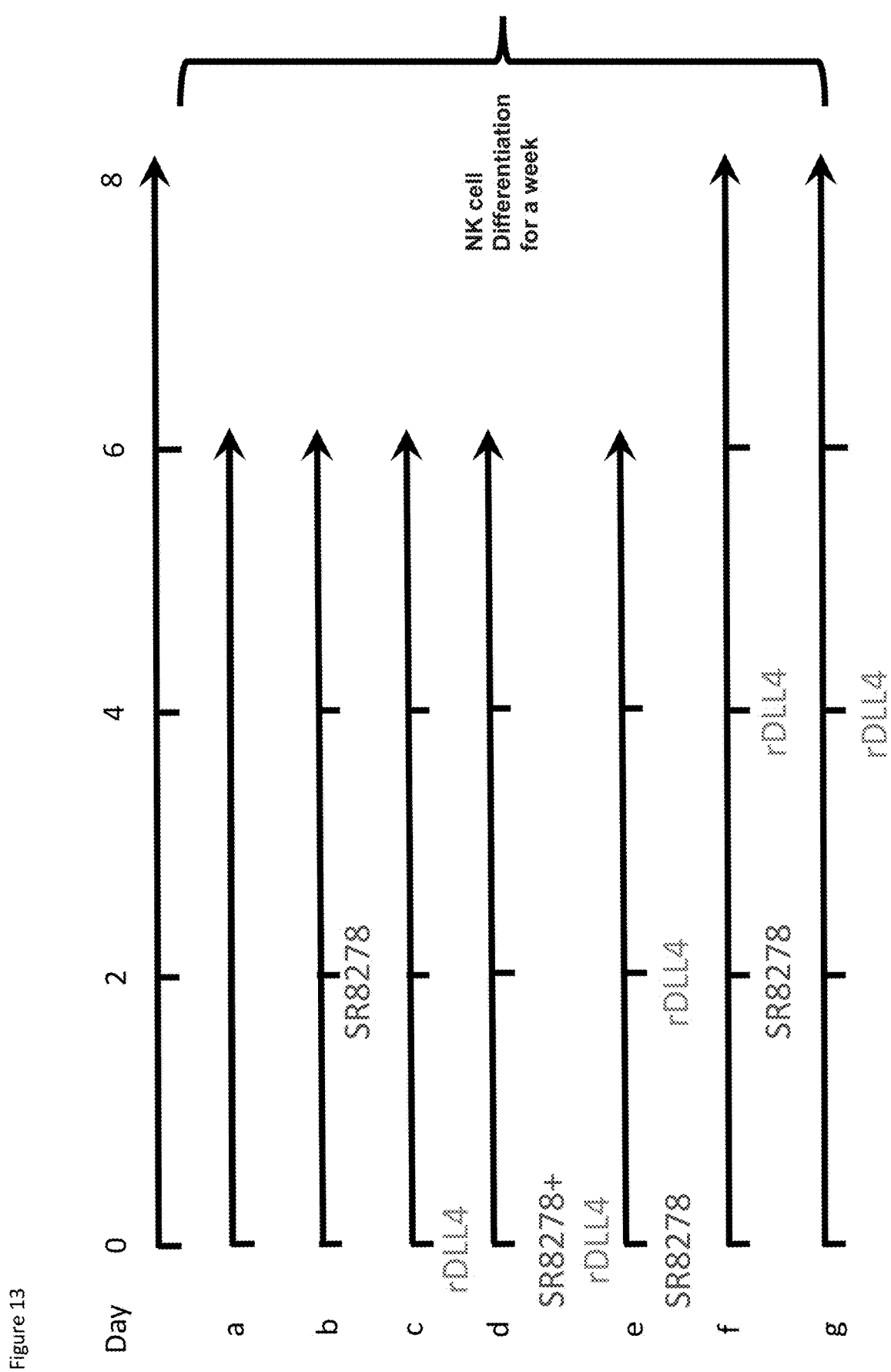
FIG. 13: Experimental design to test if there is a synergistic effect of the REV-ERB antagonist SR8278 with the recombinant Notch ligand rDLL4 on NK cell production.
Figure 14:
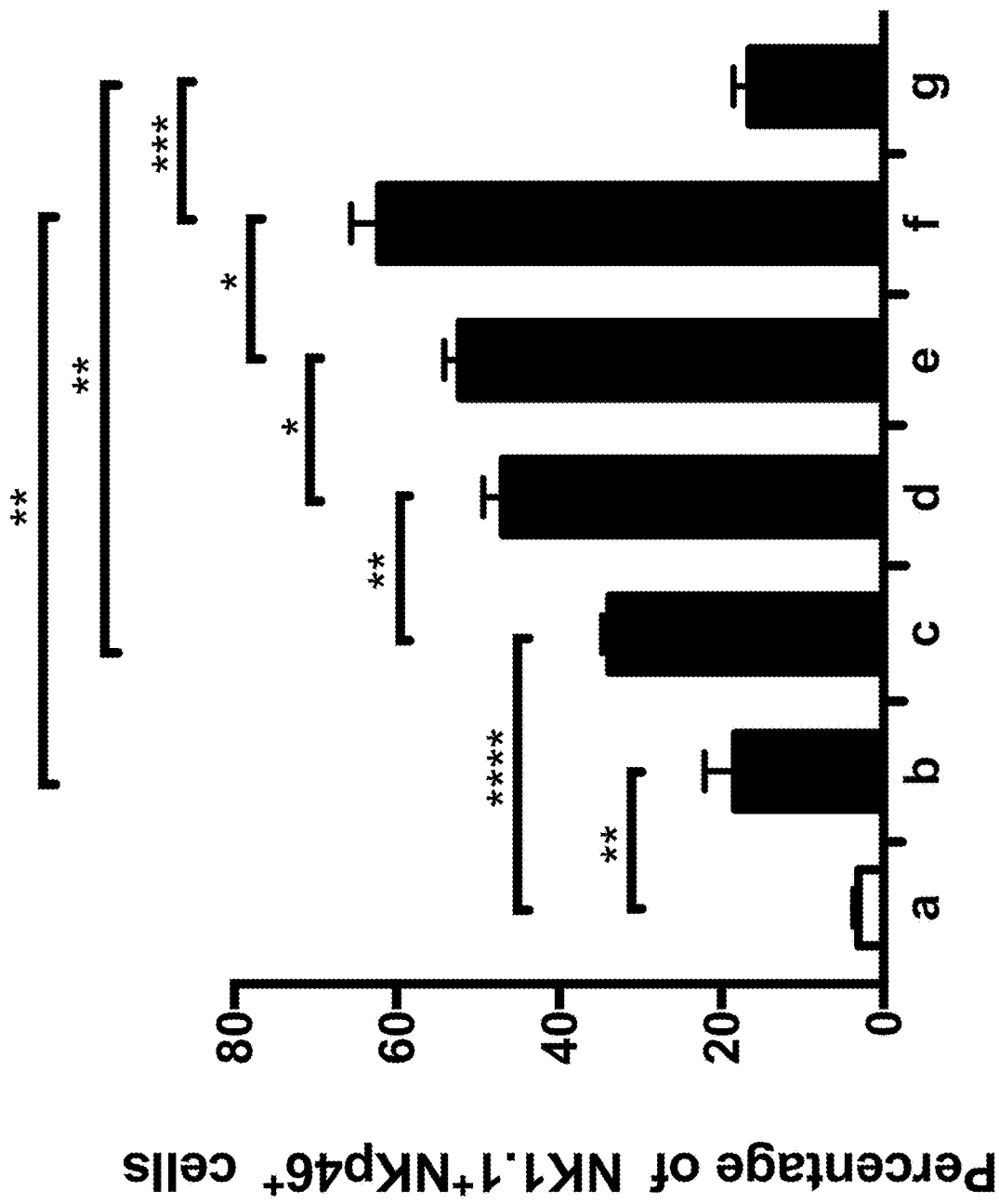
FIG. 14: Synergy between REV-ERB antagonism and the Notch ligand, rDLL4. The graph shows the percentage of mature (NK1.1$^+$NKp46$^+$) NK cells against the various conditions (as in FIG. 13). Condition f shows the strongest effect. Error bars show SEM. *, P≤0.05; , P≤0.01; *, P≤0.001; ****, P≤0.0001. These data represent technical triplicates of biological duplicates.

This experiment was repeated with an expanded set of culture conditions, as set out in FIG. 13. The results of this duplicate experiment are illustrated in FIG. 14. Again, this duplicate experiment demonstrated synergy between SR8278 and rDLL4. Condition f (SR8278 is added 2 days post isolation of bone marrow progenitors followed by exposure to rDLL4 2 days later) showed the strongest effect.

These data show that treatment of HPCs with SR8278 prior to (or simultaneously with) exposure to rDLL4 synergized to enhance NK cell production. E4bp4 is essential for the canonical production of NK cells. E4bp4 expression is increased by SR8278. Without being bound by theory, this can be explained by the induction of E4bp4 expression by SR8278, which in turn subsequently induces the expression of the Notch receptor. Later exposure to the Notch ligand, rDLL4 will maximize the effect on NK cell production.

Therefore, synergy between rDLL4 indicates that the rapid expansion of NK cells due to rDLL4 exposure following SR8278 treatment may well produce NK cells that have enhanced functionality in terms of their cytotoxicity, cytokine expression and survival post-transfusion to a recipient. Such NK cells would have a significant functional enhancement compared to existing techniques used to produce cells for adoptive transfer.

Figure 15:
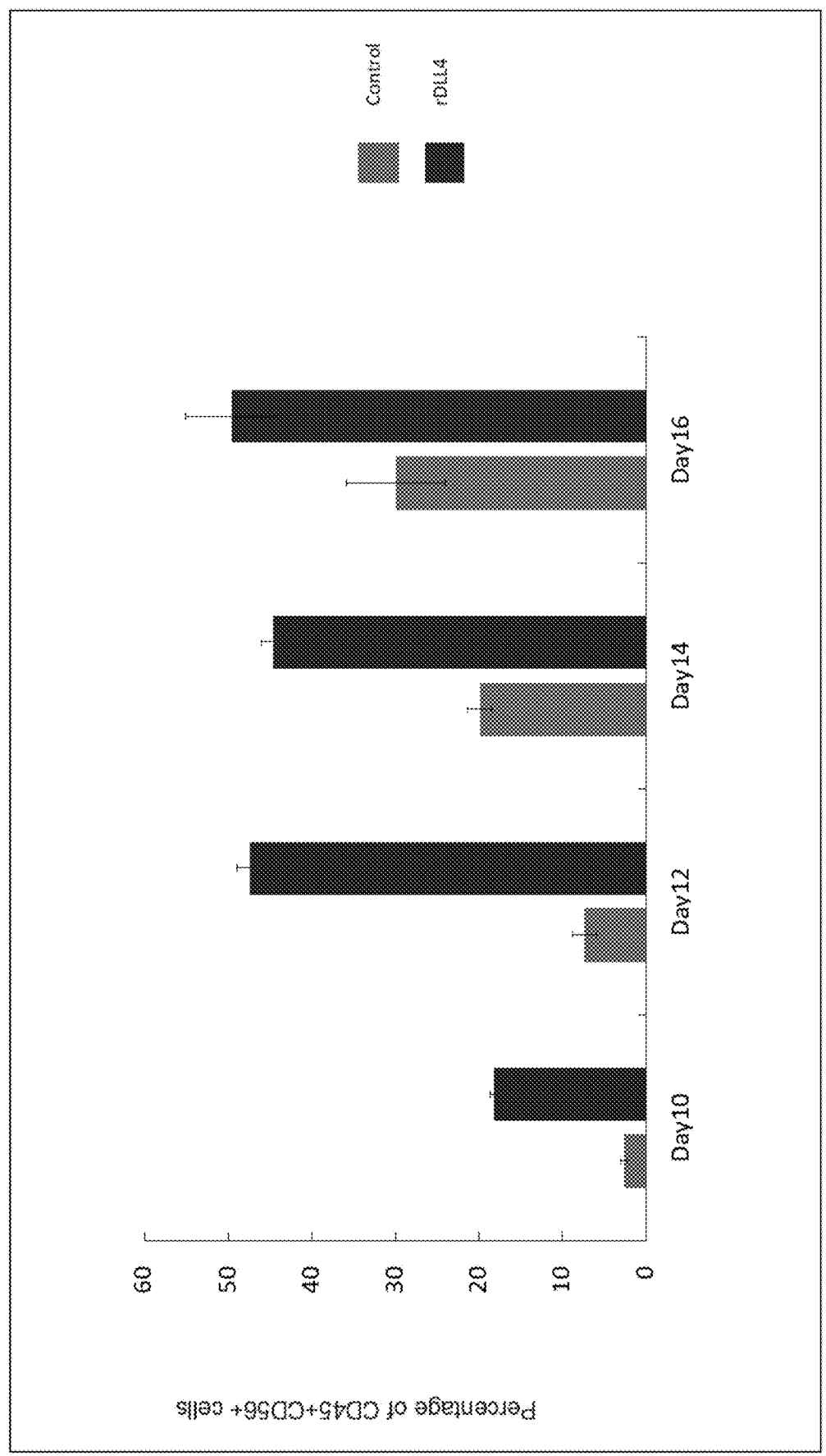
FIG. 15: Exposure to Notch ligand greatly accelerates the production of phenotypically mature human NK cells from human CD34$^+$ umbilical cord blood. The graph shows the percentage of mature (CD46$^+$/CD56$^+$) NK cells against time for human CD34$^+$ cells cultured under control condition (light grey bars) or on rDLL4 (dark grey bars).

Example 8—Exposure to Notch Ligand Greatly Accelerates the Production of Phenotypically Mature Human NK Cells As is shown in FIG. 15, exposure of human $CD34^+$ cord blood stem cells to the Notch ligand, rDLL4, significantly reduced the time required to produce a large population of mature human NK cells. In particular, exposure to rDLL4 resulted in the production of an NK cell population comprising almost 50% mature ($CD45^+/CD56^+$) NK cells after 12 days, compared with the control method in which only 30% mature NK cells were obtained even after 16 days. Populations with high percentages of mature NK cells are required by clinical protocols used for human NK cell production prior to transfusion to patients. Thus, the methods of the invention have the potential to greatly reduce any possible NK cell exhaustion phenotype which reduces the function of human NK cells after transfusion.

Materials and Methods
Mice
Wild type mice, E4bp4 heterozygous mice ($E4bp4^{+/-}$), E4bp4 knockout mice ($E4bp4^{-/-}$) and REV-ERB-α knockout mice ($Rev\text{-}erb\text{-}\alpha^{-/-}$) were used. All mice were on a C57BL/6 background, between 6 and 12 weeks old and matched for age and gender. $Rbpj^{flox/flox}$ mice were on a FVB background. All animal husbandry and experimental procedures were carried out according to UK Home Office regulations and local guidelines. E4bp4 mice were genotyped with the forward primer 5'CTCTGAGCTTGGCT-GATGTG3' (primer A) and reverse primer 5'GCTT-CAAGTCTCCACCAAGC3' (primer B) for detection of the wild type allele or 5'CCATGCTCCTGTCTTGATGA3' for detection of the null allele.

Cells and Cell Culture
OP9-GFP stromal cells were cultured in Iscove's Modified Dulbecco's Media (IMDM) (Sigma Aldrich) supplemented with 20% Fetal Bovine Serum (FBS), and Penicillin/Streptomycin (P/S). For experiments done on 96-well plates, OP9 stromal cells were plated at the concentration of 2000 cells/well and incubated at 37° C., 5% $CO_2$ for 1 day before the addition of HPCs. For experiments done on 24-well plates, OP9 stromal cells were plated at the concentration of 4000 cells/well and were incubated at 37° C. 5% $CO_2$ for 2 days prior to addition of HPCs. EL08.1D2 stromal cells were cultured in Minimum Essential Medium Eagle-Alpha Modification (Alpha-MEM) supplemented with 50% Myelocult M5300 (Stem Cell Technologies), 7.5% FBS, 50 μM β-Mercaptoethanol, 1 μM Hydrocortisone and 1% P/S (Sigma Aldrich). For human $CD34^+$ progenitor cell experiments, EL08.1D2 were irradiated at 3000 rads/30 Gy and plated in 96-well EmbryoMax Gelatin (Millipore)-coated plates at the concentration of 20,000 cells/well. There were cultured at 32° C., 5% $CO_2$ overnight, before $CD34^+$ cells were transferred onto them.

Mouse HPC Isolation
Lineage negative HPCs were purified from mouse bone marrow by crushing the leg bones in Phosphate-buffered Saline (PBS) with 2% fetal calf serum (FCS) (STEMCELL Technologies), topped up to 40 ml with magnetic-activated cell sorting (MACS) buffer (PBS, 2 mM EDTA, 0.5% BSA, sterile and filtered) and centrifuged at 800 g for 2 minutes. The cells were resuspended in PE-conjugated cocktail, (20 μl of anti-B220 (RA3-6B2), anti-mouse CD2 (RM2-5, anti-Ter119 (TER119) and anti-NK.1.1 (PK136) and 5 μl of anti-CD11b (M1/70) and anti-GR-1 (RB6-8C5) antibodies (all from Bioscience)) incubated for 5 minutes at 4° C., centrifuged and resuspended in anti-PE microbeads for 15 minutes at 4° C. Cells were washed in MACS buffer and passed through MACS columns. This allowed negative selection of HPCs. Following lineage depletion, 50 μl of the cells was analysed using flow cytometry to check for purity.

In Vitro Development of NK Cells from HPCs
The HPCs were plated and cultured in 24-well plates at a concentration of $5 \times 10^5$ HPCs/well in 1 ml of complete cytokine medium (Dulbecco's modified eagle medium (DMEM) (Sigma Aldrich), 10% FCS, 50 μM β-Mercaptoethanol, 10 ng/ml Flt3-ligand (Flt3L) (R&D Systems), 10 ng/ml IL-7 (R&D Systems), 100 ng/ml stem cell factor (SCF) (R&D Systems) and 1% P/S) for 2 days at 37° C., 5% $CO_2$. The HPCs were then transferred onto OP9 cells at 4500 cells/well for 96-well plate experiments and $3 \times 10^4$ cells/well for 24-well plate experiments in mouse NK cells differentiation medium (Alpha-MEM (Sigma Aldrich) plus 20% FCS, 1% P/S and 30 ng/ml IL-15). Cells were left in culture at 37° C., 5% $CO_2$ for 7 days with a change of mouse NK cells differentiation medium at day 3 or 4.

In Vitro Development of Human Umbilical Cord Blood Progenitor Cells
$CD34^+$ umbilical cord blood progenitor cells were provided by Anthony Nolan Research Institute, University College London. These cells were isolated from whole cord blood and were cryopreserved in liquid nitrogen for storage and transport. Cells were thawed, counted and then plated on EL08.1D2 plates prepared previously at a concentration of 1000 cells/well in human NK cells differentiation medium (Alpha-MEM plus 20% Human AB serum (Invitrogen), 50 µM β-Mercaptoethanol and 1% P/S along with 5 ng/ml human-IL-3 (Peprotech), 20 ng/ml human-IL-7 (Peprotech), 10 ng/ml human-Flt3-L (Peprotech), 20 ng/ml human-SCF (Peprotech) and 10 ng/ml human-IL-15 (Peprotech). Note that human-IL-3 is only needed for the first week of culture. Cells were left in the culture at 37° C., 5% $CO_2$ for 14 or 16 days with a change of human NK differentiation medium at day 7 and 12.

Flow Cytometry

Cells to be analysed by flow cytometry were passed through 40 µm cell strainers to remove clumps and washed with PBS buffer, centrifuged at 800 g for 2 minutes and resuspended in 100 µl fluorescent activated cell sorting (FACS) buffer (PBS plus 1% BSA) with appropriate fluorochrome conjugated antibodies at a dilution of 1 in 300. Cells were stained with the following antibodies, all of which were anti-mouse and are from eBioscience unless specified: 2B4 (clone m2B4(B6)458.1; BioLegend), CD2 (RM2-5), CD3 (17A2), CD11b (M1/70), CD19 (1D3), CD27 (LG.7F9), CD122 (TM-b1), CD127 (A7R34), B220 (RA3-6B2), ckit (ACK2), Flt3 (A2F10), Gr1 (RB6-8C5), NK1.1 (PK136), Sca1 (D7), Ter119 (TER119), NKp46 (29A1.4) anti-human CD45 (H130), anti-human CD2 (RPA-2.10) and anti-human CD56 (CMSSB). The lineage cocktail contained B220, CD2, CD11b, Gr1, NK1.1, and Ter119. Cells were stained in the dark at 4° C. for 30 minutes and then washed with 2 ml FACS buffer, centrifuged and resuspend in 300 µl FACS buffer plus Propidium Iodide (PI) also at a dilution of 1 in 300. Flow cytometry was performed using LSRFortessa™ cell analyser (Becton Dickinson Bioscience), sorted using FACSAria (Becton Dickinson) as indicated and full data analysis was done using FlowJo Software.

Polymerase Chain Reaction (PCR)

Individual PCR reactions contained 200 µM dNTPS, 1 µM forward primer (Primer A), 1 µM reverse primer (Primer B or C) and 0.5 U Taq polymerase. PCR reactions were set to the following conditions: 94° C. for 3 minutes (1 cycle); 94° C. for 30 seconds, 59° C. for 3 seconds, 72° C. for 45 seconds (40 cycles); 72° C. for 3 minutes (1 cycle); hold at 4° C.

DNA Electrophoresis

DNA electrophoresis was performed using 1% agarose (Sigma) dissolved in TAE buffer plus 500 ng/ml Ethidium Bromide (Sigma). DNA obtained from PCR reactions was analysed by gel electrophoresis was performed at 100 volts for approximately 45 minutes. Gels were imaged using EC3 Imaging System (Ultra Violet Products Ltd).

RNA Purification

RNA was extracted using Qiagen RNeasy Micro Kit according to the manufacture's protocol (Qiagen). Centrifugation was done at 8000 g for 15 seconds and the flow through discarded. Briefly, 350 µl of Buffer RLT+10% β-Mercaptoethanol were added to the harvested cells. RNA was further precipitated using 300 µl of 70% ethanol and transferred to RNeasy MinElute Spin Column and centrifuged. Next, 350 µl of buffer RW1 was added to the MinElute Spin Column and centrifuged. This was followed by the addition of 10 µl of DNase I (Qiagen) and 70 µl Buffer RDD (Qiagen) and left at room temperature for 15 minutes. 350 µl of Buffer RW1 was added to wash off DNase I and centrifuged. 500 µl of Buffer RPE was then added to the column and centrifuged, followed by the addition of 500 µl of 80% ethanol and centrifuged for 2 minutes. Finally, 14 µl of RNase-free water was added to elute the RNA and the column was spun for 1 minute at full speed. The concentration of RNA in each sample was measured using Nanodrop, and all samples were diluted to the same working concentration.

Reverse Transcription (Conversion of RNA into cDNA)

Reverse transcription was performed using Transcriptor First Strand cDNA Synthesis kit (Roche). Following the manufacturer's protocol, a template-primer mixture for one 20 µl reaction was prepared, where all reagents are provided in the kit: RNA (1 µg to 5 µg), 2 µl Random Hexamer Primer, top the reaction up to 13 µl with water (PCR-grade). Next, the template-primer mixture was denatured by heating the tube for 10 minutes at 65° C. to remove RNA secondary structures. To that template-primer mixture, 4 µl of Transcriptor Reverse Transcriptase Reaction Buffer, 0.5 µl of Protector RNase Inhibitor, 2 µl of Deoxynycleotide Mix and 0.5 µl of Transcriptor Reverse Transcriptase was added. The reagents was mixed and placed In a thermal block cycler with the following settings: 25° C. for 10 minutes; 55° C. for 30 minutes; 85° C. for 5 minutes and store at 4° C.

Quantification of Targeted Expressed RNA Using Realtime qPCR

| Temperature (° C.) | Time |
|---|---|
| 95 | 20 minutes |
| 95 | 3 seconds |
| 96 | 30 seconds |

Conditions Used for RT-qPCR

A standard curve was constructed using splenocytes cDNA diluted to 1, 1:10, 1:100, 1:1000 and 1:10000. To the 2 µl of cDNA produced in the previous step, 5 µl Taqman master mix (Applied Biosystem), 0.5 µl of Taqman gene expression assay kit of Hprt, Nfil3, Id2 or Eomes (Applied Biosystem) and 2.5 µl of RNase-free water. The program used is shown in Table 1 and the reaction was run for 47 cycles.

Analysis of SUMOylation In Vivo Using 6his-SUMO HeLa Cells

The HeLa cell lines 6His-SUMO-1, 6His-SUMO-2, 6His-SUMO-3 and parental HeLa cells were transfected with pCMV-E4BP4 or pCMV (empty vector). After an input sample was removed, the remaining cells were lysed in 6 M Guanidinium-HCl, before $Ni^{2+}$ affinity purification. $Ni^{2+}$ NTA agarose beads (Qiagen) were incubated with cell lysates overnight (O/N) at 4° C. Samples were washed with 8 M Urea and His-tagged proteins were eluted with 200 mM imidazole.

Immunoprecipitation of FLAG-E4bp4

E4bp4 cDNA was cloned into the pCMV-script vector (Promega) using primers to incorporate a 5' FLAG tag after the start codon. HeLa cell lines 6His-SUMO1, 6His-SUMO2 and 6His-SUMO3 were transfected with pCMV-FLAG-E4bp4 or pCMV (empty vector). Cells were lysed using a two-step lysis protocol and lysates were incubated with anti-FLAG M2 Affinity Gel (Sigma Aldrich) O/N at 4° C. Samples were centrifuged and the supernatant was removed. Each sample was washed with TBS (50 mM Tris-HCl, 50 mM NaCl, pH 7.4) before elution of purified material by Laemmli sample buffer.

Western Blotting

Cell lysates and protein samples were mixed 1:1 with Laemmli sample buffer and reduced by boiling in 5% β-mercaptoethanol. Samples were separated on 8% polyacrylamide gels, transferred to PVDF membranes and membranes were probed with primary antibodies against: E4bp4 (C18; Santa Cruz Biotech), SUMO2/3 (AbCam), FLAG (M2; Sigma Aldrich), 6x-His (4D11; AbCam), α-Tubulin (DM1A; eBioscience), RanGAP1 (AbCam), Histone H3 (AbCam). Appropriate HRP-conjugated secondary antibodies (Abam) were used with Western Lightning® Plus-ECL detection reagents (Perkin Elmer) to determine chemiluminescence. Images of exposed blots were digitally acquired using the ChemiDoc™ XRS+ system (Bio-Rad).

Site Directed Mutagenesis

Single base pair mutations were made in the E4bp4 cDNA (K10R, K116R, K219R, K337R, K394R, S286A, S301A, and S353A), in the pCMV-script expression vector, using the QuikChange® XL site-directed mutagenesis kit (Agilent) and appropriately designed primers. Each mutant was also cloned into the pMSCV-IRES-hCD2 retroviral expression vector. The 5x-SUMO and S286-353A mutants were also cloned into the lentiviral expression vector pCSGW.

Mass Spectrometry Analysis 293T cells were transfected with pCMV-FLAG-E4bp4 and pCDNA3-VP35 using Lipofectamine 2000 (Life Technologies). The presence of the Ebola virus VP35 protein, helped to enhance recombinant protein expression. E4bp4 was immunoprecipitated from whole cell lysates using anti-FLAG M2 Affinity Gel (Sigma Aldrich). Bound material was eluted using 150 ng/μl FLAG peptide (Sigma Aldrich). Purified E4bp4 was concentrated using vacuum centrifugation and resuspended in 100 mM ammonium bicarbonate pH 8. Samples were reduced with 5 mM dithiothreitoland 14 mM iodoacetamide was used to label reduced cysteines. Proteomics-grade trypsin (Promega) was used to digest the E4bp4 protein for 6 h at 37° C. For SUMOylated peptide analysis samples were sequentially digested with GluC (Roche) for 6 h at RT.

Phosphorylated peptides were enriched using $TiO_2$ (GL sciences) and phosphopeptides were eluted with 150 mM ammonium hydroxide and 50% acetonitrile (v/v) (Millipore). Peptides were chromatographically resolved on an Ultimate 3000 RS-LC-nano System (Dionex), with an Acclaim PepMap100, C18 stationary phase (Thermo Fisher). Real-time tandem mass spectra were acquired on an LTQ Velos Pro linear ion trap (Thermo Scientific). Initial phosphopeptide identification from the LC-MS/MS data was performed using a Sequest search in Proteome discoverer 1.3 (Thermo Fisher) against the Mouse Uniprot database (accessed: 19/08/14) including dynamic side-chain modifications including phosphorylation (+79.966) on serine, threonine, and tyrosine residues. Putative phosphopeptides were then validated using an algorithm for phosphorylation site identification and manually assessed for accuracy.

The SUMOylated peptides were analysed using a mixture of data-dependent acquisitions and targeted MS/MS scans to search for peptides containing putative sites of SUMOylation based on a SUMO tag of GGTQQFV. Specifically, targeted MS/MS scans were always collected for the following m/z values, which correspond to E4bp4 peptides predicted to have SUMOylated lysines: K10 m/z 2+=531.99; K116 m/z 2+=796.49; K219 m/z 2+=853.54; K337 m/z 2+=825.52).

Cycloheximide Time Course

3T3 cells were stably transduced with pMSCV-E4bp4-hCD2 (or E4bp4 mutant versions) and after 48 h cells were bulked sorted for high hCD2 expression. Transduced cell lines were incubated with 50 μg/ml cycloheximide (Sigma-Aldrich) for 0-16 h. Nuclear extracts were prepared for all samples using NE-PER extraction regents (Pierce).

Luciferase Assay

E4bp4 transcriptional activity was analysed using the pGL3-E4bp4-CS vector24, containing the Firefly luciferase reporter gene and the Dual-Luciferase® reporter assay system (Promega). 3T3 cells were transfected with pMSCV-E4bp4-hCD2, pGL3-E4bp4-CS (or empty vector) and pRL-CMV (normalisation control). After 48 h, cells were lysed and the Dual-Luciferase® reporter assay system was used to determine Luciferase activities.

Quantitative PCR

MNK-1 cells were transduced with pCSGW-E4bp4 (or E4bp4 5x SUMO or E4bp4 S286-353A mutants). RNA was isolated using the RNeasy mini kit (Qiagen) and cDNA was synthesised using 1st Strand cDNA synthesis kit (Roche). QPCR was performed using TaqMan (Life Technologies) assays for Hprt1 (Mm00446968_ml), E4bp4 (E4bp4; Mm00600292_s1), Eomes (Mm01351985_m1), Gata3 (Mm00484683_m1), Notch1 (Mm00435249_m1) and T-bet (Tbx21; Mm00450960_ml). Samples were analysed using an Applied Biosystems 7500 Fast Real-Time PCR system. Ct values from samples were compared with a standard curve made from a known concentration of plasmid DNA (Eomes, T-bet, Gata3) or cDNA from a known number of murine splenocytes (Notch, Hprt1). The expression of all genes was normalised to Hprt1.

Chromatin Immunoprecipitation

Regulatory regions of Notch1 were searched for putative E4bp4-binding sites (T(T/G)A(T/C)GTAA) using MatInspector (Genomatix). MNK-1 cells were transduced with a lentivirus expressing FLAG-E4bp4 and ChIP immunoprecipitation performed. Briefly, protein-DNA complexes were immunoprecipitated with IgG (EMD Millipore), M2 antibody to FLAG (Sigma-Aldrich), or polyclonal E16 antibody to E4bp4 (Santa Cruz Biotechnology, Inc.). Purified DNA was amplified using SYBR Select master mix (Life Technologies) and primers designed to recognise putative E4bp4-binding regions (Table 2).

TABLE 2

Primers for the amplification of putative E4bp4-binding regions in Notch1 locus

| Region | Forward primer (5'-3') | Reverse primer (5'-3') | Amplicon (bp) |
| --- | --- | --- | --- |
| Notch1 A | CTATATTTTT GCCTTGACAG CTAAAGG | GAAGTACGAA GCATGCTTGC | 168 |
| Notch1 B | CACATCTGTG AGCTATTTTT GG | GACTGACTAA ACTAACATTC CCAC | 170 |
| Notch1 C | CTCAGAAACT GGCCTCAAGC | CACTTGCAGT CAGGCGTTC | 144 |
| Notch1 D | CACGCCATCT TAAAGAGCTC | GTAACCAACT GCACTCTTCT CC | 135 |
| Notch1 E | CACCAAGAAT TCCCAGGAG | GAGTGCAGTC ACGTGCTGAC | 144 |

TABLE 2-continued

Primers for the amplification of putative E4bp4-binding regions in Notch1 locus

| Region | Forward primer (5'-3') | Reverse primer (5'-3') | Amplicon (bp) |
|---|---|---|---|
| Notch1 F | CTCAGACTCT CTCGGTAAGT GTC | CGTGTGGAGC TACTCTGGC | 160 |

In Vitro Development of NK Cells from Transduced Lineage Negative Bone Marrow Cells Lin⁻ BM cells were isolated from mouse leg bones and cultured in DMEM supplemented with 10% FCS (Stemcell Technologies), 50 µM β-mercaptoethanol (Gibco), 10 ng/ml Flt3L (PeproTech), 10 ng/ml IL-7 (PeproTech), and 100 ng/ml SCF (PeproTech). After 48 h cells were transduced by spinfection at 700 g and 20° C. for 45 min with 8 µg/ml Polybrene. For positive controls, cells were transduced with pMSCV-IRES-hCD2, containing WT E4bp4. Transduced cells were cultured for 72 h before being resuspended in α-MEM supplemented with 20% FCS, β-mercaptoethanol, and 30 ng/ml IL-15 (PeproTech) and re-plated onto OP9 stromal cells for a further 7 days of culture.

To investigate Notch1 signalling, Lin⁻ BM cells were cultured on OP9, OP9-DL1 or plates pre-coated with rDLL1 (R&D Systems) or rDLL4 (R&D Systems). Plates were pre-coated with 10 µg/ml rDLL1/rDLL4 for 3 h at room temperature. Cells were incubated in α-MEM supplemented with 10% FCS, β-mercaptoethanol, 1 mM Sodium Pyrvuate, 25 mM HEPES and for the first 7 days with Flt3L, IL-7, and SCF. Cells were incubated for another 7 days on either on OP9 or OP9-DL1 in the presence of IL-15.

Rbpj$^{flox/flox}$ Lin⁻ BM cells were lentivirally transduced on the day of isolation with pCSGW-Cre (or empty vector) that co-expresses hCD2. Cells were transduced by spinfection and were cultured for two days in the presence of Flt3L, IL-7, and SCF. Cells were either transferred onto rDLL4-coated plates for three more days of culture or transferred directly on OP9. Cells were cultured on OP9 for 7 days with IL-15. For flow cytometry analysis, all cells were gated for hCD2 expression to identify the population transduced with lentivirus.

Statistical Analysis

Statistical analysis was done using Mann-Whitney test in GraphPad Prism 7

Discussion

NK cells are lymphocytes that are capable of producing cytokines, influencing other immune cells as well as killing cancerous, pathogen-infected or damaged cells directly. Due to these properties, researchers are interested in boosting the number of NK cells in order to enhance cytotoxicity against cancerous or pathogen-infected cells. NK cells develop from HSCs in the bone marrow and are controlled by a tightly regulated process involving various transcription factors and cytokines. E4bp4 is the most critical gene regulating NK cell development. E4bp4 has a profound effect on NK cell production despite there being only a relatively small increase in E4bp4 mRNA levels during NK cell development. Little is known about any means that exist to control the activity of E4bp4 protein. The ability to control E4bp4 expression would have highly significant implications for the development and production of NK cells.

The present inventions have previously demonstrated that upon administration of SR8278, the production of NK cells in NK cell production assays increases more than 2-fold. In the assays conducted, the optimum time to add SR8278 to the HPC culture for in vitro NK cell production was at Day 2 and the optimum dose was 10 µM. The addition of SR8278 was also found to significantly increase human NK cell development from human HPCs cultured in vitro.

The present inventors have demonstrated that the E4bp4 protein has multiple SUMO modifications and is predominantly modified by the SUMO2/3 isoform. K219 as a site an endogenous site of SUMO modification. The MS analysis of the E4bp4 protein also revealed it is phosphorylated at three sites; S286, S301 and S353.

E4bp4 plays a central role in NK cell development where its expression in CLPs is required to commit developing cells to the NK lineage. The inventors have shown that the SUMOylation and phosphorylation sites of E4bp4 have a dramatic influence both on the activity of E4bp4 and on NK cell development. When comparing the activity of WT-form E4bp4 to mutant forms that lack SUMOylation or phosphorylation sites, the mutant forms were found to consistently promote greater levels of NK cell production. The two types of post-translational modification reported on herein, act in a similar manner to negatively regulate the activity of E4bp4 during NK cell production. E4bp4 was previously demonstrated to be a limiting factor for NK cell development, as transduction of E4bp4+/+ Lin− BM cells with E4bp4 caused increased levels of NK cell production3,5. Transducing E4bp4+/+ cells with mutant forms of E4bp4 also increased NK cell production but to a greater extent than the WT-form E4bp4. This demonstrated that SUMOylation and phosphorylation both negatively regulate the activity of E4bp4, as removing the sites of these modifications increases E4bp4 activity and ultimately NK cell production. As E4bp4 is critical for NK cell development, it is highly likely that its activity is tightly controlled by multiple mechanisms as aberrant activity could lead to defective haematopoiesis. There are no other well characterized examples where the PTM of a single transcription factor can have such a dramatic effect on a complex biological process such as lineage development.

SUMOylation and phosphorylation were both found to suppress the transcriptional activity of E4bp4 regardless of whether it was activating or repressing transcription. The effect of WT-form E4bp4 and the PTM mutant forms on the expression of transcription factors known to regulate lymphoid commitment was compared. The remarkable outcome of this comparison was that Notch1 expression was upregulated in the presence of WT-form E4bp4 but that expression was significantly further enhanced in the presence of both the E4bp4 5×-SUMO mutant and the S286-353A phosphorylation mutant.

Notch signalling activated by extrinsic ligands has previously been suggested to have a role in the development of both murine and human NK cells. It must act transiently during the early phase of NK cell development, as prolonged signalling induces T cell development. The inventors have shown that Cre-mediated deletion of Rbpj in HPCs results in impaired NK cell development, which is the first report of an intrinsic role for Notch in NK cell development. In particular, the data herein demonstrates that Notch signalling significantly enhances NK cell development. In particular, mice with conditional deletion of Notch1 in their haematopoietic cells do not have significantly reduced numbers of NK cells. This could be because the E4bp4-mediated transcriptional network in the conditional knockout cells remains intact and can compensate for the lack of Notch1. Early stages of NK cell development may be somewhat impaired with Notch1 deleted, but homeostatic processes could lead to the accumulation of normal numbers of peripheral NK cells in steady state conditions.

Like Notch, E4bp4 is required during early lymphocyte development and must be expressed in CLPs for them to commit to the NK lineage, however it is dispensable for the maturation and functionality of mature NK cell8. E4bp4 and Notch1 are also important for the development of other innate lymphoid cell types, for example, lymphoid tissue inducer (LTi) cells, where Notch signalling is required to engage the LTi developmental pathway but needs to be turned off later to avoid diversion to T cell fate. The inventors have found that E4bp4 transcriptionally regulates Notch1 as it binds directly to regulatory regions of the Notch1 gene and in the absence of E4bp4, Notch1 expression was reduced in HPCs. E4bp4 most prominently bound to a region 1.8 Kb upstream of the TSS of Notch1 in a similar manner to other transcription factors, such as DLX5 and ERβ, known to regulate Notch1 expression. Strikingly, increased Notch signalling during the early part of NK cell development alone was sufficient to completely rescue the development of NK cells from E4bp4$^{-/-}$ -progenitor cells. This strongly suggests that Notch1 acts downstream of E4bp4 during NK cell development. This rescue was only achieved when Notch ligands were present during the early stage of NK cell development. The rescue from E4bp4$^{-/-}$ progenitors was achieved using both DLL1 expressing OP9 stromal cells and rDLL1 and rDLL4 proteins immobilised on plastic plates. The rDLL4 had a much greater effect than the rDLL1 on NK cell development as DLL4 binds Notch1 with much higher affinity than DLL1.

As Notch1 ligands are expressed in the bone marrow microenvironment, it appears that the availability of Notch signalling at the appropriate time can drive NK cell development. Similarly to E4bp4, Notch1 has also been found to regulate the expression of Eomes48, which could be a further means by which Notch1 enhances NK cell development via the E4bp4-regulated pathway. Thus, the data shown here for NK cells is indicative of a central mechanism linking extrinsic signals via E4bp4 to direct transcriptional control of all ILC production.

In sum, control of E4bp4 expression and/or activity by extrinsic stimuli such as Notch ligands has significant implications for the production of human NK cells for use in immunotherapy. The conventional methods for the production of NK cells from various sources (e.g. induced-pluripotent stem cells and umbilical cord blood stem cells) involves the use of cytokines and stromal cells to commit the cells to the NK lineage, but influencing E4bp4 expression and/or activity, and/or Notch signalling could provide a simple strategy to enhance the process. Thus, the manipulation of E4bp4 activity and/or expression and/or Notch signalling, either alone, and particularly in combination, has potential utility in the production of future NK cell immunotherapeutic products, including the direct mobilisation of NK cell production in vivo as immunotherapy.

The invention claimed is:

1. An ex vivo method for expanding a natural killer (NK) cell population, comprising the steps of:
   a) culturing an haematopoietic progenitor cell (HPC) comprising sample obtained from an individual with a compound that inhibits the action of REV-ERB;
   b) culturing said cells in the presence of a Notch ligand; and
   c) expanding said cells in vitro to produce an NK cell population.

2. The method of claim 1, wherein the vessel in which the HPCs are cultured is coated with the Notch ligand.

3. The method of claim 1, wherein the Notch ligand is delta-like ligand 4 (DLL4), or a fragment thereof which retains the function of DLL4.

4. The method of claim 1, wherein said compound increases E4bp4 expression by decreasing REV-ERB activity.

5. The method of claim 1, wherein said compound decreases the activity of REV-ERB-α and/or REV-ERB-β, preferably REV-ERB-β.

6. The method of claim 1, wherein said compound decreases the activity of REV-ERB-α and REV-ERB-β.

7. The method of claim 1, wherein said compound is a REV-ERB antagonist, preferably an antagonist of REV-ERB-α and REV-ERB-β.

8. The method of claim 1, wherein the compound is selected from a small molecule, a PROTAC reagent, a double stranded RNA (dsRNA), a small interfering RNA (siRNA), a small hairpin RNA (shRNA), a micro RNA, an antisense RNA, an aptamer, an antibody, a ribozyme, a peptide or a peptidomimetic.

9. The method of claim 8, wherein the compound is a small molecule.

10. The method of claim 1, wherein the compound is SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine, preferably SR8278.

11. The method of claim 1, wherein the compound is added no later than 2 days after isolating the HPCs in the sample of claim 1(a), and optionally the Notch ligand is present on or from 4 days after isolating said HPCs.

12. The method of claim 1, wherein the sample of HPCs is obtained from bone marrow, cord blood and/or peripheral blood.

13. The method of claim 1, wherein:
   a) the REV-ERB inhibitory compound is added before the Notch ligand; or
   b) the Notch ligand is added before the REV-ERB inhibitory compound.

14. The method of claim 1, wherein the Notch ligand and REV-ERB inhibitory compound are added simultaneously.

15. A method of treatment by increasing the number of NK cells in a patient in need thereof, comprising administering to said patient a therapeutically effective amount of a compound which inhibits the action of REV-ERB as defined in claim 7 and a Notch ligand.

16. The method of claim 15, wherein the Notch ligand is delta-like ligand 4 (DLL4), or a fragment thereof which retains the function of DLL4.

17. The method of claim 15, wherein the compound and Notch ligand are used in combination with antibody-mediated immunotherapy.

* * * * *

SEQUENCE LISTING

<160> NUMBER OF SEQ ID NOS: 51

<210> SEQ ID NO 1
<211> LENGTH: 2058
<212> TYPE: DNA
<213> ORGANISM: Homo sapiens

<400> SEQUENCE: 1

```
atggcggcag cgtcccggag cgcctctggc tgggcgctac tgctgctggt ggcactttgg      60
cagcagcgcg cggccggctc cggcgtcttc cagctgcagc tgcaggagtt catcaacgag     120
cgcggcgtac tggccagtgg gcggccttgc gagcccggct gccggacttt cttccgcgtc     180
tgccttaagc acttccaggc ggtcgtctcg cccggaccct gcaccttcgg gaccgtctcc     240
acgccggtat tgggcaccaa ctccttcgct gtccgggacg acagtagcgg cggggggcgc     300
aaccctctcc aactgccctt caatttcacc tggccgggta ccttctcgct catcatcgaa     360
gcttggcacg cgccaggaga cgacctgcgg ccagaggcct tgccaccaga tgcactcatc     420
agcaagatcg ccatccaggg ctccctagct gtgggtcaga actggttatt ggatgagcaa     480
accagcaccc tcacaaggct gcgctactct taccgggtca tctgcagtga caactactat     540
ggagacaact gctcccgcct gtgcaagaag cgcaatgacc acttcggcca ctatgtgtgc     600
cagccagatg gcaacttgtc ctgcctgccc ggttggactg gggaatattg ccaacagcct     660
atctgtcttt cgggctgtca tgaacagaat ggctactgca gcaagccagc agagtgcctc     720
tgccgcccag gctggcaggg ccggctgtgt aacgaatgca tcccccacaa tggctgtcgc     780
cacggcacct gcagcactcc ctggcaatgt acttgtgatg agggctgggg aggcctgttt     840
tgtgaccaag atctcaacta ctgcacccac cactccccat gcaagaatgg ggcaacgtgc     900
tccaacagtg ggcagcgaag ctacacctgc acctgtcgcc caggctacac tggtgtggac     960
```

-continued

```
tgtgagctgg agctcagcga gtgtgacagc aaccccctgtc gcaatggagg cagctgtaag    1020
gaccaggagg atggctacca ctgcctgtgt cctccgggct actatggcct gcattgtgaa    1080
cacagcacct tgagctgcgc cgactccccc tgcttcaatg ggggctcctg ccgggagcgc    1140
aaccaggggg ccaactatgc ttgtgaatgt cccccccaact tcaccggctc caactgcgag    1200
aagaaagtgg acaggtgcac cagcaacccc tgtgccaacg ggggacagtg cctgaaccga    1260
ggtccaagcc gcatgtgccg ctgccgtcct ggattcacgg gcacctactg tgaactccac    1320
gtcagcgact gtgcccgtaa cccttgcgcc cacggtggca cttgccatga cctggagaat    1380
gggctcatgt gcacctgccc ctgccggctt ctctggccgac gctgtgaggt gcggacatcc    1440
atcgatgcct gtgcctcgag tccctgcttc aacagggcca cctgctacac cgacctctcc    1500
acagacacct ttgtgtgcaa ctgcccttat ggctttgtgg gcagccgctg cgagttcccc    1560
gtgggcttgc cgcccagctt cccctgggtg gccgtctcgc tgggtgtggg gctggcagtg    1620
ctgctggtac tgctgggcat ggtggcagtg gctgtgcggc agctgcggct tcgacggccg    1680
gacgacggca gcagggaagc catgaacaac ttgtcggact tccagaagga caacctgatt    1740
cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc gggggaccat gccaggaaag tttccccaca gtgacaagag cttaggagag    1920
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                  2058
```

<210> SEQ ID NO 2
<211> LENGTH: 685
<212> TYPE: PRT
<213> ORGANISM: Homo sapiens

<400> SEQUENCE: 2

```
Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175
```

-continued

```
Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590
```

```
Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
            675                 680                 685

<210> SEQ ID NO 3
<211> LENGTH: 1923
<212> TYPE: DNA
<213> ORGANISM: Homo sapiens
<220> FEATURE:
<221> NAME/KEY: misc_feature
<222> LOCATION: (1833)..(1833)
<223> OTHER INFORMATION: n is a, c, g, or t

<400> SEQUENCE: 3
```

| | | | | | |
|---|---|---|---|---|---|
| gccccttct | ttctcctcgt | cggcccgaga | gcaggaacac | gataacgaag | gaggcccaac | 60 |
| ttcattcaat | aaggagcctg | acggatttat | cccagacggt | agaacaaaag | gaagaatatt | 120 |
| gatggatttt | aaaccagagt | ttttaaagag | cttgagaata | cggggaaatt | aatttgttct | 180 |
| cctacacaca | tagatagggt | aaggttgttt | ctgatgcagc | tgaaaaaat | gcagaccgtc | 240 |
| aaaaaggagc | aggcgtctct | tgatgccagt | agcaatgtgg | acaagatgat | ggtccttaat | 300 |
| tctgctttaa | cggaagtgtc | agaagactcc | acaacaggtg | aggacgtgct | tctcagtgaa | 360 |
| ggaagtgtgg | ggaagaacaa | atcttctgca | tgtcggagga | acggaaatt | cattcctgat | 420 |
| gaaaagaaag | atgctatgta | ttgggaaaaa | aggcggaaaa | ataatgaagc | tgccaaaaga | 480 |
| tctcgtgaga | agcgtcgact | gaatgacctg | gttttagaga | caaactaat | tgcactggga | 540 |
| gaagaaaacg | ccacttaaa | agctgagctg | ctttcactaa | aattaaagtt | tggtttaatt | 600 |
| agctccacag | catatgctca | agagattcag | aaactcagta | attctacagc | tgtgtacttt | 660 |
| caagattacc | agacttccaa | atccaatgtg | agttcatttg | tggacgagca | cgaaccctcg | 720 |
| atggtgtcaa | gtagttgtat | ttctgtcatt | aaacactctc | cacaaagctc | gctgtccgat | 780 |
| gtttcagaag | tgtcctcagt | agaacacacg | caggagagct | ctgtgcaggg | aagctgcaga | 840 |
| agtcctgaaa | acaagttcca | gattatcaag | caagagccga | tggaattaga | gagctacaca | 900 |
| agggagccaa | gagatgaccg | aggctcttac | acagcgtcca | tctatcaaaa | ctatatgggg | 960 |
| aattctttct | ctgggtactc | acactctccc | ccactactgc | aagtcaaccg | atcctccagc | 1020 |
| aactccccga | gaacgtcgga | aactgatgat | ggtgtggtag | aaagtcatc | tgatggagaa | 1080 |
| gacgagcaac | aggtcccaa | gggccccatc | cattctccag | ttgaactcaa | gcatgtgcat | 1140 |
| gcaactgtgg | ttaaagttcc | agaagtgaat | tcctctgcct | tgccacacaa | gctccggatc | 1200 |
| aaagccaaag | ccatgcagat | caaagtagaa | gcctttgata | tgaatttga | ggccacgcaa | 1260 |
| aaacttccct | cacctattga | catgacatct | aaaagacatt | tcgaactcga | aaagcatagt | 1320 |
| gccccaagta | tggtacattc | ttctcttact | cctttctcag | tgcaagtgac | taacattcaa | 1380 |
| gattggtctc | tcaaatcgga | gcactggcat | caaaaagaac | tgagtggcaa | aactcagaat | 1440 |

```
agtttcaaaa ctggagttgt tgaaatgaaa gacagtggct acaaagtttc tgacccagag    1500
aacttgtatt tgaagcaggg gatagcaaac ttatctgcag aggttgtctc actcaagaga    1560
cttatagcca cacaaccaat ctctgcttca gactctgggt aaattactac tgagtaagag    1620
ctgggcattt agaaagatgt catttgcaat agagcagtcc attttgtatt atgctgaatt    1680
ttcactggac ctgtgatgtc atttcactgt gatgtgcaca tgttgtctgt tggtgtctt     1740 tttgtgcaca gattatgatg aagattagat tgtgttatca ctctgcctgt gtatagtcag    1800
atagtcatat gcgtaaggct gtatatatta agntttatt tttgttgttc tattataaag     1860
tgtgtaagtt accagtttca ataaggatt ggtgacaaac acagaaaaaa aaaaaaaaa      1920 aaa                                                                   1923

<210> SEQ ID NO 4
<211> LENGTH: 462
<212> TYPE: PRT
<213> ORGANISM: Homo sapiens

<400> SEQUENCE: 4

Met Gln Leu Arg Lys Met Gln Thr Val Lys Glu Gln Ala Ser Leu
1               5                   10                  15

Asp Ala Ser Ser Asn Val Asp Lys Met Met Val Leu Asn Ser Ala Leu
                20                  25                  30

Thr Glu Val Ser Glu Asp Ser Thr Thr Gly Glu Asp Val Leu Leu Ser
            35                  40                  45

Glu Gly Ser Val Gly Lys Asn Lys Ser Ala Cys Arg Arg Lys Arg
        50                  55                  60

Glu Phe Ile Pro Asp Glu Lys Lys Asp Ala Met Tyr Trp Glu Lys Arg
65                  70                  75                  80

Arg Lys Asn Asn Glu Ala Ala Lys Arg Ser Arg Glu Lys Arg Arg Leu
                85                  90                  95

Asn Asp Leu Val Leu Glu Asn Lys Leu Ile Ala Leu Gly Glu Glu Asn
            100                 105                 110

Ala Thr Leu Lys Ala Glu Leu Leu Ser Leu Lys Leu Lys Phe Gly Leu
        115                 120                 125

Ile Ser Ser Thr Ala Tyr Ala Gln Glu Ile Gln Lys Leu Ser Asn Ser
    130                 135                 140

Thr Ala Val Tyr Phe Gln Asp Tyr Gln Thr Ser Lys Ser Asn Val Ser
145                 150                 155                 160

Ser Phe Val Asp Glu His Glu Pro Ser Met Val Ser Ser Ser Cys Ile
                165                 170                 175

Ser Val Ile Lys His Ser Pro Gln Ser Ser Leu Ser Asp Val Ser Glu
            180                 185                 190

Val Ser Ser Val Glu His Thr Gln Glu Ser Ser Val Gln Gly Ser Cys
        195                 200                 205

Arg Ser Pro Glu Asn Lys Phe Gln Ile Ile Lys Gln Glu Pro Met Glu
    210                 215                 220

Leu Glu Ser Tyr Thr Arg Glu Pro Arg Asp Asp Arg Gly Ser Tyr Thr
225                 230                 235                 240

Ala Ser Ile Tyr Gln Asn Tyr Met Gly Asn Ser Phe Ser Gly Tyr Ser
                245                 250                 255

His Ser Pro Pro Leu Leu Gln Val Asn Arg Ser Ser Asn Ser Pro
            260                 265                 270

Arg Thr Ser Glu Thr Asp Asp Gly Val Val Gly Lys Ser Ser Asp Gly
        275                 280                 285
```

| | | | | | | | | | | | | |
|---|---|---|---|---|---|---|---|---|---|---|---|---|
|Glu|Asp|Glu|Gln|Gln|Val|Pro|Lys|Gly|Pro|Ile|His|Ser|Pro|Val|Glu|
| |290| | | |295| | | |300| | | | | | |

Leu Lys His Val His Ala Thr Val Val Lys Val Pro Glu Val Asn Ser
305                 310                 315                 320

Ser Ala Leu Pro His Lys Leu Arg Ile Lys Ala Lys Ala Met Gln Ile
            325                 330                 335

Lys Val Glu Ala Phe Asp Asn Glu Phe Glu Ala Thr Gln Lys Leu Ser
        340                 345                 350

Ser Pro Ile Asp Met Thr Ser Lys Arg His Phe Glu Leu Glu Lys His
        355                 360                 365

Ser Ala Pro Ser Met Val His Ser Ser Leu Thr Pro Phe Ser Val Gln
        370                 375                 380

Val Thr Asn Ile Gln Asp Trp Ser Leu Lys Ser Glu His Trp His Gln
385                 390                 395                 400

Lys Glu Leu Ser Gly Lys Thr Gln Asn Ser Phe Lys Thr Gly Val Val
            405                 410                 415

Glu Met Lys Asp Ser Gly Tyr Lys Val Ser Asp Pro Glu Asn Leu Tyr
            420                 425                 430

Leu Lys Gln Gly Ile Ala Asn Leu Ser Ala Glu Val Val Ser Leu Lys
            435                 440                 445

Arg Leu Ile Ala Thr Gln Pro Ile Ser Ala Ser Asp Ser Gly
    450                 455                 460

<210> SEQ ID NO 5
<211> LENGTH: 2793
<212> TYPE: DNA
<213> ORGANISM: Homo sapiens

<400> SEQUENCE: 5

```
gggcacgagg cgctccctgg gatcacatgg tacctgctcc agtgccgcgt gcggcccggg      60
aaccctgggc tgctggcgcc tgcgcagagc cctctgtccc agggaaaggc tcgggcaaaa     120
ggcggctgag attggcagag tgaaatatta ctgccgaggg aacgtagcag ggcacacgtc     180
tcgcctcttt gcgactcggt gccccgtttc tccccatcac ctacttactt cctggttgca     240
acctctcttc ctctgggact tttgcaccgg gagctccaga ttcgccaccc cgcagcgctg     300
cggagccggc aggcagaggc accccgtaca ctgcagagac ccgaccctcc ttgctacctt     360
ctagccagaa ctactgcagg ctgattcccc ctacacactc tctctgctct tcccatgcaa     420
agcagaactc cgttgcctca cgtccaacc cttctgcagg ctgcagtcc ggccacccca      480 agaccttgct gcagggtgct tcggatcctg atcgtgagtc gcggggtcca ctccccgccc     540
ttagccagtg cccaggggc aacagcggcg atcgcaacct ctagtttgag tcaaggtcca      600
gtttgaatga ccgctctcag ctggtgaaga catgacgacc ctggactcca acaacaacac     660
aggtggcgtc atcacctaca ttggctccag tggctcctcc caagccgca ccagccctga      720 atccctctat agtgacaact ccaatggcag cttccagtcc ctgacccaag ctgtcccac      780 ctacttccca ccatccccca ctggctccct cacccaagac ccggctcgct cctttgggag     840
cattccaccc agcctgagtg atgacggctc cccttcttcc tcatcttcct cgtcgtcatc     900
ctcctcctcc ttctataatg ggagccccc tgggagtcta caagtggcca tggaggacag     960
cagccgagtg tcccccagca agagcaccag caacatcacc aagctgaatg catggtgtt    1020 actgtgtaaa gtgtgtgggg acgttgcctc gggcttccac tacggtgtgc acgcctgcga    1080
gggctgcaag ggcttttttcc gtcggagcat ccagcagaac atccagtaca aaggtgtct    1140
```

```
gaagaatgag aattgctcca tcgtccgcat caatcgcaac cgctgccagc aatgtcgctt    1200
caagaagtgt ctctctgtgg gcatgtctcg agacgctgtg cgttttgggc gcatccccaa    1260
acgagagaag cagcggatgc ttgctgagat gcagagtgcc atgaacctgg ccaacaacca    1320
gttgagcagc cagtgccgc tggagacttc acccacccag cacccaccc caggccccat      1380 gggcccctcg ccaccccctg ctccggtccc ctcacccctg gtgggcttct cccagtttcc    1440
acaacagctg acgcctccca gatccccaag ccctgagccc acagtggagg atgtgatatc    1500
ccaggtggcc cgggcccatc gagagatctt cacctacgcc catgacaagc tgggcagctc    1560
acctggcaac ttcaatgcca accatgcatc aggtagccct ccagccacca ccccacatcg    1620
ctgggaaaat cagggctgcc cacctgcccc caatgacaac aacaccttgg ctgcccagcg    1680
tcataacgag gccctaaatg gtctgcgcca ggctccctcc tcctaccctc ccacctggcc    1740
tcctggcccc tgcacaccaca gctgccacca gtccaacagc aacgggcacc gtctatgccc    1800
cacccacgtg tatgcagccc cagaaggcaa ggcacctgcc aacagtcccc ggcagggcaa    1860
ctcaaagaat gttctgctgg catgtcctat gaacatgtac ccgcatggac gcagtgggcg    1920
aacggtgcag gagatctggg aggatttctc catgagcttc acgcccgctg tgcgggaggt    1980
ggtagagttt gccaaacaca tcccgggctt ccgtgacctt tctcagcatg accaagtcac    2040
cctgcttaag gctggcacct ttgaggtgct gatggtgcgc tttgcttcgt tgttcaacgt    2100
gaaggaccag acagtgatgt tcctaagccg caccacctac agcctgcagg agcttggtgc    2160
catgggcatg ggagacctgc tcagtgccat gttcgacttc agcgagaagc tcaactccct    2220
ggcgcttacc gaggaggagc tgggcctctt caccgcggtg gtgcttgtct ctgcagaccg    2280
ctcgggcatg gagaattccg cttcggtgga gcagctccag gagacgctgc tgcgggctct    2340
tcgggctctg gtgctgaaga accggccctt ggagacttcc cgcttcacca gctgctgct    2400 caagctgccg gacctgcgga ccctgaacaa catgcattcc gagaagctgc tgtccttccg    2460
ggtggacgcc cagtgacccg cccggccggc cttctgccgc tgcccccttg tacagaatcg    2520
aactctgcac ttctctctcc tttacgagac gaaaaggaaa agcaaaccag aatcttattt    2580
atattgttat aaaatattcc aagatgagcc tctggccccc tgagccttct tgtaaatacc    2640
tgcctccctc ccccatcacc gaacttcccc tcctccccta tttaaaccac tctgtctccc    2700
ccacaaccct cccctggccc tctgatttgt tctgttcctg tctcaaatcc aatagttcac    2760
agctgagctg gcttcaaaaa aaaaaaaaa aaa                                  2793
```

<210> SEQ ID NO 6
<211> LENGTH: 614
<212> TYPE: PRT
<213> ORGANISM: Homo sapiens

<400> SEQUENCE: 6

```
Met Thr Thr Leu Asp Ser Asn Asn Thr Gly Gly Val Ile Thr Tyr
1               5                   10                  15

Ile Gly Ser Ser Gly Ser Ser Pro Ser Arg Thr Ser Pro Glu Ser Leu
                20                  25                  30

Tyr Ser Asp Asn Ser Asn Gly Ser Phe Gln Ser Leu Thr Gln Gly Cys
            35                  40                  45

Pro Thr Tyr Phe Pro Pro Ser Pro Thr Gly Ser Leu Thr Gln Asp Pro
        50                  55                  60

Ala Arg Ser Phe Gly Ser Ile Pro Pro Ser Leu Ser Asp Asp Gly Ser
65                  70                  75                  80
```

```
Pro Ser Ser Ser Ser Ser Ser Ser Ser Ser Ser Phe Tyr Asn
            85                  90              95

Gly Ser Pro Pro Gly Ser Leu Gln Val Ala Met Glu Asp Ser Ser Arg
            100                 105                 110

Val Ser Pro Ser Lys Ser Thr Ser Asn Ile Thr Lys Leu Asn Gly Met
            115                 120                 125

Val Leu Leu Cys Lys Val Cys Gly Asp Val Ala Ser Gly Phe His Tyr
            130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
                180                 185                 190

Cys Leu Ser Val Gly Met Ser Arg Asp Ala Val Arg Phe Gly Arg Ile
            195                 200                 205

Pro Lys Arg Glu Lys Gln Arg Met Leu Ala Glu Met Gln Ser Ala Met
210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
            245                 250                 255

Ala Pro Val Pro Ser Pro Leu Val Gly Phe Ser Gln Phe Pro Gln Gln
            260                 265                 270

Leu Thr Pro Pro Arg Ser Pro Ser Pro Glu Pro Thr Val Glu Asp Val
            275                 280                 285

Ile Ser Gln Val Ala Arg Ala His Arg Glu Ile Phe Thr Tyr Ala His
290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
            325                 330                 335

Pro Pro Ala Pro Asn Asp Asn Asn Thr Leu Ala Ala Gln Arg His Asn
            340                 345                 350

Glu Ala Leu Asn Gly Leu Arg Gln Ala Pro Ser Ser Tyr Pro Pro Thr
            355                 360                 365

Trp Pro Pro Gly Pro Ala His His Ser Cys His Gln Ser Asn Ser Asn
            370                 375                 380

Gly His Arg Leu Cys Pro Thr His Val Tyr Ala Ala Pro Glu Gly Lys
385                 390                 395                 400

Ala Pro Ala Asn Ser Pro Arg Gln Gly Asn Ser Lys Asn Val Leu Leu
            405                 410                 415

Ala Cys Pro Met Asn Met Tyr Pro His Gly Arg Ser Gly Arg Thr Val
            420                 425                 430

Gln Glu Ile Trp Glu Asp Phe Ser Met Ser Phe Thr Pro Ala Val Arg
            435                 440                 445

Glu Val Val Glu Phe Ala Lys His Ile Pro Gly Phe Arg Asp Leu Ser
            450                 455                 460

Gln His Asp Gln Val Thr Leu Leu Lys Ala Gly Thr Phe Glu Val Leu
465                 470                 475                 480

Met Val Arg Phe Ala Ser Leu Phe Asn Val Lys Asp Gln Thr Val Met
            485                 490                 495
```

```
Phe Leu Ser Arg Thr Thr Tyr Ser Leu Gln Glu Leu Gly Ala Met Gly
                500                 505                 510

Met Gly Asp Leu Leu Ser Ala Met Phe Asp Phe Ser Glu Lys Leu Asn
    515                 520                 525

Ser Leu Ala Leu Thr Glu Glu Glu Leu Gly Leu Phe Thr Ala Val Val
530                 535                 540

Leu Val Ser Ala Asp Arg Ser Gly Met Glu Asn Ser Ala Ser Val Glu
545                 550                 555                 560

Gln Leu Gln Glu Thr Leu Leu Arg Ala Leu Arg Ala Leu Val Leu Lys
                565                 570                 575

Asn Arg Pro Leu Glu Thr Ser Arg Phe Thr Lys Leu Leu Leu Lys Leu
            580                 585                 590

Pro Asp Leu Arg Thr Leu Asn Asn Met His Ser Glu Lys Leu Leu Ser
            595                 600                 605

Phe Arg Val Asp Ala Gln
            610
```

<210> SEQ ID NO 7
<211> LENGTH: 1740
<212> TYPE: DNA
<213> ORGANISM: Homo sapiens
<220> FEATURE:
<221> NAME/KEY: misc_feature
<222> LOCATION: (994)..(994)
<223> OTHER INFORMATION: n is a, c, g, or t

<400> SEQUENCE: 7

```
atggaggtga atgcaggagg tgtgattgcc tatatcagtt cttccagctc agcctcaagc      60
cctgcctctt gtcacagtga gggttctgag aatagtttcc agtcctcctc ctcttctgtt     120
ccatcttctc caaatagctc taattctgat accaatggta atcccaagaa tggtgatctc     180
gccaatattg aaggcatctt gaagaatgat cgaatagatt gttctatgaa acaagcaaa     240
tcgagtgcac ctgggatgac aaaaaatcat agtggtgtga caaaatttag tggcatggtt     300
ctactgtgta agtctgtgg ggatgtggcg tcaggattcc actatggagt tcatgcttgc     360
gaaggctgta agggtttctt tcggagaagt attcaacaaa acatccagta caagaagtgc     420
ctgaagaatg aaaactgttc tataatgaga atgaatagga acagatgtca gcaatgtcgc     480
ttcaaaaagt gtctgtctgt tggaatgtca agagatgctg ttcggtttgg tcgtattcct     540
aagcgtgaaa acagaggat gctaattgaa atgcaaagtg caatgaagac catgatgaac     600
agccagttca gtggtcactt gcaaaatgac acattagtag aacatcatga acagacagcc     660
ttgccagccc aggaacagct gcgacccaag ccccaactgg agcaagaaaa catcaaaagc     720
tcttctcctc catcttctga tttttgcaaag gaagaagtga ttggcatggt gaccagagct     780
cacaaggata cctttatgta taatcaagag cagcaagaaa actcagctga gagcatgcag     840
ccccagagag gagaacggat tcccaagaac atggagcaat ataatttaaa tcatgatcat     900
tgcggcaatg gcttagcag ccattttccc tgtagtgaga gccagcagca tctcaatgga     960
cagttcaaag ggaggaatat aatgcattac ccanatggcc atgccatttg tattgcaaat    1020
ggacattgta tgaacttctc caatgcttat actcaaagag tatgtgatag agttccgata    1080
gatggatttt ctcagaatga aacaagaat agttacctgt gcaacactgg aggaagaatg    1140
catctggttt gtccaatgag taagtctcca tatgtggatc tcataaaatc aggacatgaa    1200
atctgggaag aattttcgat gagcttcact ccagcagtga agaagtggt ggaatttgca    1260
aagcgtattc ctgggttcag agatctctct cagcatgacc aggtcaacct tttaaaggct    1320
```

```
gggacttttg aggttttaat ggtacggttc gcatcattat ttgatgcaaa ggaacgtact    1380
gtcacctttt taagtggaaa gaaatatagt gtggatgatt tacactcaat gggagcaggg    1440
gatctgctaa actctatgtt tgaatttagt gagaagctaa atgccctcca acttagtgat    1500
gaagagatga gtttgtttac agctgttgtc ctggtatctg cagatcgatc tggaatagaa    1560
aacgtcaact ctgtggaggc tttgcaggaa actctcattc gtgcactaag gaccttaata    1620
atgaaaaacc atccaaatga ggcctctatt tttacaaaac tgcttctaaa gttgccagat    1680
cttcgatctt taaacaacat gcactctgag gagctcttgg cctttaaagt tcacccttaa    1740
```

<210> SEQ ID NO 8
<211> LENGTH: 578
<212> TYPE: PRT
<213> ORGANISM: Homo sapiens
<220> FEATURE:
<221> NAME/KEY: misc_feature
<222> LOCATION: (332)..(332)
<223> OTHER INFORMATION: Xaa can be any naturally occurring amino acid

<400> SEQUENCE: 8

```
Met Glu Val Asn Ala Gly Gly Val Ile Ala Tyr Ile Ser Ser Ser Ser
1               5                   10                  15

Ser Ala Ser Ser Pro Ala Ser Cys His Ser Glu Gly Ser Glu Asn Ser
                20                  25                  30

Phe Gln Ser Ser Ser Ser Val Pro Ser Ser Pro Asn Ser Ser Asn
            35                  40                  45

Ser Asp Thr Asn Gly Asn Pro Lys Asn Gly Asp Leu Ala Asn Ile Glu
    50                  55                  60

Gly Ile Leu Lys Asn Asp Arg Ile Asp Cys Ser Met Lys Thr Ser Lys
65                  70                  75                  80

Ser Ser Ala Pro Gly Met Thr Lys Asn His Ser Gly Val Thr Lys Phe
                85                  90                  95

Ser Gly Met Val Leu Leu Cys Lys Val Cys Gly Asp Val Ala Ser Gly
            100                 105                 110

Phe His Tyr Gly Val His Ala Cys Glu Gly Cys Lys Gly Phe Phe Arg
        115                 120                 125

Arg Ser Ile Gln Gln Asn Ile Gln Tyr Lys Lys Cys Leu Lys Asn Glu
    130                 135                 140

Asn Cys Ser Ile Met Arg Met Asn Arg Asn Arg Cys Gln Gln Cys Arg
145                 150                 155                 160

Phe Lys Lys Cys Leu Ser Val Gly Met Ser Arg Asp Ala Val Arg Phe
                165                 170                 175

Gly Arg Ile Pro Lys Arg Glu Lys Gln Arg Met Leu Ile Glu Met Gln
            180                 185                 190

Ser Ala Met Lys Thr Met Met Asn Ser Gln Phe Ser Gly His Leu Gln
        195                 200                 205

Asn Asp Thr Leu Val Glu His His Glu Gln Thr Ala Leu Pro Ala Gln
    210                 215                 220

Glu Gln Leu Arg Pro Lys Pro Gln Leu Glu Gln Glu Asn Ile Lys Ser
225                 230                 235                 240

Ser Ser Pro Pro Ser Ser Asp Phe Ala Lys Glu Glu Val Ile Gly Met
                245                 250                 255

Val Thr Arg Ala His Lys Asp Thr Phe Met Tyr Asn Gln Glu Gln Gln
            260                 265                 270
```

-continued

```
Glu Asn Ser Ala Glu Ser Met Gln Pro Gln Arg Gly Glu Arg Ile Pro
            275                 280                 285

Lys Asn Met Glu Gln Tyr Asn Leu Asn His Asp His Cys Gly Asn Gly
        290                 295                 300

Leu Ser Ser His Phe Pro Cys Ser Glu Ser Gln Gln His Leu Asn Gly
305                 310                 315                 320

Gln Phe Lys Gly Arg Asn Ile Met His Tyr Pro Xaa Gly His Ala Ile
                325                 330                 335

Cys Ile Ala Asn Gly His Cys Met Asn Phe Ser Asn Ala Tyr Thr Gln
            340                 345                 350

Arg Val Cys Asp Arg Val Pro Ile Asp Gly Phe Ser Gln Asn Glu Asn
        355                 360                 365

Lys Asn Ser Tyr Leu Cys Asn Thr Gly Gly Arg Met His Leu Val Cys
    370                 375                 380

Pro Met Ser Lys Ser Pro Tyr Val Asp Pro His Lys Ser Gly His Glu
385                 390                 395                 400

Ile Trp Glu Glu Phe Ser Met Ser Phe Thr Pro Ala Val Lys Glu Val
                405                 410                 415

Val Glu Phe Ala Lys Arg Ile Pro Gly Phe Arg Asp Leu Ser Gln His
            420                 425                 430

Asp Gln Val Asn Leu Leu Lys Ala Gly Thr Phe Glu Val Leu Met Val
        435                 440                 445

Arg Phe Ala Ser Leu Phe Asp Ala Lys Glu Arg Thr Val Thr Phe Leu
    450                 455                 460

Ser Gly Lys Lys Tyr Ser Val Asp Asp Leu His Ser Met Gly Ala Gly
465                 470                 475                 480

Asp Leu Leu Asn Ser Met Phe Glu Phe Ser Glu Lys Leu Asn Ala Leu
                485                 490                 495

Gln Leu Ser Asp Glu Glu Met Ser Leu Phe Thr Ala Val Val Leu Val
            500                 505                 510

Ser Ala Asp Arg Ser Gly Ile Glu Asn Val Asn Ser Val Glu Ala Leu
        515                 520                 525

Gln Glu Thr Leu Ile Arg Ala Leu Arg Thr Leu Ile Met Lys Asn His
    530                 535                 540

Pro Asn Glu Ala Ser Ile Phe Thr Lys Leu Leu Leu Lys Leu Pro Asp
545                 550                 555                 560

Leu Arg Ser Leu Asn Asn Met His Ser Glu Glu Leu Leu Ala Phe Lys
                565                 570                 575

Val His

<210> SEQ ID NO 9
<211> LENGTH: 20
<212> TYPE: DNA
<213> ORGANISM: Artificial Sequence
<220> FEATURE:
<223> OTHER INFORMATION: forward primer A for detection of E4bp4
      wildtype allele

<400> SEQUENCE: 9
ctctgagctt ggctgatgtg                                              20

<210> SEQ ID NO 10
<211> LENGTH: 20
<212> TYPE: DNA
<213> ORGANISM: Artificial Sequence
<220> FEATURE:
```

```
<223> OTHER INFORMATION: reverse primer for the detection of E4bp4

<400> SEQUENCE: 10
gcttcaagtc tccaccaagc                                                   20

<210> SEQ ID NO 11
<211> LENGTH: 20
<212> TYPE: DNA
<213> ORGANISM: Artificial Sequence
<220> FEATURE:
<223> OTHER INFORMATION: primer for the detection of the E4bp4 null
      allele

<400> SEQUENCE: 11
ccatgctcct gtcttgatga                                                   20

<210> SEQ ID NO 12
<211> LENGTH: 8
<212> TYPE: PRT
<213> ORGANISM: Artificial Sequence
<220> FEATURE:
<223> OTHER INFORMATION: side chain on SUMO modified peptide

<400> SEQUENCE: 12

Gly Gly Thr Gln Gln Gln Phe Val
1               5

<210> SEQ ID NO 13
<211> LENGTH: 20
<212> TYPE: PRT
<213> ORGANISM: Mus musculus

<400> SEQUENCE: 13

Met Gln Leu Arg Lys Met Gln Thr Ile Lys Lys Glu Pro Ala Pro Leu
1               5                   10                  15

Asp Pro Thr Ser
            20

<210> SEQ ID NO 14
<211> LENGTH: 20
<212> TYPE: PRT
<213> ORGANISM: Rattus rattus

<400> SEQUENCE: 14

Met Gln Leu Arg Lys Met Gln Ala Ile Lys Lys Glu Pro Ala Ser Leu
1               5                   10                  15

Asp Pro Thr Gly
            20

<210> SEQ ID NO 15
<211> LENGTH: 20
<212> TYPE: PRT
<213> ORGANISM: Homo sapiens

<400> SEQUENCE: 15

Met Gln Leu Arg Lys Met Gln Thr Val Lys Lys Glu Gln Ala Ser Leu
1               5                   10                  15

Asp Ala Ser Ser
            20

<210> SEQ ID NO 16
<211> LENGTH: 20
<212> TYPE: PRT
<213> ORGANISM: Gallus gallus
```

<400> SEQUENCE: 16

Met Gln Leu Arg Lys Met Gln Thr Leu Lys Lys Glu His Gly Ser Val
1               5                   10                  15

Asp Thr Ser Ser
            20

<210> SEQ ID NO 17
<211> LENGTH: 15
<212> TYPE: PRT
<213> ORGANISM: Xenopus laevis

<400> SEQUENCE: 17

Met Pro Thr Ile Lys Lys Glu Gln Glu Cys Ala Asp Ser Arg Met
1               5                   10                  15

<210> SEQ ID NO 18
<211> LENGTH: 20
<212> TYPE: PRT
<213> ORGANISM: Mus musculus

<400> SEQUENCE: 18

Leu Glu Asn Lys Leu Ile Ala Leu Gly Glu Glu Asn Ala Thr Leu Lys
1               5                   10                  15

Ala Glu Leu Leu
            20

<210> SEQ ID NO 19
<211> LENGTH: 20
<212> TYPE: PRT
<213> ORGANISM: Rattus rattus

<400> SEQUENCE: 19

Leu Glu Asn Lys Leu Ile Ala Leu Gly Glu Glu Asn Ala Thr Leu Lys
1               5                   10                  15

Ala Glu Leu Leu
            20

<210> SEQ ID NO 20
<211> LENGTH: 20
<212> TYPE: PRT
<213> ORGANISM: Homo sapiens

<400> SEQUENCE: 20

Leu Glu Asn Lys Leu Ile Ala Leu Gly Glu Glu Asn Ala Thr Leu Lys
1               5                   10                  15

Ala Glu Leu Leu
            20

<210> SEQ ID NO 21
<211> LENGTH: 20
<212> TYPE: PRT
<213> ORGANISM: Gallus gallus

<400> SEQUENCE: 21

Leu Glu Asn Lys Leu Ile Ala Leu Gly Glu Glu Asn Ala Thr Leu Lys
1               5                   10                  15

Ala Glu Leu Leu
            20

<210> SEQ ID NO 22
<211> LENGTH: 20

```
<212> TYPE: PRT
<213> ORGANISM: Xenopus laevis

<400> SEQUENCE: 22

Leu Glu Asn Lys Leu Ile Ala Leu Gly Glu Glu Asn Ala Ser Leu Lys
1               5                   10                  15

Thr Glu Leu Leu
            20

<210> SEQ ID NO 23
<211> LENGTH: 20
<212> TYPE: PRT
<213> ORGANISM: Mus musculus

<400> SEQUENCE: 23

Pro Glu Asn Lys Phe Pro Val Ile Lys Gln Glu Pro Val Glu Leu Glu
1               5                   10                  15

Ser Phe Ala Arg
            20

<210> SEQ ID NO 24
<211> LENGTH: 20
<212> TYPE: PRT
<213> ORGANISM: Rattus rattus

<400> SEQUENCE: 24

Pro Glu Asn Lys Phe Pro Val Ile Lys Gln Glu Pro Val Glu Leu Glu
1               5                   10                  15

Ser Phe Ala Arg
            20

<210> SEQ ID NO 25
<211> LENGTH: 20
<212> TYPE: PRT
<213> ORGANISM: Homo sapiens

<400> SEQUENCE: 25

Pro Glu Asn Lys Phe Gln Ile Ile Lys Gln Glu Pro Met Glu Leu Glu
1               5                   10                  15

Ser Tyr Thr Arg
            20

<210> SEQ ID NO 26
<211> LENGTH: 17
<212> TYPE: PRT
<213> ORGANISM: Gallus gallus

<400> SEQUENCE: 26

Pro Glu Asn Lys Phe Gln Ile Ile Lys Gln Glu Pro Ile Glu Leu Glu
1               5                   10                  15

Arg

<210> SEQ ID NO 27
<211> LENGTH: 20
<212> TYPE: PRT
<213> ORGANISM: Xenopus laevis

<400> SEQUENCE: 27

Thr Asp Ile Lys Ser Gln Arg Ile Lys Gln Glu Gln Met Glu Ala Gly
1               5                   10                  15

Asn Phe Ser Arg
            20
```

```
<210> SEQ ID NO 28
<211> LENGTH: 20
<212> TYPE: PRT
<213> ORGANISM: Mus musculus

<400> SEQUENCE: 28

Arg Ile Lys Ala Lys Ala Met Gln Val Lys Val Glu Ala Leu Asp Ser
1               5                   10                  15

Glu Phe Glu Gly
            20

<210> SEQ ID NO 29
<211> LENGTH: 20
<212> TYPE: PRT
<213> ORGANISM: Rattus rattus

<400> SEQUENCE: 29

Arg Ile Lys Ala Lys Ala Met Gln Val Lys Val Glu Ala Leu Asp Ser
1               5                   10                  15

Glu Phe Glu Gly
            20

<210> SEQ ID NO 30
<211> LENGTH: 20
<212> TYPE: PRT
<213> ORGANISM: Homo sapiens

<400> SEQUENCE: 30

Arg Ile Lys Ala Lys Ala Met Gln Ile Lys Val Glu Ala Phe Asp Asn
1               5                   10                  15

Glu Phe Glu Ala
            20

<210> SEQ ID NO 31
<211> LENGTH: 20
<212> TYPE: PRT
<213> ORGANISM: Gallus gallus

<400> SEQUENCE: 31

Arg Ile Lys Ala Lys Ala Met Gln Val Lys Val Glu Ala Met Asp Asn
1               5                   10                  15

Asp Tyr Asp Ala
            20

<210> SEQ ID NO 32
<211> LENGTH: 20
<212> TYPE: PRT
<213> ORGANISM: Xenopus laevis

<400> SEQUENCE: 32

Arg Ile Lys Ala Lys Ala Met Gln Ile Lys Val Glu Ser Leu Glu Ser
1               5                   10                  15

Glu Leu Asn Ser
            20

<210> SEQ ID NO 33
<211> LENGTH: 20
<212> TYPE: PRT
<213> ORGANISM: Mus musculus
```

<400> SEQUENCE: 33

Val Thr Asn Ile Gln Asp Trp Ser Leu Lys Ser Glu His Trp His His
1               5                   10                  15

Lys Glu Leu Ser
            20

<210> SEQ ID NO 34
<211> LENGTH: 20
<212> TYPE: PRT
<213> ORGANISM: Rattus rattus

<400> SEQUENCE: 34

Val Thr Asn Ile Gln Asp Trp Ser Leu Arg Ser Glu His Trp His His
1               5                   10                  15

Lys Glu Leu Gly
            20

<210> SEQ ID NO 35
<211> LENGTH: 20
<212> TYPE: PRT
<213> ORGANISM: Homo sapiens

<400> SEQUENCE: 35

Val Thr Asn Ile Gln Asp Trp Ser Leu Lys Ser Glu His Trp His Gln
1               5                   10                  15

Lys Glu Leu Ser
            20

<210> SEQ ID NO 36
<211> LENGTH: 20
<212> TYPE: PRT
<213> ORGANISM: Gallus gallus

<400> SEQUENCE: 36

Val Thr Asn Ile Gln Asp Trp Ser Leu Lys Pro Glu Leu Trp His Gln
1               5                   10                  15

Lys Glu Leu Asn
            20

<210> SEQ ID NO 37
<211> LENGTH: 20
<212> TYPE: PRT
<213> ORGANISM: Xenopus laevis

<400> SEQUENCE: 37

Val Thr Asn Ile Gln Asp Trp Pro Leu Lys Pro Gly Gln Trp His His
1               5                   10                  15

Arg Glu Leu Glu
            20

<210> SEQ ID NO 38
<211> LENGTH: 27
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 38
ctatattttt gccttgacag ctaaagg                                27

```
<210> SEQ ID NO 39
<211> LENGTH: 20
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 39
gaagtacgaa gcatgcttgc                                                    20

<210> SEQ ID NO 40
<211> LENGTH: 22
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 40
cacatctgtg agctattttt gg                                                 22

<210> SEQ ID NO 41
<211> LENGTH: 24
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 41
gactgactaa actaacattc ccac                                               24

<210> SEQ ID NO 42
<211> LENGTH: 20
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 42
ctcagaaact ggcctcaagc                                                    20

<210> SEQ ID NO 43
<211> LENGTH: 19
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 43
cacttgcagt caggcgttc                                                     19

<210> SEQ ID NO 44
<211> LENGTH: 20
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 44
cacgccatct taaagagctc                                                    20

<210> SEQ ID NO 45
```

```
<211> LENGTH: 22
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 45
gtaaccaact gcactcttct cc                                            22

<210> SEQ ID NO 46
<211> LENGTH: 19
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 46
caccaagaat tcccaggag                                                19

<210> SEQ ID NO 47
<211> LENGTH: 20
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 47
gagtgcagtc acgtgctgac                                               20

<210> SEQ ID NO 48
<211> LENGTH: 23
<212> TYPE: DNA
<213> ORGANISM: Artificial Sequence
<220> FEATURE:
<223> OTHER INFORMATION: Forward primer for amplification of putative
      E4bp4-binding regions in Notch1 locus

<400> SEQUENCE: 48
ctcagactct ctcggtaagt gtc                                           23

<210> SEQ ID NO 49
<211> LENGTH: 19
<212> TYPE: DNA
<213> ORGANISM: Artificial Sequence
<220> FEATURE:
<223> OTHER INFORMATION: Reverse primer for amplification of putative
      E4bp4-binding regions in Notch1 locus

<400> SEQUENCE: 49
cgtgtggagc tactctggc                                                19

<210> SEQ ID NO 50
<211> LENGTH: 426
<212> TYPE: DNA
<213> ORGANISM: Homo sapiens

<400> SEQUENCE: 50
atgtcaaaca tgagatgtgt ggactgtggc acttgcctgg gtcacacacg gaggcatcct    60
acccttttct ggggaaagac actgcctggg ctgaccccgg tggcggcccc agcacctcag   120
cctgcacagt gtccccccagg ttccgaagaa gatgctccag caacacagcc tgggcccag   180 ctcgcgggac ccgacccccc gtgggctccc gtgttttgta ggagacttgc cagagccggg   240
```

```
cacattgagc tgtgcaacgc cgtgggctgc gtcctttggt cctgtccccg cagccctggc    300 aggggggcatg cggtcgggca ggggctggag ggaggcgggg gctgcccttg ggccacccct    360
cctagtttgg gaggagcaga tttttgcaat accaagtata gcctatggca gaaaaaatgt    420
ctttaa                                                                426
```

<210> SEQ ID NO 51
<211> LENGTH: 141
<212> TYPE: PRT
<213> ORGANISM: Homo sapiens

<400> SEQUENCE: 51

```
Met Ser Asn Met Arg Cys Val Asp Cys Gly Thr Cys Leu Gly His Thr
1               5                  10                  15

Arg Arg His Pro Thr Leu Phe Trp Gly Lys Thr Leu Pro Gly Leu Thr
            20                  25                  30

Pro Val Ala Ala Pro Ala Pro Gln Pro Ala Gln Cys Pro Pro Gly Ser
        35                  40                  45

Glu Glu Asp Ala Pro Ala Thr Gln Pro Gly Pro Gln Leu Ala Gly Pro
    50                  55                  60

Asp Pro Pro Trp Ala Pro Val Phe Cys Arg Arg Leu Ala Arg Ala Gly
65                  70                  75                  80

His Ile Glu Leu Cys Asn Ala Val Gly Cys Val Leu Trp Ser Cys Pro
                85                  90                  95

Arg Ser Pro Gly Arg Gly His Ala Val Gly Gln Gly Leu Glu Gly Gly
            100                 105                 110

Gly Gly Cys Pro Trp Ala Thr Pro Pro Ser Leu Gly Gly Ala Asp Phe
        115                 120                 125

Cys Asn Thr Lys Tyr Ser Leu Trp Gln Lys Lys Cys Leu
    130                 135                 140
```